United States Patent
Allen et al.

(10) Patent No.: US 10,851,080 B2
(45) Date of Patent: *Dec. 1, 2020

(54) METHODS OF TREATMENT USING PYRROLIDINYL UREA, THIOUREA, GUANIDINE AND CYANOGUANIDINE COMPOUNDS

(71) Applicant: Array BioPharma Inc., Boulder, CO (US)

(72) Inventors: Shelley Allen, Boulder, CO (US); Barbara J. Brandhuber, Golden, CO (US); Timothy Kercher, San Diego, CA (US); Gabrielle R. Kolakowski, Boulder, CO (US); Shannon L. Winski, Boulder, CO (US)

(73) Assignee: Array Biopharma Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/851,418

(22) Filed: Dec. 21, 2017

(65) Prior Publication Data

US 2018/0179182 A1   Jun. 28, 2018

Related U.S. Application Data

(62) Division of application No. 14/442,613, filed as application No. PCT/US2013/069729 on Nov. 12, 2013, now Pat. No. 9,896,435.

(60) Provisional application No. 61/725,913, filed on Nov. 13, 2012.

(51) Int. Cl.
  *A61P 29/00*    (2006.01)
  *C07D 401/14*   (2006.01)
  *C07C 403/14*   (2006.01)
  *A61P 35/00*    (2006.01)
  *C07D 403/12*   (2006.01)

(52) U.S. Cl.
  CPC ............ *C07D 401/14* (2013.01); *A61P 29/00* (2018.01); *A61P 35/00* (2018.01); *C07C 403/14* (2013.01); *C07D 403/12* (2013.01)

(58) Field of Classification Search
  None
  See application file for complete search history.

(56) References Cited

U.S. PATENT DOCUMENTS

| | | | |
|---|---|---|---|
| 5,849,779 A | 12/1998 | Hirota et al. | |
| 5,998,424 A | 12/1999 | Galemmo, Jr. et al. | |
| 6,197,798 B1 | 3/2001 | Fink et al. | |
| 6,410,533 B1 | 6/2002 | Hirth et al. | |
| 7,223,782 B2 | 5/2007 | Atkinson et al. | |
| 7,625,915 B2 | 12/2009 | Dumas et al. | |
| 8,592,454 B2 | 11/2013 | Shirai et al. | |
| 9,163,017 B2 | 10/2015 | Degoey et al. | |
| 9,562,055 B2 | 2/2017 | Allen et al. | |
| 9,878,997 B2 * | 1/2018 | Allen .................. | C07D 401/14 |
| 9,896,435 B2 | 2/2018 | Kercher et al. | |

FOREIGN PATENT DOCUMENTS

| | | |
|---|---|---|
| EP | 0761658 A1 | 12/1997 |
| EP | 1043995 B1 | 11/2006 |
| EP | 2033955 A1 | 3/2009 |
| EP | 1451160 B1 | 1/2010 |
| EP | 2336105 A1 | 6/2011 |
| JP | 2005206527 A | 8/2005 |
| WO | 1998004521 A1 | 2/1998 |
| WO | 1999023091 A1 | 5/1999 |
| WO | 1999032110 A1 | 7/1999 |
| WO | 1999032111 A1 | 7/1999 |
| WO | 2000039116 A1 | 7/2000 |
| WO | 2000043384 A1 | 7/2000 |
| WO | 2001012188 A1 | 2/2001 |
| WO | 2002002525 A2 | 1/2002 |
| WO | 2002088101 A2 | 11/2002 |
| WO | 2002090326 A1 | 11/2002 |
| WO | 2003037274 A2 | 5/2003 |
| WO | 2003045920 A1 | 6/2003 |
| WO | 2003051275 A2 | 6/2003 |
| WO | 2004005262 A2 | 1/2004 |
| WO | 2004032870 A2 | 4/2004 |
| WO | 2004060305 A2 | 7/2004 |
| WO | 2004060306 A2 | 7/2004 |
| WO | 2004061084 A2 | 7/2004 |
| WO | 2004111009 A1 | 12/2004 |
| WO | 2005024755 A2 | 3/2005 |
| WO | 2005048948 A2 | 6/2005 |
| WO | 2005110994 A2 | 11/2005 |
| WO | 2006014290 A2 | 2/2006 |
| WO | 2006068591 A1 | 6/2006 |
| WO | 2006070198 A1 | 7/2006 |
| WO | 2006071940 A2 | 7/2006 |
| WO | 2006081034 A2 | 8/2006 |
| WO | 2006123257 A2 | 11/2006 |

(Continued)

OTHER PUBLICATIONS

Adriaenssens, et al., "Nerve growth factor is a potential therapeutic target in breast cancer", Cancer Res 68(2), 346-351 (2008).
Asaumi, et al., "Expression of neurotrophins and their receptors (TRK) during fracture healing", Bone 26(6), 625-633 (2000).
Bardelli, "Mutational analysis of the tyrosine kinome in colorectal cancers", Science 300, 949 (2003).
Bhattacharya, et al., "Identification of novel series of pyrazole and indole-urea based DFG-out PYK2 inhibitors", Bioorganic & Medicinal Chemistry Letters 22(24), 7523-7592 (2012).
Bouhana, et al., "Comparison of Analgesic Effects of an Allosteric Inhibitor of TrkA to that of an ATP Site Inhibitor of the pan-Trk Axis in a Rodent Model of Inflammatory Pain", Gordon Conference, Salve Regina University, Newport, RI, 1 page, Jun. 7, 2011.
Brodeur, et al., "Neuroblastoma: biological insights into a clinical enigma", Nat Rev Cancer 3, 203-216 (2003).

(Continued)

*Primary Examiner* — Layla Soroush
(74) *Attorney, Agent, or Firm* — Viksnins Harris Padys Malen LLP

(57) ABSTRACT

Compounds useful for the treatment of pain or cancer in a mammal.

16 Claims, No Drawings

(56) References Cited

FOREIGN PATENT DOCUMENTS

| | | |
|---|---|---|
| WO | 2007008917 A2 | 1/2007 |
| WO | 2007059202 A2 | 5/2007 |
| WO | 2007061882 A2 | 5/2007 |
| WO | 2007064872 A2 | 6/2007 |
| WO | 2008016811 A2 | 2/2008 |
| WO | 2008021859 A1 | 2/2008 |
| WO | 2008033999 A2 | 3/2008 |
| WO | 2008034008 A2 | 3/2008 |
| WO | 2008046003 A2 | 4/2008 |
| WO | 2008131276 A1 | 10/2008 |
| WO | 2008150899 A1 | 12/2008 |
| WO | 2009140128 A2 | 11/2009 |
| WO | 2010032856 A1 | 3/2010 |
| WO | 2010033941 A1 | 3/2010 |
| WO | 2010040663 A1 | 4/2010 |
| WO | 2010048314 A1 | 4/2010 |
| WO | 2010059719 A2 | 5/2010 |
| WO | 2010075376 A2 | 7/2010 |
| WO | 2010077680 A2 | 7/2010 |
| WO | 2010104488 A1 | 9/2010 |
| WO | 2010125799 A1 | 11/2010 |
| WO | 2011006074 A1 | 1/2011 |
| WO | 2011032291 A1 | 3/2011 |
| WO | 2011146336 A1 | 11/2011 |
| WO | 2012158413 A2 | 11/2012 |
| WO | 2012158413 A3 | 5/2013 |
| WO | 2013063214 A1 | 5/2013 |
| WO | 2013096226 A1 | 6/2013 |
| WO | 2013176970 A1 | 11/2013 |
| WO | 2014052563 A1 | 4/2014 |
| WO | 2014052566 A1 | 4/2014 |
| WO | 2014078322 A1 | 5/2014 |
| WO | 2014078323 A1 | 5/2014 |
| WO | 2014078325 A1 | 5/2014 |
| WO | 2014078328 A1 | 5/2014 |
| WO | 2014078331 A1 | 5/2014 |
| WO | 2014078372 A1 | 5/2014 |
| WO | 2014078408 A1 | 5/2014 |
| WO | 2014078417 A1 | 5/2014 |
| WO | 2014078454 A1 | 5/2014 |
| WO | 2015039333 A1 | 3/2015 |
| WO | 2015042085 A2 | 3/2015 |
| WO | 2014078378 A1 | 5/2015 |

OTHER PUBLICATIONS

Bruno, "1-Methyl and 1-(2-hydroxyalkyl)-5-(3-alkyl/cycloalkyl/phenyl/naphthylureido)-1H-pyrazole-4-carboxylic acid ethyl esters as potent human neutrophil chemotaxis inhibitors", Bioorganic & Medicinal Chemistry 17(9), 3379-3387 (2009).

Burger, et al., "5-Amino-4-trifluormethylthiazole and 5-Aminomethyl-4-trifluormethyl-1,3-azole: Nützliche Ausgangssubstanzen für Wirkstoft-Synthesen", Synthesis 4, 360-365 (1990).

Chambers, et al., "Synthesis and structure-activity relationships of a series of (1H-pyrazol-4-yl)acetamide antagonists of the P2X7 receptor", Bioorganic & Medicinal Chemistry Letters 20(10), 3161-3164 (2010).

Davidson, et al., "Expression and activation of the nerve growth factor receptor TrkA in serous ovarian carcinoma", Clin Cancer Res 9, 2248-2259 (2003).

Davies, et al., "Asymmetric Synthesis of 3, 4-anti- and 3, 4-syn-substituted Aminopyrrolidines via Lithium Amide Conjugate Addition", Organic and Biomolecular Chemistry, vol. 5, 1961-1969 (2007).

Delafoy, et al., "Role of nerve growth factor in the trinitrobenzene sulfonic acid-induced colonic hypersensitivity", Pain 105, 489-497 (2003).

Demelo-Jorge, et al., "The Chagas' Disease Parasite *Trypanosoma cruzi* Exploits Nerve Growth Factor Receptor TrkA to Infect Mammalian Hosts", Cell Host & Microbe 1(4), 251-261 (2007).

Di Mola, et al., "Nerve growth factor and Trk high affinity receptor (TrkA) gene expression in inflammatory bowel disease", Gut 46(5), 670-679 (2000).

Dou, et al., "Increased nerve growth factor and its receptors in atopic dermatitis: an immunohistochemical study", Archives of Dermatological Research 298(1), 31-37 (2006).

Du, et al., "Expression of NGF family and their receptors in gastric carcinoma: A cDNA microarray study", World Journal of Gastroenterology 9(7), 1431-1434 (2003).

Eguchi, et al., "Fusion of ETV6 to neurotrophin-3 receptor TRKC in acute myeloid leukemia with t(12;15)(p13;q25)", Blood 93(4), 1355-1363 (1999).

El Haddad, et al., "A convenient synthesis of pyrazolo[3,4-d]pyrimidine-4,6-dione and pyrazolo[4,3-d]pyrimidine-5,7-dione derivatives", J Heterocyclic Chem 37(5), 1247-1252 (2000).

Eliav, et al., "The kappa opioid agonist GR89 696 blocks hyperalgesia and allodynia in rat models of peripheral neuritis and neuropathy", Pain 79 (2-3), 255-264 (1999).

Euthus, et al., "ETV6-NTRK3—Trk-ing the primary event in human secretory breast cancer", Cancer Cell 2(5), 347-348 (2002).

Freund-Michel, et al., "The nerve growth factor and its receptors in airway inflammatory diseases", Pharmacology & Therapeutics 117(1), 52-76 (2008).

Greco, et al., "Rearrangements of NTRK1 gene in papillary thyroid carcinoma", Molecular and Cellular Endocrinology 321(1), 44-49 (2010).

Gruber-Olipitz, et al., "Synthesis, chaperoning, and metabolism of proteins are regulated by NT-3/TrkC signaling in The medulloblastoma cell line DAOY", Journal of Proteome Research 7(5), 1932-1944 (2008).

Gwak, et al., "Attenuation of mechanical hyperalgesia following spinal cord injury by administration of antibodies to nerve growth factor in the rat", Neurosci Lett 336, 117-120 (2003).

Han, et al., "Structural characterization of proline-rich tyrosine kinase 2 (PYK2) reveals a unique (DFG-out) conformation and enables inhibitor design", J Biological Chem 284(19), 13199-13201 (2009).

Herzberg, et al., "NGF involvement in pain induced by chronic constriction injury of the rat sciatic nerve", Neuroreport 8, 1613-1618 (1997).

Hu, et al., "Decrease in bladder overactivity with REN1820 in rats with cyclophosphamide induced cystitis", Journal of Urology 173(3), 1016-1021 (2005).

Jaggar, et al., "Inflammation of the rat urinary bladder is associated with a referred thermal hyperalgesia which is nerve growth factor dependent", Br J Anaesth 83, 442-448 (1999).

Jin, et al., "TrkC plays an essential role in breast tumor growth and metastasis", Carcinogenesis 31(11), 1939-1947 (2010).

Kaymakcioglu, et al., "Synthesis and biological evaluation of new N-substituted-N'-(3,5-di/1,3,5-trimethylpyrazole-4-yl)thiourea/urea derivatives", European Journal of Pharmaceutical Sciences 26(1), 97-103 (2005).

Lamb, et al., "Nerve growth factor and gastric hyperalgesia in the rat", Neurogastroenterol. Motil. 15, 355-361 (2003).

Li, et al., Chinese Journal of Cancer Prevention and Treatment 16(6), 428-430 [with English Abstract] (2009).

Li, et al., "Lumbar 5 ventral root transection-induced upregulation of nerve growth factor in sensory neurons and their target tissues: a mechanism in neuropathic pain", Mol Cell Neurosci 23, 232-250 (2003).

Ma, et al., "The progressive tactile hyperalgesia induced by peripheral inflammation is nerve growth factor dependent", NeuroReport 8, 807-810 (1997).

Mantyh, et al., "Antagonism of Nerve Growth Factor-TrkA Signaling and the Relief of Pain", Anesthesiology vol. 115(1), 189-204 (2011).

McCarthy, et al., "Tropomyosin receptor kinase inhibitors: a patent update 2009-2013", Expert Opin Ther Patents 24(7), 731-744 (2014).

McMahon, et al., "The biological effects of endogenous nerve growth factor on adult sensory neurons revealed by a trkA-IgG fusion molecule", Nat Med 1, 774-780 (1995).

(56) References Cited

OTHER PUBLICATIONS

Meyer, et al., "Remarkable leukemogenic potency and quality of a constitutively active neurotrophin receptor, deltaTrkA", Leukemia 21(10), 2171-2180 (2007).
Montalban, et al., "KR-003048, a potent, orally active inhibitor of p38 mitogen-activated protein kinase", European J Pharmacology 632(1-3), 93-102 (2010).
Nakagawara, "Trk receptor tyrosine kinases: a bridge between cancer and neural development", Cancer Letters 169, 107-114 (2001).
Patapoutian, et al., "Trk receptors: mediators of neurotrophin action", Current Opinion in Neurobiology 11, 272-280 (2001).
Patent Cooperation Treaty, International Searching Authority, Search Report and Written Opinion for PCT/US2013/069729, 13 pages, dated Dec. 20, 2013.
Pierottia, et al., "Oncogenic rearrangements of the NTRK1/NGF receptor", Cancer Letters 232, 90-98 (2006).
Pinski, et al., "Trk receptor inhibition induces apoptosis of proliferating but not quiescent human osteoblasts", Cancer Research 62, 986-989 (2002).
Ramer, et al., "Adrenergic innervation of rat sensory ganglia following proximal or distal painful sciatic neuropathy: distinct mechanisms revealed by anti-NGF treatment", Eur J Neurosci 11, 837-846 (1999).
Raychaudhuri, et al., "K252a, a high-affinity nerve growth factor receptor blocker, improves psoriasis: an in vivo study using the severe combined immunodeficient mouse-human skin model", J Investigative Dermatology 122(3), 812-819 (2004).
Ricci, et al., "Neurotrophins and neurotrophin receptors in human lung cancer", American Journal of Respiratory Cell and Molecular Biology 25(4), 439-446 (2001).
Ro, et al., "Effect of NGF and anti-NGF on neuropathic pain in rats following chronic constriction injury of the sciatic nerve", Pain 79(2-3), 265-274 (1999).
Shelton, et al., "Nerve growth factor mediates hyperalgesia and cachexia in auto-immune arthritis", Pain 116, 8-16 (2005).
Theodosiou, et al., "Hyperalgesia due to nerve damage: role of nerve growth factor", Pain 81, 245-255 (1999).
Truzzi, et al., "Neurotrophins in healthy and diseased skin", Dermato-Endocrinology, 3(1), 32-36 (2011).
Tsuzuki, et al., "Practical Synthesis of (3S,4S)-3-methoxy-4-methylaminopyrrolidine", Tetrahedron: Asymmetry 12, 2989-2997 (2001).
Wadhwa, et al., "Expression of the neurotrophin receptors Trk A and Trk B in adult human astrocytoma and glioblastoma", Journal of Biosciences 28(2), 181-188 (2003).
Wang, et al., "Trk kinase inhibitors as new treatments for cancer and pain", Expert Opinion on Therapeutic Patents, 19(3), 305-319 (2009).
Woolf, et al., "Nerve growth factor contributes to the generation of inflammatory sensory hypersensitivity", Neuroscience 62, 327-331 (1994).
Yilmaz, et al., "Theraputic targeting of Trk supresses tumor proliferation and enhances cisplatin activity in HNSCC", Cancer Biology & Therapy 10(6), 644-653 (2010).
Zahn, et al., "Effect of blockade of nerve growth factor and tumor necrosis factor on pain behaviors after plantar incision", J Pain 5, 157-163 (2004).

\* cited by examiner

METHODS OF TREATMENT USING PYRROLIDINYL UREA, THIOUREA, GUANIDINE AND CYANOGUANIDINE COMPOUNDS

CROSS-REFERENCE TO RELATED APPLICATION(S)

This application is a Divisional of U.S. application Ser. No. 14/442,613, filed May 13, 2015, which is a 35 U.S.C. § 371 application of International Application No. PCT/US2013/069729, filed Nov. 12, 2013, which claims priority to U.S. Provisional Application No. 61/725,913, filed Nov. 13, 2012, which applications are herein incorporated by reference in their entirety.

BACKGROUND OF THE INVENTION

The present invention relates to novel compounds, to pharmaceutical compositions comprising the compounds, to processes for making the compounds and to the use of the compounds in therapy. More particularly, it relates to pyrrolidinyl urea, thiourea, guanidine and cyanoguanidine compounds which exhibit TrkA kinase inhibition, and which are useful in the treatment of pain, cancer, inflammation/inflammatory diseases, neurodegenerative diseases, certain infectious diseases, Sjogren's syndrome, endometriosis, diabetic peripheral neuropathy, prostatitis or pelvic pain syndrome.

The current treatment regimens for pain conditions utilize several classes of compounds. The opioids (such as morphine) have several drawbacks including emetic, constipatory and negative respiratory effects, as well as the potential for addictions. Non-steroidal anti-inflammatory analgesics (NSAIDs, such as COX-1 or COX-2 types) also have drawbacks including insufficient efficacy in treating severe pain. In addition, COX-1 inhibitors can cause ulcers of the mucosa. Accordingly, there is a continuing need for new and more effective treatments for the relief of pain, especially chronic pain.

Trk's are the high affinity receptor tyrosine kinases activated by a group of soluble growth factors called neurotrophins (NT). The Trk receptor family has three members: TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trk's are widely expressed in neuronal tissue and are implicated in the maintenance, signaling and survival of neuronal cells (Patapoutian, A. et al., *Current Opinion in Neurobiology*, 2001, 11, 272-280).

Inhibitors of the Trk/neurotrophin pathway have been demonstrated to be effective in numerous pre-clinical animal models of pain. For example, antagonistic NGF and TrkA antibodies such as RN-624 have been shown to be efficacious in inflammatory and neuropathic pain animal models (Woolf, C. J. et al. (1994) *Neuroscience* 62, 327-331; Zahn, P. K. et al. (2004) *J. Pain* 5, 157-163; McMahon, S. B. et al., (1995) *Nat. Med.* 1, 774-780; Ma, Q. P. and Woolf, C. J. (1997) *NeuroReport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motil.* 15, 355-361; Jaggar, S. I. et al. (1999) *Br. J. Anaesth.* 83, 442-448) and neuropathic pain animal models (Ramer, M. S. and Bisby, M. A. (1999) *Eur. J. Neurosci.* 11, 837-846; Ro, L. S. et al. (1999); Herzberg, U. et al., *Pain* 79, 265-274 (1997) *Neuroreport* 8, 1613-1618; Theodosiou, M. et al. (1999) *Pain* 81, 245-255; Li, L. et al. (2003) *Mol. Cell. Neurosci.* 23, 232-250; Gwak, Y. S. et al. (2003) *Neurosci. Lett.* 336, 117-120).

It has also been shown that NGF secreted by tumor cells and tumor invading macrophages directly stimulates TrkA located on peripheral pain fibers. Using various tumor models in both mice and rats, it was demonstrated that neutralizing NGF with a monoclonal antibody inhibits cancer related pain to a degree similar or superior to the highest tolerated dose of morphine. Because TrkA kinase may serve as a mediator of NGF driven biological responses, inhibitors of TrkA and/or other Trk kinases may provide an effective treatment for chronic pain states.

Recent literature has also shown that overexpression, activation, amplification and/or mutation of Trk kinases are associated with many cancers including neuroblastoma (Brodeur, G. M., *Nat. Rev. Cancer* 2003, 3, 203-216), ovarian (Davidson. B., et al., *Clin. Cancer Res.* 2003, 9, 2248-2259), colorectal cancer (Bardelli, A., *Science* 2003, 300, 949), melanoma (Truzzi, F., et al., *Dermato-Endocrinology* 2008, 3 (1), pp. 32-36), head and neck cancer (Yilmaz, T., et al., *Cancer Biology and Therapy* 2010, 10 (6), pp. 644-653), gastric carcinoma (Du, J. et al., *World Journal of Gastroenterology* 2003, 9 (7), pp. 1431-1434), lung carcinoma (Ricci A., et al., *American Journal of Respiratory Cell and Molecular Biology* 25 (4), pp. 439-446), breast cancer (Jin, W., et al., *Carcinogenesis* 2010, 31 (11), pp. 1939-1947), Glioblastoma (Wadhwa, S., et al., *Journal of Biosciences* 2003, 28 (2), pp. 181-188), medulloblastoma (Gruber-Olipitz, M., et al., *Journal of Proteome Research* 2008, 7 (5), pp. 1932-1944), secratory breast cancer (Euthus, D. M., et al., *Cancer Cell* 2002, 2 (5), pp. 347-348), salivary gland cancer (Li, Y.-G., et al., *Chinese Journal of Cancer Prevention and Treatment* 2009, 16 (6), pp. 428-430), papillary thyroid carcinoma (Greco, A., et al., *Molecular and Cellular Endocrinology* 2010, 321 (1), pp. 44-49) and adult myeloid leukemia (Eguchi, M., et al., *Blood* 1999, 93 (4), pp. 1355-1363). In preclinical models of cancer, non-selective small molecule inhibitors of TrkA, B and C were efficacious in both inhibiting tumor growth and stopping tumor metastasis (Nakagawara, A. (2001) *Cancer Letters* 169:107-114; Meyer, J. et al. (2007) *Leukemia*, 1-10; Pierottia, M. A. and Greco A., (2006) *Cancer Letters* 232:90-98; Eric Adriaensens, E., et al. *Cancer Res* (2008) 68:(2) 346-351).

In addition, inhibition of the neurotrophin/Trk pathway has been shown to be effective in treatment of pre-clinical models of inflammatory diseases with NGF antibodies or non-selective small molecule inhibitors of TrkA. For example, inhibition of the neurotrophin/Trk pathway has been implicated in preclinical models of inflammatory lung diseases including asthma (Freund-Michel, V; Frossard, N., *Pharmacology & Therapeutics* (2008) 117(1), 52-76), interstitial cystitis (Hu Vivian Y; et. al. *The Journal of Urology* (2005), 173(3), 1016-21), bladder pain syndrome (Liu, H.-T., et al., (2010) BJU International, 106 (11), pp. 1681-1685), inflammatory bowel diseases including ulcerative colitis and Crohn's disease (Di Mola, F. F, et. al., *Gut* (2000) 46(5), 670-678) and inflammatory skin diseases such as atopic dermatitis (Dou, Y.-C., et. al. *Archives of Dermatological Research* (2006) 298(1), 31-37), eczema and psoriasis (Raychaudhuri, S. P., et al., *J Investigative Dermatology* (2004) 122(3), 812-819).

The TrkA receptor is also thought to be critical to the disease process of the parasitic infection of *Trypanosoma cruzi* (Chagas disease) in human hosts (de Melo-Jorge, M. et al., *Cell Host & Microbe* (2007) 1(4), 251-261).

Trk inhibitors may also find use in treating disease related to an imbalance of the regulation of bone remodeling, such as osteoporosis, rheumatoid arthritis, and bone metastases. Bone metastases are a frequent complication of cancer, occurring in up to 70 percent of patients with advanced breast or prostate cancer and in approximately 15 to 30 percent of patients with carcinoma of the lung, colon, stomach, bladder, uterus, rectum, thyroid, or kidney. Osteolytic metastases can cause severe pain, pathologic fractures, life-threatening hypercalcemia, spinal cord compression, and other nerve-compression syndromes. For these reasons, bone metastasis is a serious and costly complication of cancer. Therefore, agents that can induce apoptosis of proliferating osteoblasts would be highly advantageous. Expression of TrkA receptors has been observed in the bone-forming area in mouse models of bone fracture (K. Asaumi, et al., *Bone* (2000) 26(6) 625-633). In addition, localization of NGF was observed in almost all bone-forming cells (K. Asaumi, et al.). Recently, it was demonstrated that a Trk inhibitor inhibits the signaling activated by neurotrophins binding to all three of the Trk receptors in human hFOB osteoblasts (J. Pinski, et al., (2002) 62, 986-989). These data support the rationale for the use of Trk inhibitors for the treatment of bone remodeling diseases, such as bone metastases in cancer patients.

Trk inhibitors may also find use in treating diseases and disorders such as Sjogren's syndrome (Fauchais, A. L., et al., (2009) Scandinavian Journal of Rheumatology, 38(1), pp. 50-57), endometriosis (Barcena De Arellano, M. L., et al., (2011) Reproductive Sciences, 18(12), pp. 1202-1210; Barcena De Arellano, et al., (2011) Fertility and Sterility, 95(3), pp. 1123-1126; Cattaneo, A., (2010) Current Opinion in Molecular Therapeutics, 12(1), pp. 94-106), diabetic peripheral neuropathy (Kim, H. C., et al., (2009) Diabetic Medicine, 26 (12), pp. 1228-1234; Siniscalco, D., et al., (2011) Current Neuropharmacology, 9(4), pp. 523-529; Ossipov, M. H., (2011) Current Pain and Headache Reports, 15(3), pp. 185-192), and prostatitis and pelvic pain syndrome (Watanabe, T., et al., (2011) BJU International, 108 (2), pp. 248-251; and Miller, L. J., et al., (2002) Urology, 59(4), pp. 603-608).

Several classes of small molecule inhibitors of Trk kinases said to be useful for treating pain or cancer are known (*Expert Opin. Ther. Patents* (2009) 19(3), 305-319).

International application publication WO 2010/032856 describes compounds represented by the formula

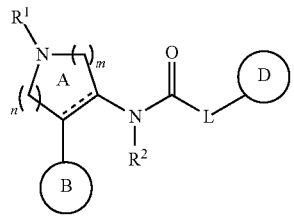

wherein ring B is an aromatic ring, ring D is an aromatic ring, and L is $NR^3$, $NR^3C(R^{4a}R^{4b})$, O or $OC(R^{4a}R^{4b})$, which are asserted to be tachykinin receptor antagonists.

SUMMARY OF THE INVENTION

It has now been found that pyrrolidinyl urea, thiourea, guanidine and cyanoguanidine compounds are inhibitors of TrkA, and useful for treating disorders and diseases such as pain, including chronic and acute pain. Compounds of the invention useful in the treatment of multiple types of pain including inflammatory pain, neuropathic pain, and pain associated with cancer, surgery, or bone fracture. In addition, compounds of the invention are useful for treating cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

More specifically, provided herein are compounds of Formula I:

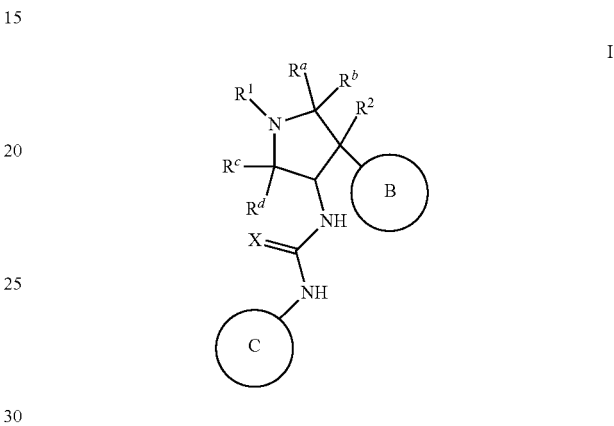

or stereoisomers, tautomers, or pharmaceutically acceptable salts, solvates or prodrugs thereof, wherein Ring B and the NH—C(=X)—NH moiety are in the trans configuration and $R^1$, $R^2$, $R^a$, $R^b$, $R^c$, $R^d$, X, Ring B and Ring C are as defined herein.

Another aspect of the present invention provides methods of treating a disease or disorder modulated by TrkA, comprising administering to a mammal in need of such treatment an effective amount of a compound of this invention or a stereoisomer, solvate or pharmaceutically acceptable salt thereof. In one embodiment, the disease and disorders include chronic and acute pain, including but not limited to inflammatory pain, neuropathic pain, and pain associated with cancer, surgery, or bone fracture. In another embodiment, the disease and disorders include, but are not limited to, cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases. In one embodiment, the treatment includes treating the mammal with a compound of this invention in combination with an additional therapeutic agent.

Another aspect of the present invention provides a pharmaceutical composition comprising a compound of the present invention or a pharmaceutically acceptable salt thereof. Another aspect of the present invention provides the compounds of the present invention for use in therapy.

Another aspect of the present invention provides the compounds of the present invention for use in the treatment of disease and disorders such as chronic and acute pain, including but not limited to inflammatory pain, neuropathic pain, and pain associated with cancer, surgery, or bone fracture. Another aspect of the present invention provides the compounds of the present invention for use in the treatment of disease and disorders selected from cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

Another aspect of the present invention provides the use of a compound of this invention in the manufacture of a medicament for the treatment of disease and disorders such as chronic and acute pain including, but not limited to, inflammatory pain, neuropathic pain, and pain associated with cancer, surgery, or bone fracture.

Another aspect of the present invention provides the use of a compound of this invention in the manufacture of a medicament for the treatment of disease and disorders selected from cancer, inflammation or inflammatory diseases, neurodegenerative diseases, certain infectious diseases, Sjogren's syndrome, endometriosis, diabetic peripheral neuropathy, prostatitis or pelvic pain syndrome, and diseases related to an imbalance of the regulation of bone remodeling, such as osteoporosis, rheumatoid arthritis, and bone metastases.

Another aspect of the present invention provides intermediates for preparing compounds of Formula I.

Another aspect of the present invention includes methods of preparing, methods of separation, and methods of purification of the compounds of this invention.

DETAILED DESCRIPTION OF THE INVENTION

Provided herein are compounds, and pharmaceutical formulations thereof, that are useful in the treatment of diseases, conditions and/or disorders modulated by TrkA. A representative compound of the invention (See Table B below), was found to be highly selective for TrkA over a panel of about 230 other kinases at 10 µM concentration. In addition, compounds of the invention such as those shown in Table A below, were found to be at least 1000-fold more selective for TrkA versus p38α.

One embodiment provides a compound of Formula I:

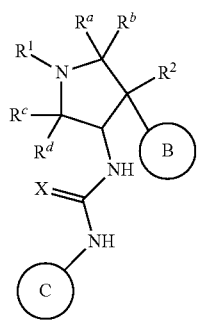

or stereoisomers, tautomers, or pharmaceutically acceptable salts, solvates or prodrugs thereof, wherein:
Ring B and the NH—C(=X)—NH moiety are in the trans configuration;
$R^a$, $R^b$, $R^c$ and $R^d$ are independently selected from H and (1-3C)alkyl,
or $R^c$ and $R^d$ are independently selected from H and (1-3C) alkyl, and $R^a$ and $R^b$ together with the atom to which they are attached form a cyclopropyl ring;

X is O, S, NH, or N—CN;
$R^1$ is (1-3C alkoxy)(1-6C)alkyl, (trifluoromethoxy)(1-6C) alkyl, (1-3C sulfanyl)(1-6C)alkyl, monofluoro(1-6C)alkyl, difluoro(1-6C)alkyl, trifluoro(1-6C)alkyl, tetrafluoro(2-6C) alkyl, pentafluro(2-6C)alkyl, cyano(1-6C)alkyl, aminocarbonyl(1-6C)alkyl, hydroxy(1-6C)alkyl, dihydroxy(2-6C) alkyl, (1-6C)alkyl, (1-3C alkylamino)(1-3C)alkyl, (1-4C alkoxycarbonyl)(1-6C)alkyl, amino(1-6C)alkyl, hydroxyl (1-3C alkoxy)(1-6C)alkyl, di(1-3C alkoxy)(1-6C)alkyl, (1-3C alkoxy)trifluoro(1-6C)alkyl, hydroxytrifluoro(1-6C) alkyl, (1-4C alkoxycarbonyl)(1-3C alkoxy)(1-6C)alkyl or hydroxycarbonyl(1-3C alkoxy)(1-6C)alkyl;

$R^2$ is H, F, or OH;
Ring B is $Ar^1$ or $hetAr^1$;
$Ar^1$ is phenyl optionally substituted with one or more substituents independently selected from halogen, $CF_3$, $CF_3O$—, (1-4C)alkoxy, hydroxy(1-4C)alkyl, (1-6C)alkyl and CN;
$hetAr^1$ is a 5-6 membered heteroaryl having 1-3 ring heteroatoms independently selected from N, S and O, and optionally substituted with one or more substituents independently selected from (1-6C)alkyl, halogen, OH, $CF_3$, $NH_2$ and hydroxy(1-2C)alkyl; Ring C is

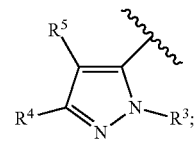

$R^3$ is H, (1-6C)alkyl, hydroxy(1-6C)alkyl, $Ar^2$, $hetCyc^1$, (3-7C)cycloalkyl, $hetAr^2$, or a C5-C8 bridged carbocyclic ring;
$Ar^2$ is phenyl optionally substituted with one or more substituents independently selected from halogen and (1-6C) alkyl;
$hetCyc^1$ is a 5-6-membered saturated or partially unsaturated heterocyclic ring having 1-2 ring heteroatoms independently selected from N and O;
$hetAr^2$ is a 5-6 membered heteroaryl ring having 1-3 ring heteroatoms independently selected from N, O and S and optionally substituted with one or more substituents independently selected from (1-6C)alkyl and halogen;
$R^4$ is selected from (1-6C alkyl)$SO_2$—, (1-6C alkyl)C (=O)— and from the structures:

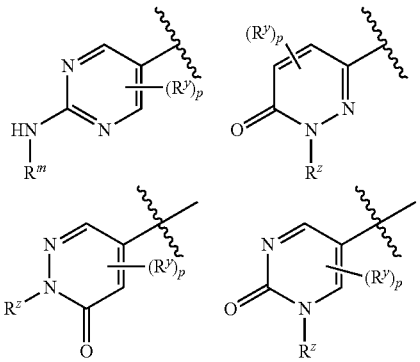

-continued

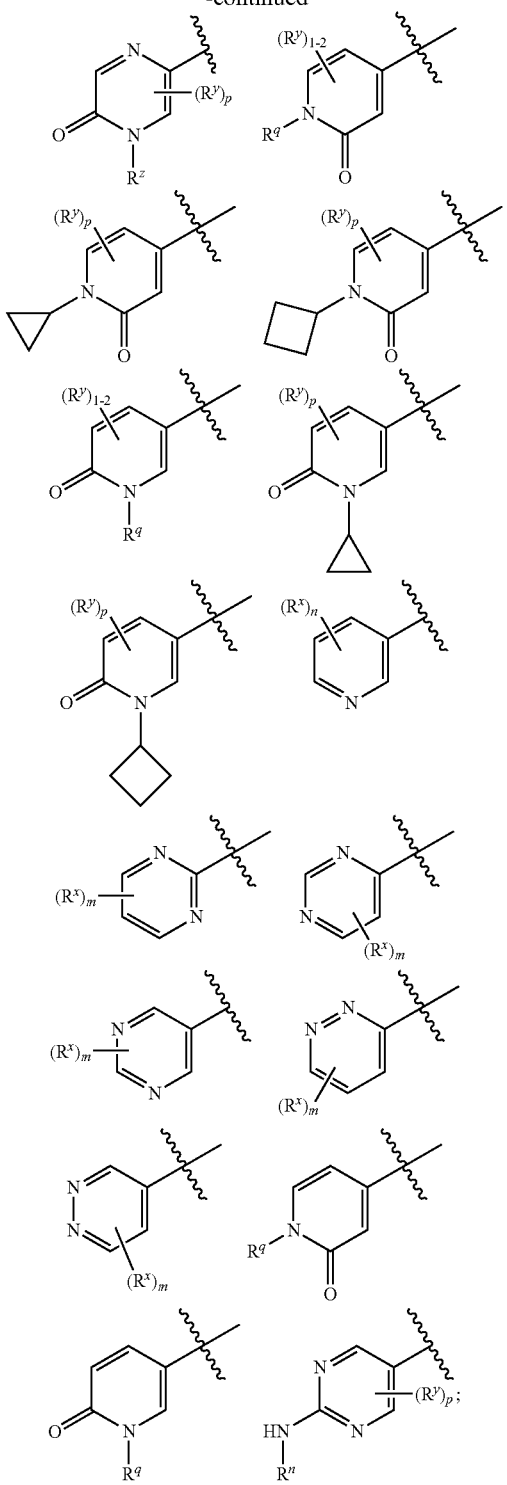

$R^m$ is (1-3C)alkyl substituted with 1-3 fluoros, or (3-4C)cycloalkyl;
$R^n$ is (1-3C)alkyl;
$R^q$ is (1-3C)alkyl optionally substituted with 1-3 fluoros;
$R^x$ is (1-6C)alkyl, halogen, CN, hydroxy(1-6C)alkyl, trifluoro(1-6C)alkyl, (3-6C)cycloalkyl, (3-6C cycloalkyl)CH$_2$—, (3-6C cycloalkyl)C(=O)—, (1-3C alkoxy)(1-6C)alkyl, (1-6C)alkoxy, (1-6C)alkylsulfonyl, NH$_2$, (1-6C alkyl)amino, di(1-6C alkyl)amino, or trifluoro(1-3C)alkoxy;

n is 0, 1, 2, 3 or 4;
m is 0, 1, 2 or 3;
$R^y$ is F or (1-3C)alkyl optionally substituted with 1-3 fluoros;
p is 0, 1 or 2;
$R^z$ is (3-4C)cycloalkyl, or (1-3C)alkyl optionally substituted with 1-3 fluoros; and
$R^5$ is H, (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylsulfanyl, phenyl [optionally substituted with one or more substituents independently selected from halogen, (1-6C)alkyl and (1-6C)alkoxy], (3-4C)cycloalkyl, amino, aminocarbonyl, or trifluoro(1-3C alkyl)amido.

In one embodiment, compounds of Formula I include compounds where $R^4$ is other than (1-6C alkyl)SO$_2$— and (1-6C alkyl)C(=O)—.

It is to be understood that in instances where two or more radicals are used in succession to define a substituent attached to a structure, the first named radical is considered to be terminal and the last named radical is considered to be attached to the structure in question. Thus, for example, the radical "alkoxyalkyl" is attached to the structure in question by the alkyl group.

The terms "(1-6C)alkyl", "(1-4C)alkyl" and "(1-3C)alkyl" as used herein refer to saturated linear monovalent hydrocarbon radicals of one to six carbon atoms, one to four carbon atoms, and one to three carbon atoms, respectively, or a branched saturated monovalent hydrocarbon radical of three to six carbon atoms, three to four carbon atoms, or three carbon atoms, respectively. Examples include, but are not limited to, methyl, ethyl, 1-propyl, 2-propyl, 1-butyl, 2-methyl-1-propyl, 2-butyl, 2-methyl-2-propyl, 2,2-dimethylpropyl, 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

"(1-6C)Alkylsulfanyl" as used herein refers to a (1-6C alkyl)S— group, wherein the radical is on the sulfur atom and the (1-6C alkyl) portion is as defined above. Examples include methylsulfanyl (CH$_3$S—) and ethylsulfanyl (CH$_2$CH$_2$S—).

"(1-4C)Alkoxy", "(1-3C)alkoxy" and "(1-6C)alkoxy" refer to an OR radical where R is (1-4C)alkyl, (1-3C)alkyl, (1-6C)alkyl, or (2-6C)alkyl, respectively, as defined above. Examples include methoxy, ethoxy, and the like.

"(1-4C Alkoxycarbonyl)(1-6C)alkyl" means a (1-6C)alkyl group as defined herein, wherein one of the carbons is substituted with a (1-4C alkoxy)carbonyl group as defined herein.

"(1-3C Alkoxy)trifluoro(1-6C)alkyl" means a (1-6C)alkyl group as defined herein, wherein one of the carbons is substituted with three fluoros, and another carbon is substituted with a (1-3C)alkoxy group as defined herein.

"(1-4C Alkoxycarbonyl)(1-3C alkoxy)(1-6C)alkyl" means a (1-3C alkoxy)(1-6C)alkyl group as defined herein wherein one of the carbon atoms is substituted with one (1-4C alkoxycarbonyl group, i.e., an alkyl-O—C(=O)— group.

"Amino" means a —NRR' group where R and R' are independently selected from hydrogen or (1-3C)alkyl as defined herein. Examples include H$_2$N—, CH$_3$NH—, (CH$_3$)$_2$N, and the like.

"Amino(1-6C)alkyl" means a linear saturated monovalent hydrocarbon radical of one to six carbon atoms or a branched saturated monovalent hydrocarbon radical of three to six carbon atoms, wherein one of the carbon atoms is substituted with one —NRR' group where R and R' are independently selected from hydrogen or (1-3C)alkyl as defined herein. Examples include aminomethyl, methylaminoethyl, 2-ethylamino-2-methylethyl, and the like.

"Aminocarbonyl" means a RR'NCO— radical where R and R' are independently hydrogen or (1-6C)alkyl as defined herein. Examples include $H_2NCO$—, dimethylaminocarbonyl, and the like.

"Aminocarbonyl(1-6C)alkyl" means a linear saturated hydrocarbon radical of one to six carbon atoms or a branched saturated monovalent hydrocarbon radical of three to six carbons wherein one of the carbon atoms is substituted with one aminocarbonyl group as defined herein, e.g., 2-aminocarbonylethyl, 1-, 2-, or 3-dimethylaminocarbonylpropyl, and the like.

"Hydroxycarbonyl" means HOC(=O)—.

"Cyano(1-6C)alkyl" means a linear saturated hydrocarbon radical of one to six carbon atoms or a branched saturated monovalent hydrocarbon radical of three to six carbons substituted with a cyano (CN) group.

"(3-6C)Cycloalkyl" means a cyclic saturated monovalent hydrocarbon radical of three to six carbon atoms, e.g., cyclopropyl, cyclobutyl, cyclopentyl, or cyclohexyl.

"Di(1-3C alkoxy)(1-6C)alkyl" means a (1-6C)alkyl group as defined herein, wherein two carbons are each substituted with one (1-3C)alkoxy group as defined herein.

"Dihydroxy(2-6C)alkyl" means a linear saturated hydrocarbon radical of two to six carbon atoms or a branched saturated monovalent hydrocarbon radical of three to six carbons substituted with two hydroxy (OH) groups, provided that two hydroxy groups are not both on the same carbon atom. "Halogen" as used herein means F, Cl, Br or I.

"Heterocycle" refers to a saturated or partially unsaturated ring system having one or more ring heteroatoms as recited for the specific heterocyclic group, wherein the heterocycle is optionally substituted with substituents as defined for that particular heterocyclic group.

"Heteroaryl" refers to a 5-6 membered unsaturated ring system having one or more ring heteroatoms as recited for the specific heteroaryl group, wherein the heteroaryl is optionally substituted with substituents as defined for that particular heteroaryl group.

"Hydroxy(1-6C)alkyl" and "hydroxy(1-4C)alkyl" means a linear saturated hydrocarbon radical of one to six carbon atoms or one to four carbon atoms, respectively, or a branched saturated monovalent hydrocarbon radical of three to six carbon atoms or three to four carbon atoms, respectively, wherein one of the carbon atoms is substituted with a hydroxy (OH) group.

"Hydroxy(1-3C alkoxy)(1-6C)alkyl" means a (1-3C alkoxy)(1-6C)alkyl group as defined herein, wherein one of the carbons is substituted with a hydroxy group.

"Monofluoro(1-6C)alkyl", "difluoro(1-6C)alkyl" and "trifluoro(1-6C)alkyl" refer to a (1-6C)alkyl group as defined herein wherein one to three hydrogen atoms, respectively, is replaced by a fluoro group.

"Tetrafluoro(2-6C)alkyl" and "pentafluoro(2-6C)alkyl" refer to a linear saturated monovalent hydrocarbon radical of two to six carbon atoms or a branched saturated monovalent hydrocarbon radical of three to six carbon atoms wherein four to five hydrogen atoms, respectively, is replaced by a fluoro group.

"(Trifluoromethoxy)(1-6C)alkyl" means a linear saturated hydrocarbon radical of one to six carbon atoms substituted with one $CF_3O$— group.

"Trifluoro(1-3C alkyl)amido" means a (1-3C alkyl)C(=O)NH— group wherein one of the carbons is substituted with three fluoros.

"Trifluoro(1-3C)alkoxy" means a (1-3C)alkoxy group as defined herein, wherein one of the carbon atoms is substituted with three fluoros.

(1-3C Sulfanyl)(1-6C)alkyl" means a linear saturated hydrocarbon radical of one to six carbon atoms substituted with one (1-3C)S— group.

It should be noted that compounds of the invention may contain groups that may exist in tautomeric forms, such as heteroatom substituted heteroaryl or heterocyclic groups and the like, which are illustrated in the following general and specific examples:

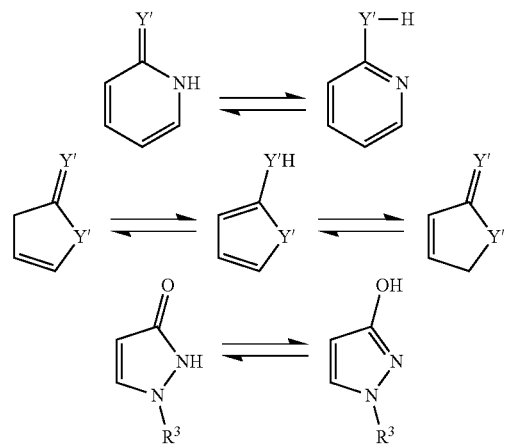

where Y'=O, S, or NR, and though one form is named, described, displayed and/or claimed herein, all the tautomeric forms are intended to be inherently included in such name, description, display and/or claim.

In one embodiment of Formula I, $R^a$, $R^b$, $R^c$ and $R^d$ are independently selected from H and methyl. In one embodiment, $R^a$, $R^b$, $R^c$ and $R^d$ are hydrogen. In one embodiment, $R^a$ is methyl and $R^b$, $R^c$ and $R^d$ are hydrogen. In one embodiment, $R^a$ and $R^b$ are methyl and $R^c$ and $R^d$ are hydrogen. In one embodiment, $R^a$, $R^b$ and $R^c$ are hydrogen and $R^d$ is methyl. In one embodiment, $R^a$ and $R^b$ are hydrogen and $R^c$ and $R^d$ are methyl.

In one embodiment, $R^c$ and $R^d$ are independently selected from H and (1-3C)alkyl, and $R^a$ and $R^b$ together with the atom to which they are attached form a cyclopropyl ring.

In one embodiment, X is O.
In one embodiment, X is S.
In one embodiment, X is NH.
In one embodiment, X is N—CN.

In one embodiment, $R^1$ is (1-3C alkoxy)(1-6C)alkyl, for example, methoxyethyl, methoxypropyl, ethoxyethyl and 2-methoxypropyl. Particular examples include 2-methoxyethyl and 2-methoxypropyl having the structures:

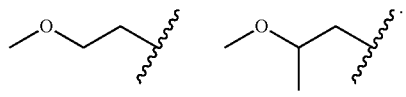

In one embodiment, R¹ is 2-methoxyethyl.

In one embodiment, R¹ is (trifluoromethoxy)(1-6C)alkyl, for example, (trifluoromethoxy)ethyl, (trifluoromethoxy)propyl, and the like. In one embodiment, R¹ is (trifluoromethoxy)ethyl.

In one embodiment, R¹ is (1-3C sulfanyl)(1-6C)alkyl, for example methylsulfanylethyl, ethylsulfanylethyl, and the like. In one embodiment, R¹ is methylsulfanylethyl.

In one embodiment, R¹ is monofluoro(1-6C)alkyl, difluoro(1-6C)alkyl or trifluoro(1-6C)alkyl. In one embodiment, R¹ is 1,3-difluoroprop-2-yl, 2,2-difluoroethyl, 4,4,4-trifluorobutyl or 2,2,2-trifluoroethyl having the structures:

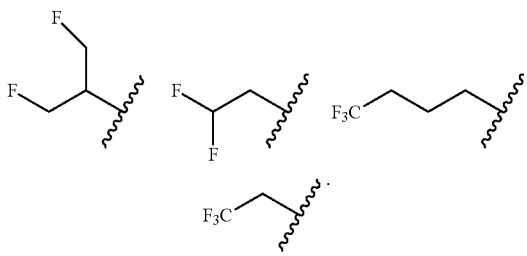

In one embodiment, R¹ is tetrafluoro(2-6C)alkyl or pentafluoro(2-6C)alkyl. In one embodiment, R¹ is 3,3,4,4,4-pentafluorobutyl.

In one embodiment, R¹ is cyano(1-6C)alkyl. In one embodiment, R¹ is 2-cyanoethyl.

In one embodiment, R¹ is aminocarbonyl(1-6C)alkyl. In one embodiment, R¹ is aminocarbonylmethyl. In one embodiment, R¹ is methylaminocarbonylmethyl having the formula MeNHC(=O)CH₂—.

In one embodiment, R¹ is hydroxy(1-6C)alkyl. In one embodiment, R¹ is 2-hydroxyethyl or 2-hydroxypropyl.

In one embodiment, R¹ is dihydroxy(2-6C)alkyl. In one embodiment, R¹ is the structure:

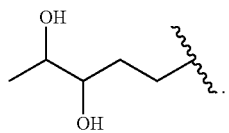 [SMILES: *CCC(O)C(C)O]

In one embodiment, R¹ is (1-6C)alkyl. In one embodiment, R¹ is methyl, ethyl, or propyl.

In one embodiment, R¹ is (1-3C alkylamino)(1-3C)alkyl, that is, a (1-3C)alkyl group which is substituted with a (1-3C alkyl)amino group, for example a (1-3C alkyl)NH— group such as methylamino. In one embodiment, R¹ is (2-methylamino)ethyl.

In one embodiment, R¹ is (1-4C alkoxycarbonyl)(1-6C)alkyl. In one embodiment, R¹ is methoxycarbonylmethyl, having the structure:

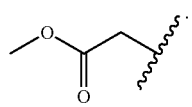 [SMILES: *CC(=O)OC]

In one embodiment, R¹ is amino(1-6C)alkyl, such as methylamino(1-6C)alkyl. In one embodiment, R¹ is 2-methylaminoethyl.

In one embodiment, R¹ is hydroxy(1-3C alkoxy)(1-6C)alkyl. Examples include hydroxymethoxy(1-6C)alkyl. In one embodiment, R¹ is selected from the structures:

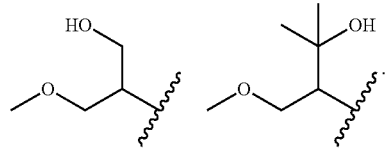

In one embodiment, R¹ is di(1-3C alkoxy)(1-6C)alkyl. Examples include dimethoxy(1-6C)alkyl. In one embodiment, R¹ is 1,3-dimethoxyprop-2-yl having the structure:

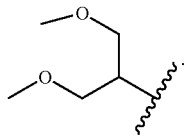 [SMILES: *C(COC)COC]

In one embodiment, R¹ is (1-3C alkoxy)trifluoro(1-6C)alkyl. Examples include methoxytrifluoro(1-6C)alkyl. In one embodiment, R¹ is 3,3,3-trifluoro-2-methoxypropyl. In one embodiment, R¹ is hydroxytrifluoro(1-6C)alkyl. In one embodiment, R¹ is 3,3,3-trifluoro-2-hydroxypropyl.

In one embodiment, R¹ is (1-4C alkoxycarbonyl)(1-3C alkoxy)(1-6C)alkyl. Examples include (methoxycarbonyl)methoxy(1-6C)alkyl. In one embodiment, R¹ is a group having the structure:

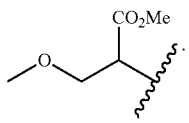 [SMILES: *C(COC)C(=O)OC]

In one embodiment, R¹ is hydroxycarbonyl(1-3C alkoxy)(1-6C)alkyl. Examples include (methoxycarbonyl)hydroxy(1-6C)alkyl. In one embodiment, R¹ is a group having the structure:

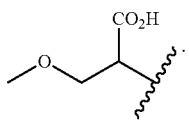 [SMILES: *C(COC)C(=O)O]

In one embodiment, R¹ is selected from (1-3C alkoxy)(1-6C)alkyl, difluoro(1-6C)alkyl and trifluoro(1-6C)alkyl.

In one embodiment, R² is H.
In one embodiment, R² is F.
In one embodiment, R² is OH.

In one embodiment of Formula I, Ring B is is Ar¹, where Ar¹ is phenyl optionally substituted with one or more substituents independently selected from halogen, CF₃, CF₃O—, (1-4C)alkoxy, hydroxy(1-4C)alkyl, (1-6C)alkyl, and CN. In one embodiment, Ar¹ is phenyl optionally substituted with one or more substituents independently selected from halogen, CF₃, (1-4C)alkoxy and CN. In one embodiment, Ar¹ is phenyl optionally substituted with one or more substituents independently selected from F, Cl, CF₃, MeO and CN.

In one embodiment, Ring B when represented by Ar¹ is selected from phenyl, 2-fluorophenyl, 3-fluorophenyl, 4-fluorophenyl, 3,4-difluorophenyl, 3,5-difluorophenyl, 2,4-difluorophenyl, 2,5-difluorophenyl, 3,4,5-trifluorophenyl, 2-chlorophenyl, 3-chlorophenyl, 4-chlorophenyl, 3-trifluoromethylphenyl 3-methoxyphenyl, 3-chloro-4-fluorophenyl, 4-chloro-3-fluorophenyl, 3-chloro-5-fluorophenyl, 3-cyano-5-fluorophenyl, 2-cyanophenyl, 4-cyanophenyl and 3-cyano-4-fluorophenyl.

In one embodiment, Ring B is is Ar¹, wherein Ar¹ is phenyl optionally substituted with one or more halogens. In one embodiment, Ar¹ is phenyl optionally substituted with one or more F or Cl. In one embodiment, Ar¹ is 3-fluorophenyl, 4-fluorophenyl, 3,4-difluorophenyl, 3,5-difluorophenyl, 3,4,5-trifluorophenyl, 3-chlorophenyl, 3-chloro-4-fluorophenyl, 3-chloro-5-fluorophenyl, or 4-chloro-3-fluorophenyl.

In one embodiment of Formula I, Ring B is hetAr¹, where hetAr¹ is a 5-6 membered heteroaryl having 1-3 ring heteroatoms independently selected from N, S and O, and is optionally substituted with one or more substituents independently selected from (1-6C)alkyl, halogen, OH, CF₃, NH₂ and hydroxy(1-2C)alkyl. In one embodiment, Ring B is hetAr¹, wherein hetAr¹ is a 5-6 membered heteroaryl having 1-2 ring heteroatoms independently selected from N, S and O, and optionally substituted with 1-2 groups independently selected from (1-6C)alkyl, halogen, OH, CF₃, NH₂ and hydroxy(1-2C)alkyl. Examples of Ring B include pyridyl, thiophenyl, thiazolyl, oxazolyl, and isoxazolyl rings optionally substituted with 1-2 groups independently selected from (1-6C)alkyl, halogen, OH, CF₃, NH₂ and hydroxy(1-2C) alkyl. In one embodiment, Ring B is a pyridyl, thiophenyl, thiazolyl, oxazolyl, or isoxazolyl ring optionally substituted with 1-2 groups independently selected from halogen and (1-6C)alkyl.

In one embodiment, Ring B when represented by hetAr¹ is selected from pyrid-4-yl, pyrid-3-yl, pyrid-2-yl, 5-fluoropyrid-3-yl, thien-2-yl, thiazol-2-yl, 2,4-dimethylthiazol-5-yl, oxazol-5-yl, isoxazol-5-yl, 5-chloropyrid-3-yl, 5-fluoropyrid-2-yl, 3-fluoropyrid-4-yl and 1-methylpyrazol-4-yl having the structures:

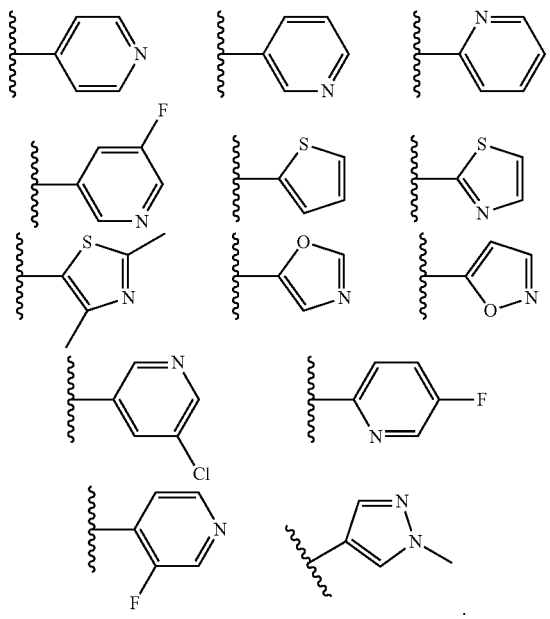

In one embodiment Ring B is a pyridyl ring optionally substituted with 1-2 groups independently selected from (1-6C)alkyl and halogen.

Reference will now be made to Ring C:

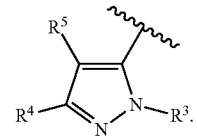

In one embodiment, R³ is H.

In one embodiment, R³ is (1-6C)alkyl. In one embodiment, R³ is methyl or ethyl.

In one embodiment, R³ is hydroxy(1-6C)alkyl. In one embodiment, R³ is 2-hydroxyethyl.

In one embodiment, R³ is Ar², where Ar² is phenyl optionally substituted with one or more substituents independently selected from halogen and (1-6C)alkyl. In one embodiment, R³ is phenyl, 2-fluorophenyl, 3-fluorophenyl, 4-fluorophenyl, 2-methylphenyl, 3-methylphenyl, 4-methylphenyl, 3-(hydroxymethyl)phenyl, 3-chlorophenyl, 3-chloro-4-fluorophenyl and 3-chloro-2-fluorophenyl. Particular examples of R³ when represented by Ar² include phenyl, 2-fluorophenyl, 3-fluorophenyl, 4-fluorophenyl, 2-methylphenyl, 3-methylphenyl and 4-methylphenyl.

In one embodiment, R³ is phenyl.

In one embodiment, R³ is hetCyc¹, where hetCyc¹ is a 5-6-membered saturated or partially unsaturated heterocyclic ring having 1-2 ring heteroatoms independently selected from N and O. In one embodiment, R³ is a pyrrolidinyl, tetrahydrofuranyl, imidazolidinyl, piperidinyl, piperazinyl, tetrahydropyranyl, or morpholinyl ring. In one embodiment, R³ is tetrahydro-2H-pyran-4-yl.

In one embodiment, R³ is (3-7C)cycloalkyl. In one embodiment R³ is cyclohexyl.

In one embodiment, R³ is hetAr², where hetAr² is 5-6 membered heteroaryl ring having 1-3 ring heteroatoms independently selected from N, O and S and optionally substituted with one or more substituents independently selected from (1-6C)alkyl and halogen. In one embodiment, R³ is a thienyl, furyl, imidazolyl, pyrazolyl, thiazolyl, isothiazolyl, oxazolyl, isoxazolyl, triazolyl, thiadiazolyl, oxadiazolyl, pyridyl, pyrimidyl, pyrazinyl, or pyridazinyl optionally substituted with one or more substituents independently selected from (1-6C)alkyl and halogen. In one embodiment, R³ is pyrazolyl, pyridyl or pyridazinyl optionally substituted with one or more substituents independently selected from (1-6C)alkyl and halogen. In one embodiment, R³ is 1-methyl-1H-pyrazol-4-yl, pyrid-2-yl, pyrid-3-yl, pyrid-4-yl, pyridazinyl or 3-chloropyrid-5-yl.

In one embodiment, R³ is a C5-C8 bridged carbocyclic ring. An example includes the structure:

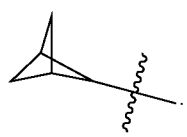 [SMILES: *C1C2CC1C2]

In one embodiment, R³ is selected from Ar², hetAr² and (1-6C)alkyl.

In one embodiment, R³ is selected from Ar² and hetAr².

In one embodiment, R³ is selected from Ar².

In one embodiment of Formula I, R⁴ is selected from (1-6C alkyl)SO₂—, (1-6C alkyl)C(=O)— and from the structures:

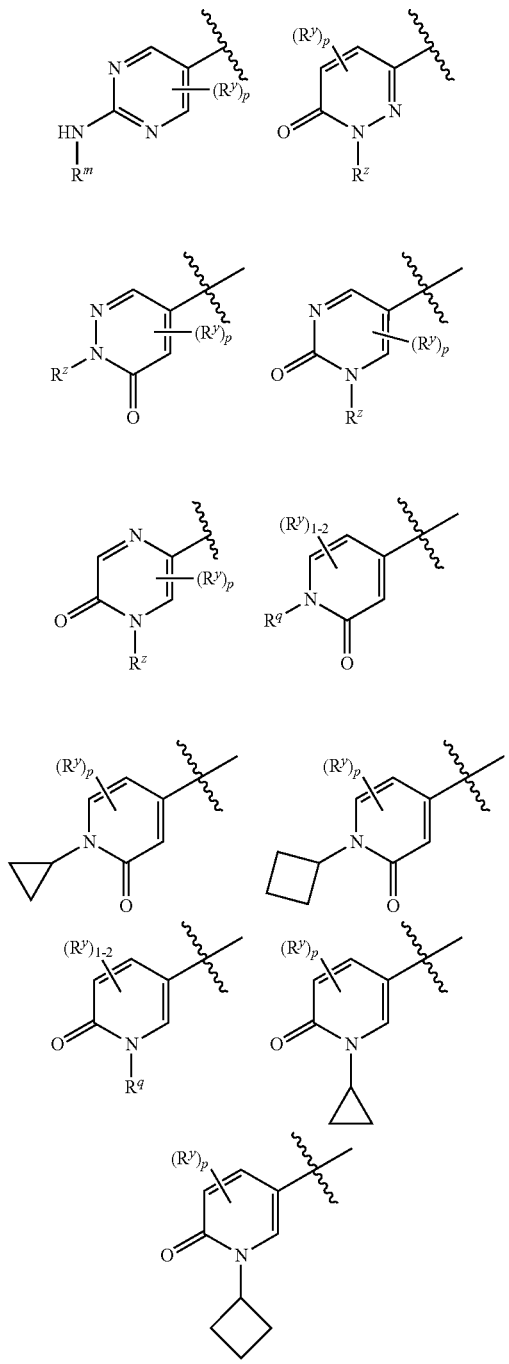
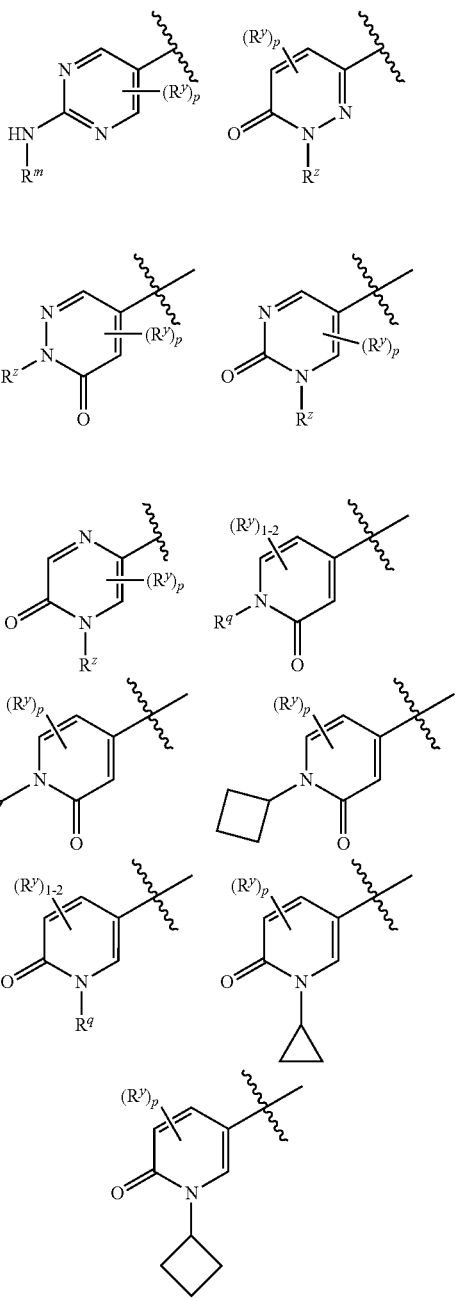

where $R^m$, $R^q$, $R^y$, $R^z$, and p are as defined for Formula I.

In one embodiment of Formula I, R⁴ is selected from (1-6C alkyl)SO₂— and (1-6C alkyl)C(=O)—.

In one embodiment of Formula I, R⁴ is (1-6C alkyl)SO₂—. In one embodiment, R⁴ is CH₃SO₂—.

In one embodiment of Formula I, R⁴ is (1-6C alkyl)C(=O)—. In one embodiment, R⁴ is CH₃C(=O)—.

In one embodiment of Formula I, R⁴ is selected from the structures:

where $R^m$, $R^q$, $R^y$, $R^z$, and p are as defined for Formula I.

In one embodiment of Formula I, R⁴ is

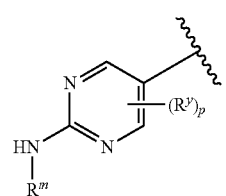

where $R^m$, $R^y$ and p are as defined for Formula I. In one embodiment, p is 0. In one embodiment, p is 1. In one embodiment, R⁴ has the structure:

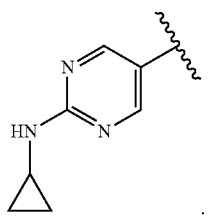 [SMILES: *c1cnc(NC2CC2)nc1]

In one embodiment of Formula I, $R^4$ is

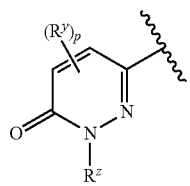

where $R^z$, $R^y$ and p are as defined for Formula I. In one embodiment, $R^z$ is (1-3C)alkyl. In one embodiment, $R^z$ is methyl. In one embodiment, $R^z$ is (1-3C)alkyl substituted with 1-3 fluoros. In one embodiment, $R^z$ is $CF_3$. In one embodiment, $R^z$ is cyclopropyl or cyclobutyl. In one embodiment, p is 0. In one embodiment, p is 1. In one embodiment, $R^4$ has the structure:

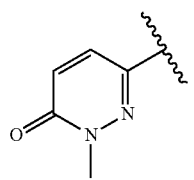

In one embodiment of Formula I, $R^4$ is

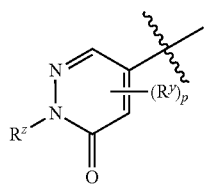

where $R^z$, $R^y$ and p are as defined for Formula I. In one embodiment, $R^z$ is (1-3C)alkyl. In one embodiment, $R^z$ is methyl. In one embodiment, $R^z$ is (1-3C)alkyl substituted with 1-3 fluoros. In one embodiment, $R^z$ is $CF_3$. In one embodiment, $R^z$ is cyclopropyl or cyclobutyl. In one embodiment, p is 0. In one embodiment, p is 1.

In one embodiment of Formula I, $R^4$ is

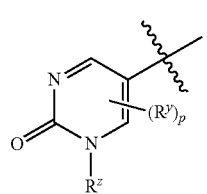

where $R^z$, $R^y$ and p are as defined for Formula I. In one embodiment, $R^z$ is (1-3C)alkyl. In one embodiment, $R^z$ is methyl. In one embodiment, $R^z$ is (1-3C)alkyl substituted with 1-3 fluoros. In one embodiment, $R^z$ is $CF_3$. In one embodiment, $R^z$ is cyclopropyl or cyclobutyl. In one embodiment, p is 0. In one embodiment, p is 1.

In one embodiment of Formula I, $R^4$ is

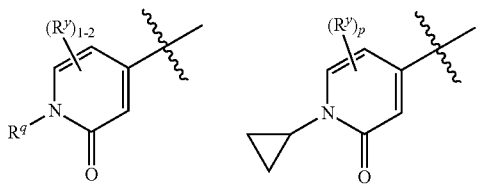

where $R^z$, $R^y$ and p are as defined for Formula I. In one embodiment, $R^z$ is (1-3C)alkyl. In one embodiment, $R^z$ is methyl. In one embodiment, $R^z$ is (1-3C)alkyl substituted with 1-3 fluoros. In one embodiment, $R^z$ is $CF_3$. In one embodiment, $R^z$ is cyclopropyl or cyclobutyl. In one embodiment, p is 0. In one embodiment, p is 1.

In one embodiment of Formula I, $R^4$ is selected from the structures:

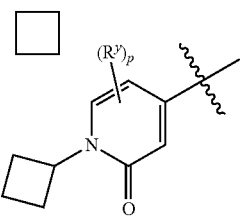

where $R^q$, $R^y$ and p are as defined for Formula I. In one embodiment, $R^q$ is (1-3C)alkyl. In one embodiment, $R^q$ is methyl. In one embodiment, $R^q$ is (1-3C)alkyl substituted with 1-3 fluoros. In one embodiment, $R^q$ is $CF_3$. In one embodiment, p is 0. In one embodiment, p is 1.

In one embodiment of Formula I, $R^4$ is selected from the structures:

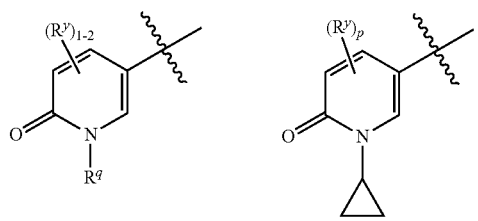

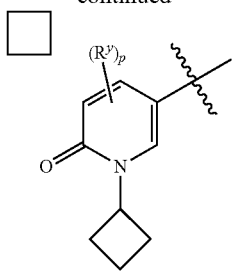

where $R^q$, $R^y$ and p are as defined for Formula I. In one embodiment, $R^q$ is (1-3C)alkyl. In one embodiment, $R^q$ is methyl. In one embodiment, $R^q$ is (1-3C)alkyl substituted with 1-3 fluoros. In one embodiment, $R^q$ is $CF_3$. In one embodiment, p is 0. In one embodiment, p is 1.

In one embodiment of Formula I, $R^4$ is selected from the structures:

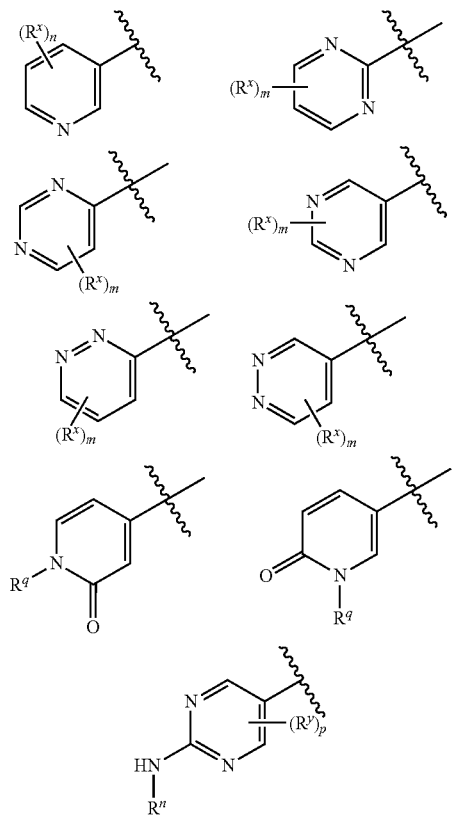

where $R^n$, $R^q$, $R^x$, Ry, n and m are as defined for Formula I.

In one embodiment, $R^q$ is (1-3C)alkyl. In one embodiment, $R^q$ is methyl. In one embodiment, $R^q$ is (1-3C)alkyl substituted with 1-3 fluoros. In one embodiment, $R^q$ is $CF_3$.

In one embodiment, $R^x$ is fluoro, methyl, ethyl, methoxy, ethoxy, cyano or cyclopropyl.

In one embodiment, n is 0 or 1.

In one embodiment, m is 0 or 1.

In one embodiment of Formula I, $R^4$ is selected from the following structures:

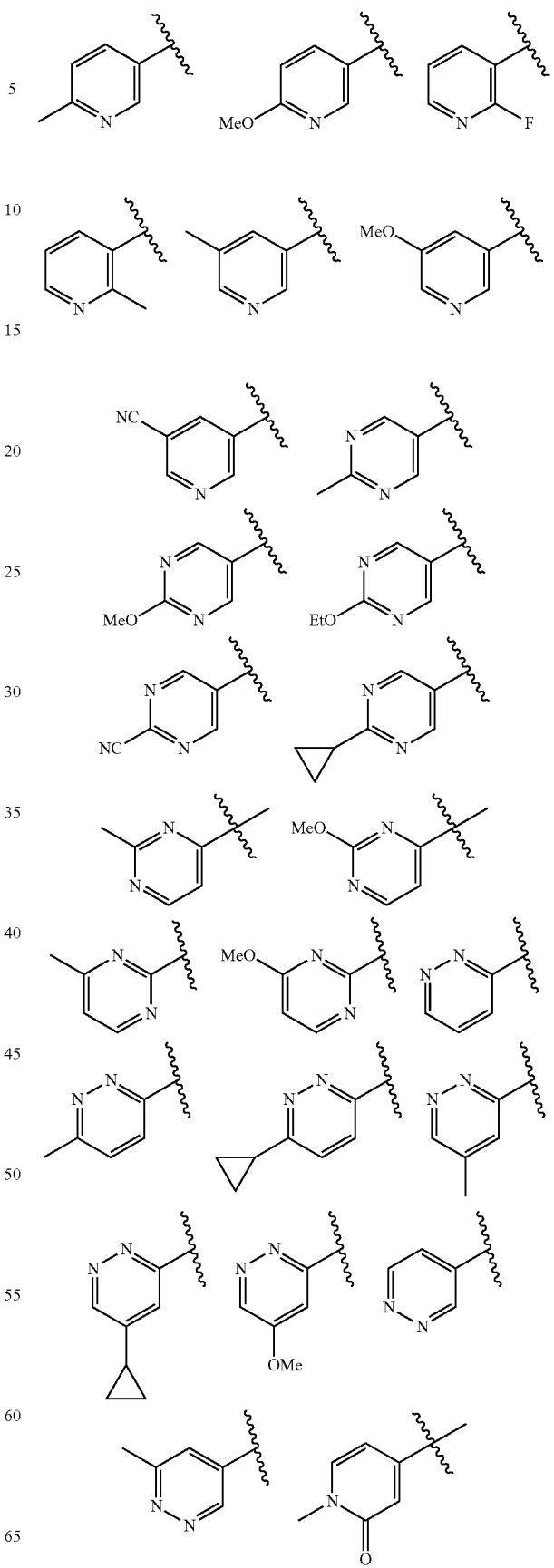

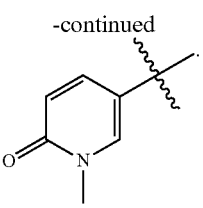

In one embodiment, R⁵ is H.

In one embodiment, R⁵ is (1-6C)alkyl. In one embodiment, R⁵ is methyl, ethyl, propyl, isopropyl or butyl. In one embodiment, R⁵ is methyl.

In one embodiment, R⁵ is monofluoro(1-6C)alkyl, difluoro(1-6C)alkyl, trifluoro(1-6C)alkyl, tetrafluro(2-6C)alkyl or pentafluro(2-6C)alkyl. In one embodiment, R⁵ is fluoromethyl, 2-fluoroethyl, difluoromethyl, 2,2-difluoroethyl, 1,3-difluoroprop-2-yl, trifluoromethyl, 2,2,2-trifluoroethyl, 3,3,3-trifluoropropyl, 1,1,2,2-tetrafluoropropyl or 2,2,3,3,3-pentafluoropropyl.

In one embodiment, R⁵ is halogen. In one embodiment, R⁵ is F. In one embodiment, R⁵ is Cl. In one embodiment, R⁵ is Br.

In one embodiment, R⁵ is CN.

In one embodiment, R⁵ is (1-4C)alkoxy. In one embodiment, R⁵ is methoxy or ethoxy.

In one embodiment, R⁵ is hydroxy(1-4C)alkyl. In one embodiment, R⁵ is hydroxymethyl or 3-hydroxypropyl.

In one embodiment, R⁵ is (1-4C alkyl)OC(=O)—. In one embodiment, R⁵ is CH₃CH₂OC(=O)—.

In one embodiment, R⁵ is (1-6C)alkylsulfanyl. In one embodiment, R⁵ is methylsulfanyl (MeS—).

In one embodiment, R⁵ is phenyl optionally substituted with one or more substituents independently selected from halogen, (1-6C)alkyl and (1-6C)alkoxy. In one embodiment, R⁵ is phenyl optionally substituted with one or more substituents independently selected from F, Cl, methyl, ethyl, methoxy and ethoxy. In one embodiment, R⁵ is phenyl.

In one embodiment, R⁵ is (3-4C)cycloalkyl. In one embodiment, R⁵ is cyclopropyl.

In one embodiment, R⁵ is cyclobutyl.

In one embodiment, R⁵ is amino. In one embodiment, R⁵ is NH₂.

In one embodiment, R⁵ is aminocarbonyl. In one embodiment, R⁵ is H₂NC(=O)—.

In one embodiment, R⁵ is trifluoro(1-3C alkyl)amido. In one embodiment, R⁵ is CF₃C(=O)NH—.

In one embodiment, R⁵ is H, halogen, CN, (1-6C)alkyl, (1-4C)alkoxy, hydroxy(1-4C)alkyl, (1-6C)alkylsulfanyl, or phenyl optionally substituted with one or more substituents independently selected from halogen, (1-6C)alkyl and (1-6C)alkoxy.

In one embodiment, R⁵ is H, halogen, CN, (1-6C)alkyl, (1-4C)alkoxy, hydroxy(1-4C)alkyl, or phenyl optionally substituted with one or more substituents independently selected from halogen, (1-6C)alkyl and (1-6C)alkoxy.

In one embodiment, R⁵ is H, halogen, or (1-6C)alkyl.

In one embodiment, R⁵ is H, methyl, Cl or Br.

In one embodiment, Formula I comprises compounds wherein:
Ring B and the NH—C(=X)—NH moiety are in the trans configuration;
$R^a$, $R^b$, $R^c$ and $R^d$ are H;
X is O;
R¹ is (1-3C alkoxy)(1-6C)alkyl;
R² is H;
Ring B is Ar¹;

Ar¹ is phenyl optionally substituted with one or more substituents independently selected from halogen, CF₃, CF₃O—, (1-4C)alkoxy, hydroxy(1-4C)alkyl, (1-6C)alkyl and CN;

Ring C is

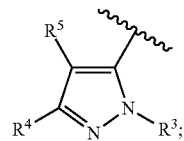

R³ is Ar²;

Ar² is phenyl optionally substituted with one or more substituents independently selected from halogen and (1-6C)alkyl;

R⁴ is selected from the structures:

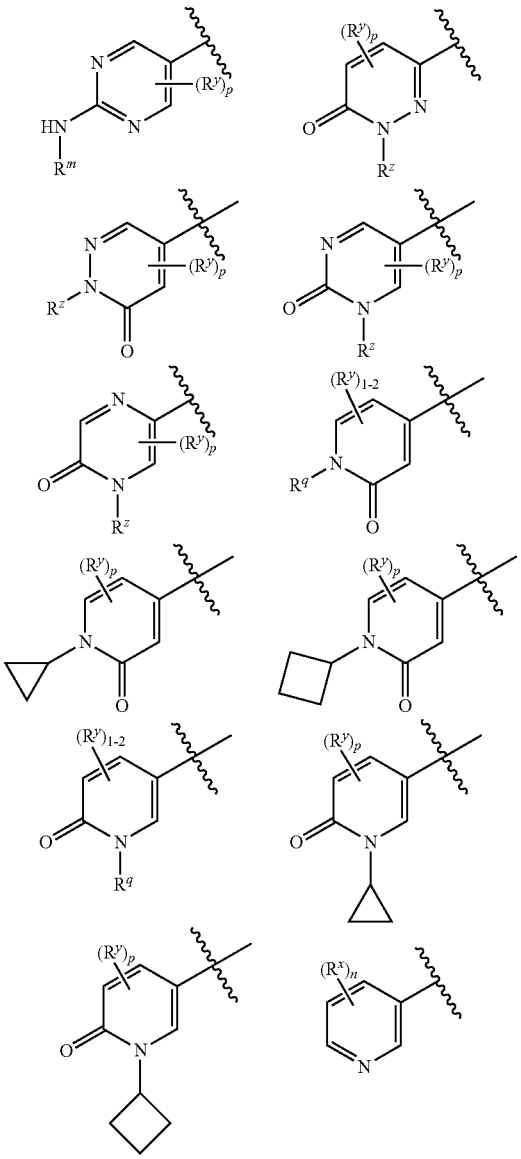

-continued

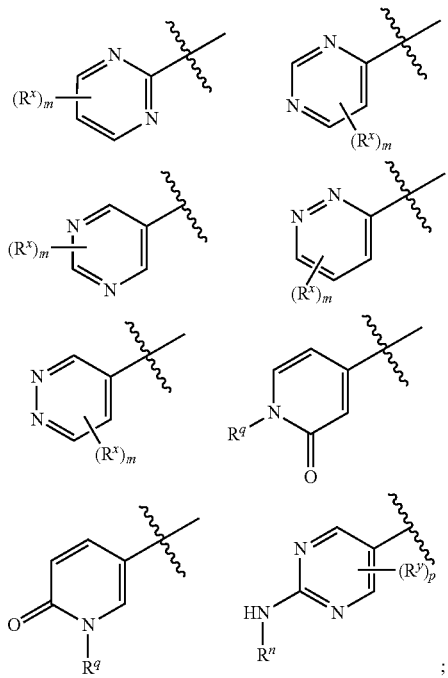

$R^m$ is (1-3C)alkyl substituted with 1-3 fluoros, or (3-4C)cycloalkyl;
$R^n$ is (1-3C)alkyl;
$R^q$ is (1-3C)alkyl optionally substituted with 1-3 fluoros;
$R^x$ is (1-6C)alkyl, halogen, CN, hydroxy(1-6C)alkyl, trifluoro(1-6C)alkyl, (3-6C)cycloalkyl, (3-6C cycloalkyl)CH$_2$—, (3-6C cycloalkyl)C(=O)—, (1-3C alkoxy)(1-6C)alkyl, (1-6C)alkoxy, (1-6C)alkylsulfonyl, NH$_2$, (1-6C alkyl)amino, di(1-6C alkyl)amino, trifluoro(1-3C)alkoxy or trifluoro(1-6C)alkyl;
n is 0, 1, 2, 3 or 4;
m is 0, 1, 2 or 3;
$R^y$ is F or (1-3C)alkyl optionally substituted with 1-3 fluoros;
p is 0, 1 or 2;
$R^z$ is (3-4C)cycloalkyl, or (1-3C)alkyl optionally substituted with 1-3 fluoros; and
$R^5$ is (1-6C)alkyl.
In one embodiment, Formula I comprises compounds wherein:
Ring B and the NH—C(=X)—NH moiety are in the trans configuration;
$R^a$, $R^b$, $R^c$ and $R^d$ are H;
X is O;
$R^1$ is (1-3C alkoxy)(1-6C)alkyl;
$R^2$ is H;
Ring B is Ar$^1$;
Ar$^1$ is phenyl optionally substituted with one or more halogens;
Ring C is formula

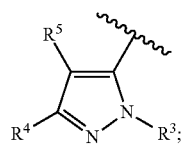

$R^3$ is phenyl;
$R^4$ is selected from the structures:

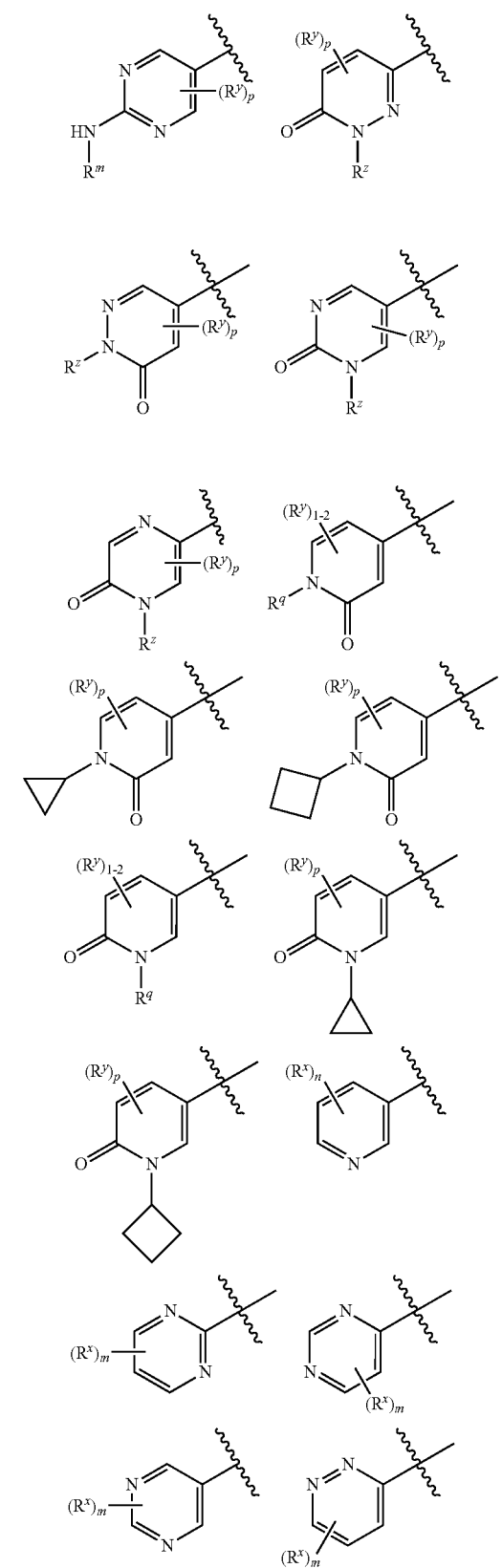

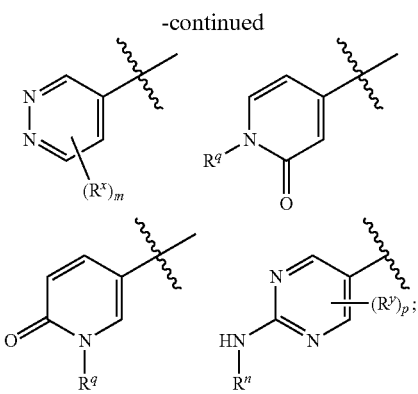

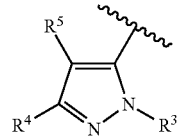

R<sup>m</sup> is (1-3C)alkyl substituted with 1-3 fluoros, or (3-4C)cycloalkyl;
R<sup>n</sup> is (1-3C)alkyl;
R<sup>q</sup> is (1-3C)alkyl optionally substituted with 1-3 fluoros;
R<sup>x</sup> is (1-6C)alkyl, halogen, CN, hydroxy(1-6C)alkyl, trifluoro(1-6C)alkyl, (3-6C)cycloalkyl, (3-6C cycloalkyl)CH$_2$— (3-6C cycloalkyl)C(=O)—, (1-3C alkoxy)(1-6C)alkyl, (1-6C)alkoxy, (1-6C)alkylsulfonyl, NH$_2$, (1-6C alkyl)amino, di(1-6C alkyl)amino, trifluoro(1-3C)alkoxy or trifluoro(1-6C)alkyl;
n is 0, 1, 2, 3 or 4;
m is 0, 1, 2 or 3;
R<sup>y</sup> is F or (1-3C)alkyl optionally substituted with 1-3 fluoros;
p is 0, 1 or 2;
R<sup>z</sup> is (3-4C)cycloalkyl, or (1-3C)alkyl optionally substituted with 1-3 fluoros; and
R<sup>5</sup> is (1-6C)alkyl.

In another embodiment of Formula I, there is provided compounds according to Formula IA, wherein:
Ring B and the NH—C(=X)—NH moiety are in the trans configuration;
R<sup>a</sup>, R<sup>b</sup>, R<sup>c</sup> and R<sup>d</sup> are independently selected from H and (1-3C)alkyl,
or R<sup>c</sup> and R<sup>d</sup> are independently selected from H and (1-3C) alkyl and R<sup>a</sup> and R<sup>b</sup> together with the atom to which they are attached form a cyclopropyl ring.
X is O, S, NH or N—CN;
R<sup>1</sup> is (1-3C alkoxy)(1-6C)alkyl, (trifluoromethoxy)(1-6C)alkyl, (1-3C sulfanyl)(1-6C)alkyl, monofluoro(1-6C)alkyl, difluoro(1-6C)alkyl, trifluoro(1-6C)alkyl, tetrafluoro(2-6C)alkyl, pentafluro(2-6C)alkyl, cyano(1-6C)alkyl, aminocarbonyl(1-6C)alkyl, hydroxy(1-6C)alkyl, dihydroxy(2-6C)alkyl, (1-6C)alkyl, (1-3 Calkylamino)(1-3C)alkyl, (1-4C alkoxycarbonyl)(1-6C)alkyl, amino(1-6C)alkyl, hydroxy(1-3C alkoxy)(1-6C)alkyl, di(1-3C alkoxy)(1-6C)alkyl, (1-3C alkoxy)trifluoro(1-6C)alkyl, hydroxytrifluoro(1-6C)alkyl, (1-4C alkoxycarbonyl)(1-3C alkoxy)(1-6C)alkyl or hydroxycarbonyl(1-3C alkoxy)(1-6C)alkyl;
R<sup>2</sup> is H, F, or OH;
Ring B is Ar<sup>1</sup> or hetAr<sup>1</sup>;
Ar<sup>1</sup> is phenyl optionally substituted with one or more substituents independently selected from halogen, CF$_3$, CF$_3$O—, (1-4C)alkoxy, hydroxy(1-4C)alkyl, (1-6C)alkyl and CN;
hetAr<sup>1</sup> is a 5-6 membered heteroaryl having 1-3 ring heteroatoms independently selected from N, S and O, and optionally substituted with one or more substituents independently selected from (1-6C)alkyl, halogen, OH, CF$_3$, NH$_2$ and hydroxy(1-2C)alkyl;

Ring C is formula C-1

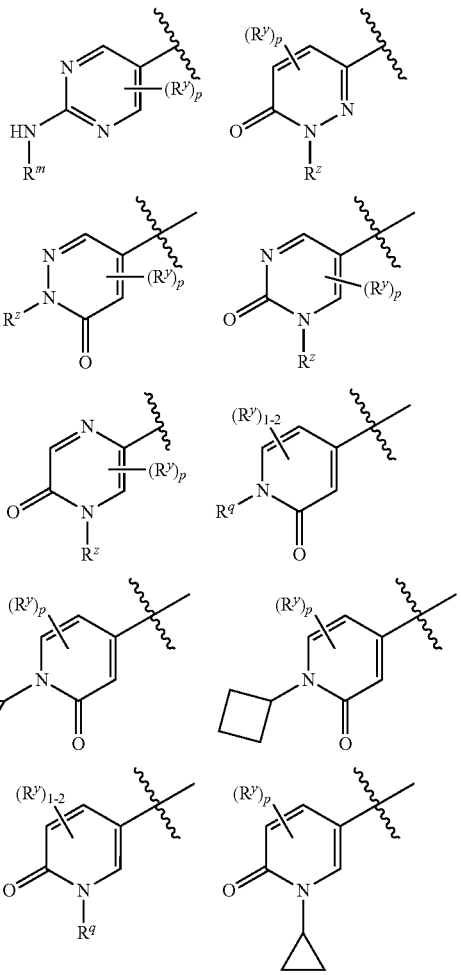

R<sup>3</sup> is H, (1-6C)alkyl, hydroxy(1-6C)alkyl, Ar<sup>2</sup>, hetCyc<sup>1</sup>, (3-7C)cycloalkyl, hetAr<sup>2</sup>, or a C5-C8 bridged carbocyclic ring;
Ar<sup>2</sup> is phenyl optionally substituted with one or more substituents independently selected from halogen and (1-6C)alkyl;
hetCyc<sup>1</sup> is a 5-6-membered saturated or partially unsaturated heterocyclic ring having 1-2 ring heteroatoms independently selected from N and O;
hetAr<sup>2</sup> is a 5-6 membered heteroaryl ring having 1-3 ring heteroatoms independently selected from N, O and S and optionally substituted with one or more substituents independently selected from (1-6C)alkyl and halogen;
R<sup>4</sup> is selected from the structures:

-continued

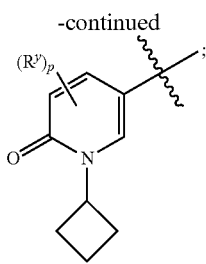

$R^m$ is (1-3C)alkyl substituted with 1-3 fluoros, or (3-4C)cycloalkyl;
$R^q$ is (1-3C)alkyl optionally substituted with 1-3 fluoros;
$R^y$ is F or (1-3C)alkyl optionally substituted with 1-3 fluoros;
p is 0, 1 or 2;
$R^z$ is (3-4C)cycloalkyl, or (1-3C)alkyl optionally substituted with 1-3 fluoros; and $R^5$ is H, (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylsulfanyl, phenyl [optionally substituted with one or more substituents independently selected from halogen, (1-6C)alkyl and (1-6C)alkoxy], (3-4C)cycloalkyl, amino, aminocarbonyl, or trifluoro(1-3C alkyl)amido.

In one embodiment of Formula IA, $R^a$, $R^b$, $R^c$ and $R^d$ are H.

In one embodiment of Formula IA, X is O.

In one embodiment of Formula IA, $R^1$ is (1-3C alkoxy)(1-6C)alkyl.

In one embodiment of Formula IA, $R^2$ is H.

In one embodiment of Formula IA, Ring B is $Ar^1$, where $Ar^1$ is phenyl optionally substituted with one or more substituents independently selected from halogen, $CF_3$, $CF_3O$—, (1-4C)alkoxy, hydroxy(1-4C)alkyl, (1-6C)alkyl and CN.

In one embodiment of Formula IA, $R^3$ is $Ar^2$, where $Ar^2$ is phenyl optionally substituted with one or more substituents independently selected from halogen and (1-6C)alkyl.

In one embodiment of Formula IA, $R^5$ is (1-6C)alkyl.

In one embodiment, compounds of Formula IA include compounds wherein:
Ring B and the NH—C(=X)—NH moiety are in the trans configuration;
$R^a$, $R^b$, $R^c$ and $R^d$ are H;
X is O;
$R^1$ is (1-3C alkoxy)(1-6C)alkyl;
$R^2$ is H;
Ring B is $Ar^1$;
$Ar^1$ is phenyl optionally substituted with one or more substituents independently selected from halogen, $CF_3$, $CF_3O$—, (1-4C)alkoxy, hydroxy(1-4C)alkyl, (1-6C)alkyl and CN;
Ring C is

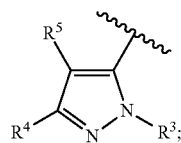

$R^3$ is $Ar^2$;
$Ar^2$ is phenyl optionally substituted with one or more substituents independently selected from halogen and (1-6C)alkyl;
$R^4$ is selected from the structures:

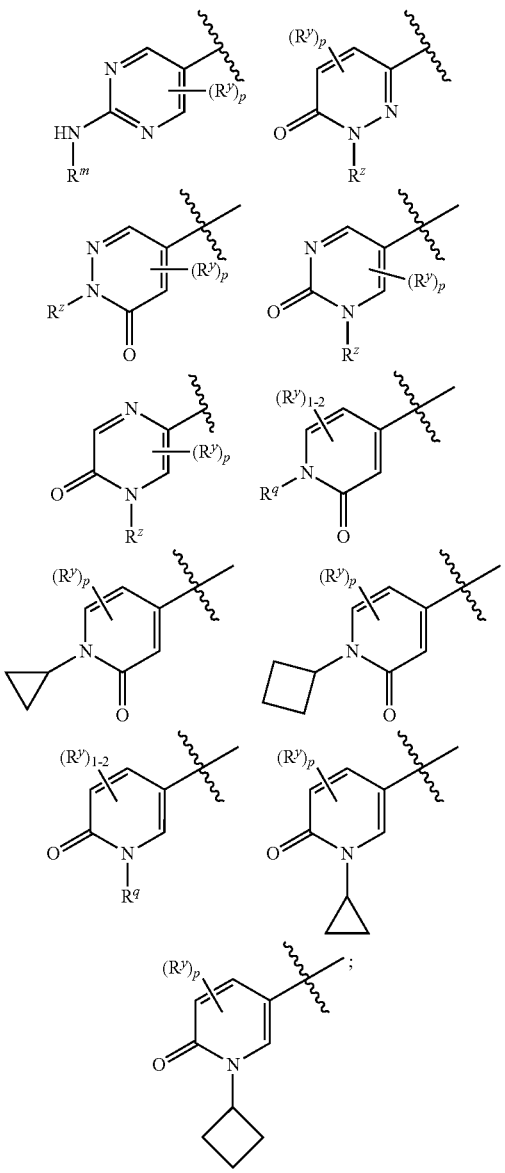

$R^m$ is (1-3C)alkyl substituted with 1-3 fluoros, or (3-4C)cycloalkyl;
$R^q$ is (1-3C)alkyl optionally substituted with 1-3 fluoros;
$R^y$ is F or (1-3C)alkyl optionally substituted with 1-3 fluoros;
p is 0, 1 or 2;
$R^z$ is (3-4C)cycloalkyl, or (1-3C)alkyl optionally substituted with 1-3 fluoros; and
$R^5$ is (1-6C)alkyl.

In one embodiment, compounds of Formula IA include compounds wherein: Ring B and the NH—C(=X)—NH moiety are in the trans configuration;
$R^a$, $R^b$, $R^c$ and $R^d$ are H;
X is O;

R¹ is (1-3C alkoxy)(1-6C)alkyl;
R² is H;
Ring B is Ar¹;
Ar¹ is phenyl optionally substituted with one or more halogens;
Ring C is

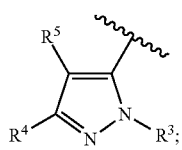

R³ is phenyl;
R⁴ is selected from the structures:

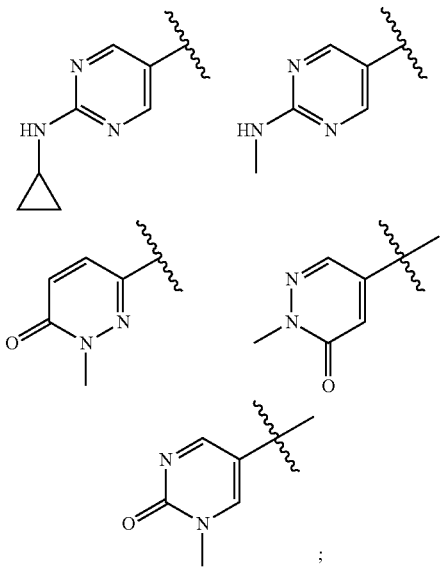

and
R⁵ is (1-6C)alkyl.

In another embodiment of Formula I, there is provided compounds according to Formula IB, wherein:
Ring B and the NH—C(=X)—NH moiety are in the trans configuration;
R$^a$, R$^b$, R$^c$ and R$^d$ are independently selected from H and (1-3C)alkyl,
or R$^c$ and R$^d$ are independently selected from H and (1-3C) alkyl and R$^a$ and R$^b$ together with the atom to which they are attached form a cyclopropyl ring.
X is O, S, NH or N—CN;
R¹ is (1-3C alkoxy)(1-6C)alkyl, (trifluoromethoxy)(1-6C) alkyl, (1-3C sulfanyl)(1-6C)alkyl, monofluoro(1-6C)alkyl, difluoro(1-6C)alkyl, trifluoro(1-6C)alkyl, tetrafluoro(2-6C) alkyl, pentafluro(2-6C)alkyl, cyano(1-6C)alkyl, aminocarbonyl(1-6C)alkyl, hydroxy(1-6C)alkyl, dihydroxy(2-6C) alkyl, (1-6C)alkyl, (1-3 Calkylamino)(1-3C)alkyl, (1-4C alkoxycarbonyl)(1-6C)alkyl, amino(1-6C)alkyl, hydroxy(1-3C alkoxy)(1-6C)alkyl, di(1-3C alkoxy)(1-6C)alkyl, (1-3C alkoxy)trifluoro(1-6C)alkyl, hydroxytrifluoro(1-6C)alkyl, (1-4C alkoxycarbonyl)(1-3C alkoxy)(1-6C)alkyl, or hydroxycarbonyl(1-3C alkoxy)(1-6C)alkyl;
R² is H, F, or OH;
Ring B is Ar¹ or hetAr¹;

Ar¹ is phenyl optionally substituted with one or more substituents independently selected from halogen, CF₃, CF₃O—, (1-4C)alkoxy, hydroxy(1-4C)alkyl, (1-6C)alkyl and CN;
hetAr¹ is a 5-6 membered heteroaryl having 1-3 ring heteroatoms independently selected from N, S and O, and optionally substituted with one or more substituents independently selected from (1-6C)alkyl, halogen, OH, CF₃, NH₂ and hydroxy(1-2C)alkyl;
Ring C is

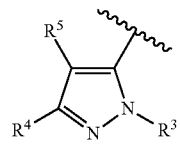

R³ is H, (1-6C)alkyl, hydroxy(1-6C)alkyl, Ar², hetCyc¹, (3-7C)cycloalkyl, hetAr², or a C5-C8 bridged carbocyclic ring;
Ar² is phenyl optionally substituted with one or more substituents independently selected from halogen and (1-6C) alkyl;
hetCyc¹ is a 5-6-membered saturated or partially unsaturated heterocyclic ring having 1-2 ring heteroatoms independently selected from N and O;
hetAr² is a 5-6 membered heteroaryl ring having 1-3 ring heteroatoms independently selected from N, O and S and optionally substituted with one or more substituents independently selected from (1-6C)alkyl and halogen;
R⁴ is selected from the structures:

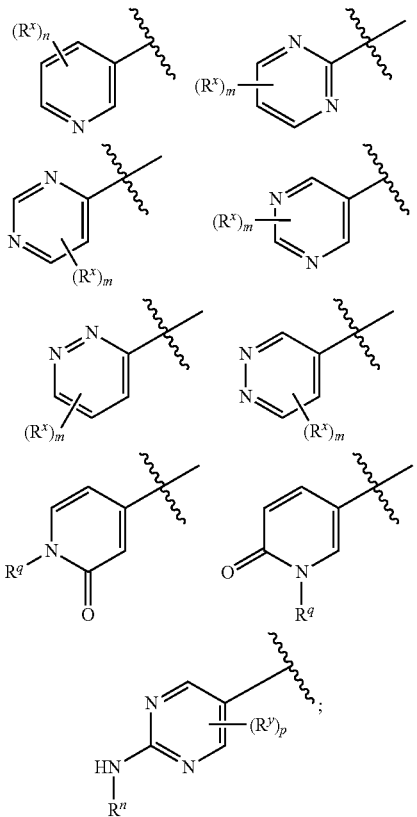

$R^n$ is (1-3C)alkyl;
$R^q$ is (1-3C)alkyl optionally substituted with 1-3 fluoros;
$R^x$ is (1-6C)alkyl, halogen, CN, hydroxy(1-6C)alkyl, trifluoro(1-6C)alkyl, (3-6C)cycloalkyl, (3-6C cycloalkyl)CH$_2$—, (3-6C cycloalkyl)C(=O)—, (1-3C alkoxy)(1-6C)alkyl, (1-6C)alkoxy, (1-6C)alkylsulfonyl, NH$_2$, (1-6C alkyl)amino, di(1-6C alkyl)amino, trifluoro(1-3C)alkoxy or trifluoro(1-6C)alkyl;
n is 0, 1, 2, 3 or 4;
m is 0, 1, 2 or 3;
$R^y$ is F or (1-3C)alkyl optionally substituted with 1-3 fluoros;
p is 0, 1 or 2; and
$R^5$ is H, (1-6C)alkyl, monofluoro(1-6C)alkyl, difluoro(1-6C)alkyl, trifluoro(1-6C)alkyl, tetrafluoro(2-6C)alkyl, pentafluoro(2-6C)alkyl, halogen, CN, (1-4C)alkoxy, hydroxy(1-4C)alkyl, (1-3C alkoxy)(1-4C)alkyl, (1-4C alkyl)OC(=O)—, (1-6C)alkylsulfanyl, phenyl [optionally substituted with one or more substituents independently selected from halogen, (1-6C)alkyl and (1-6C)alkoxy], (3-4C)cycloalkyl, amino, aminocarbonyl, or trifluoro(1-3C alkyl)amido.

In one embodiment of Formula IB, $R^a$, $R^b$, $R^c$ and $R^d$ are H.

In one embodiment of Formula IB, X is O.

In one embodiment of Formula IB, $R^1$ is (1-3C alkoxy)(1-6C)alkyl.

In one embodiment of Formula IB, $R^2$ is H.

In one embodiment of Formula IB, Ring B is Ar$^1$, where Ar$^1$ is phenyl optionally substituted with one or more substituents independently selected from halogen, CF$_3$, CF$_3$O—, (1-4C)alkoxy, hydroxy(1-4C)alkyl, (1-6C)alkyl and CN.

In one embodiment of Formula IB, $R^3$ is Ar$^2$, where Ar$^2$ is phenyl optionally substituted with one or more substituents independently selected from halogen and (1-6C)alkyl.

In one embodiment of Formula IB, $R^5$ is (1-6C)alkyl.

In one embodiment of Formula IB, $R^x$ is selected from halogen, (1-6C)alkyl, (1-6C)alkoxy, CN and cyclopropyl.

In one embodiment of Formula IB, n is 0 or 1.

In one embodiment of Formula IB, n is 0 or 1.

In one embodiment, compounds of Formula IB include compounds wherein: Ring B and the NH—C(=X)—NH moiety are in the trans configuration;
$R^a$, $R^b$, $R^c$ and $R^d$ are H;
X is O;
$R^1$ is (1-3C alkoxy)(1-6C)alkyl;
$R^2$ is H;
Ring B is Ar$^1$;
Ar$^1$ is phenyl optionally substituted with one or more substituents independently selected from halogen, CF$_3$, CF$_3$O—, (1-4C)alkoxy, hydroxy(1-4C)alkyl, (1-6C)alkyl and CN;
Ring C is

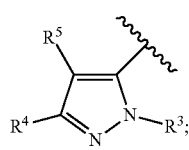

$R^3$ is Ar$^e$;
Ar$^2$ is phenyl optionally substituted with one or more substituents independently selected from halogen and (1-6C) alkyl;

$R^4$ is selected from the structures:

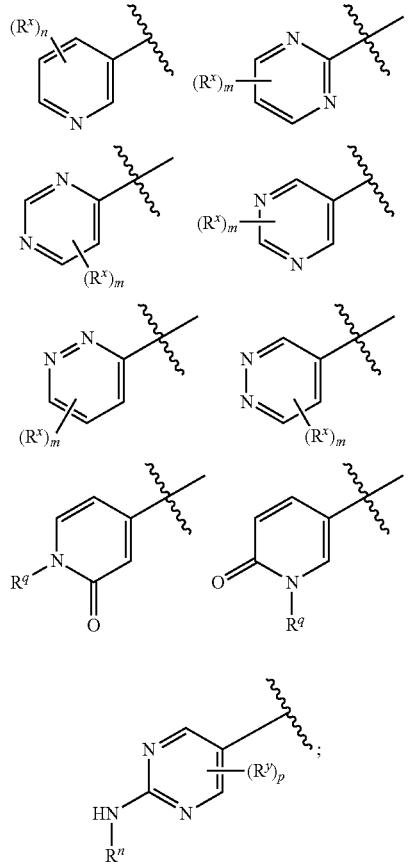

$R^q$ is (1-3C)alkyl optionally substituted with 1-3 fluoros;
$R^x$ is (1-6C)alkyl, halogen, CN, hydroxy(1-6C)alkyl, trifluoro(1-6C)alkyl, (3-6C)cycloalkyl, (3-6C cycloalkyl)CH$_2$— (3-6C cycloalkyl)C(=O)—, (1-3C alkoxy)(1-6C)alkyl, (1-6C)alkoxy, (1-6C)alkylsulfonyl, NH$_2$, (1-6C alkyl)amino, di(1-6C alkyl)amino, trifluoro(1-3C)alkoxy or trifluoro(1-6C)alkyl;
n is 0, 1, 2, 3 or 4;
m is 0, 1, 2 or 3;
$R^y$ is F or (1-3C)alkyl optionally substituted with 1-3 fluoros;
p is 0, 1 or 2; and
$R^5$ is (1-6C)alkyl.

In one embodiment, compounds of Formula IB include compounds wherein:
Ring B and the NH—C(=X)—NH moiety are in the trans configuration;
$R^a$, $R^b$, $R^c$ and $R^d$ are H;
X is O;
$R^1$ is (1-3C alkoxy)(1-6C)alkyl;
$R^2$ is H;
Ring B is Ar$^1$;
Ar$^1$ is phenyl optionally substituted with one or more halogens;

Ring C is

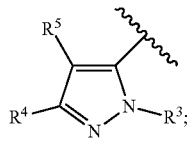

$R^3$ is phenyl;
$R^4$ is selected from the structures:

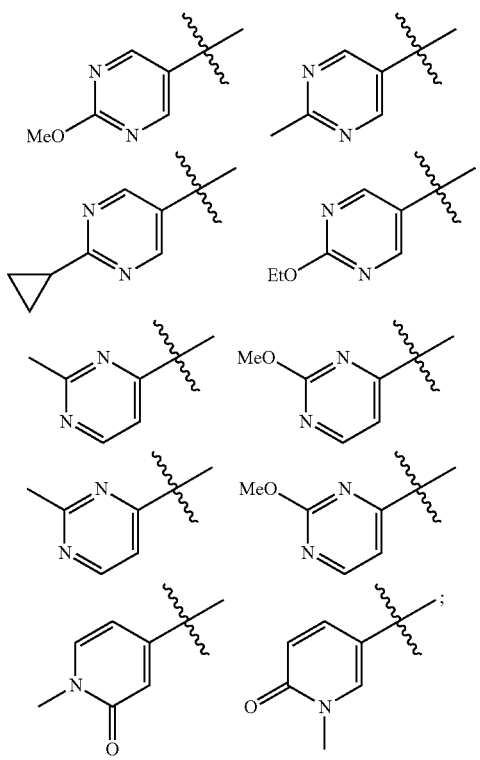

and
$R^5$ is (1-6C)alkyl.

As noted, Ring B and the —NH—C(=X)—NH— moiety of Formulas I, IA and IB are in trans configuration on the pyrrolidine ring, which relative stereochemistry can be illustrated by generic structure A and structure B:

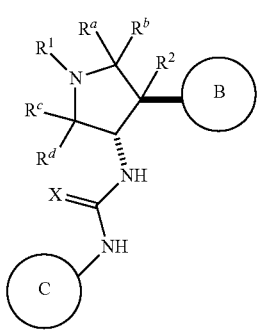

Structure A

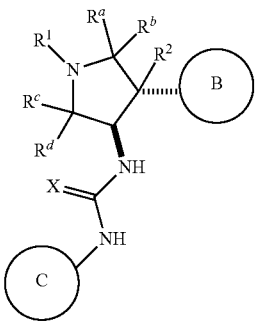

Structure B in which the straight thick bars (━) and straight dashed bars (⫶⫶⫶⫶) indicate relative stereochemistry.

In one embodiment of Formulas I, IA and IB, Ring B and the —NH—C(=X)—NH— moiety are trans in the absolute configuration which can be illustrated by generic structures C and D:

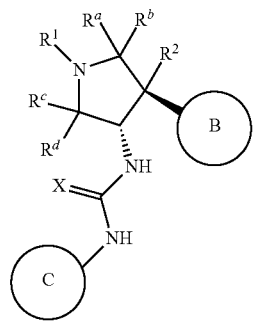

Structure C

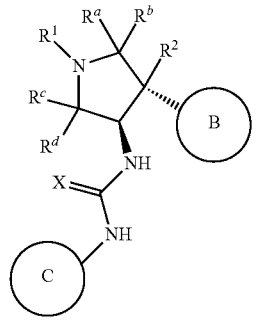

Structure D in which the solid wedges (━) and dashed wedges (⫶⫶⫶⫶) indicate absolute stereochemistry.

It will be appreciated that certain compounds according to the invention may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention. For example, compounds of Formula I can exist in unsolvated as well as solvated forms with pharmaceutically acceptable solvents such as water, ethanol, and the like.

The compounds of Formula I include pharmaceutically acceptable salts thereof. In addition, the compounds of Formula I also include other salts of such compounds which are not necessarily pharmaceutically acceptable salts, and which are useful as intermediates for preparing and/or purifying compounds of Formula I and/or for separating enantiomers of compounds of Formula I. Particular examples of salts include hydrochloride salts and trifluoroacetate salts.

In one embodiment, the compounds of Formula I include the free base form of compounds of Examples 1-31, or pharmaceutically acceptable salts thereof.

In one embodiment, the compounds of Formula I include the hydrochloride salts of compounds of Examples 1-31.

In one embodiment, the compounds of Formula I include the trifluoroacetate salts of compounds of Examples 1-31.

The term "pharmaceutically acceptable" indicates that the substance or composition is compatible chemically and/or toxicologically, with the other ingredients comprising a formulation, and/or the mammal being treated therewith.

The present invention also provides a process for the preparation of a compound of Formula I or a salt thereof as defined herein, which comprises:

(a) for a compound of Formula I where X is O, coupling a corresponding compound having the formula II

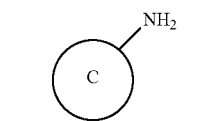

II with a corresponding compound having the formula III

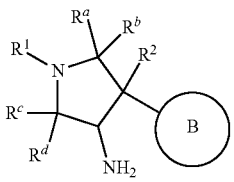

III in the presence carbonyldiimidazole or triphosgene and a base; or (b) for a compound of Formula I where X is S, coupling a corresponding compound having the formula II

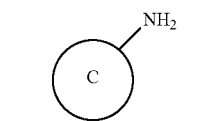

II with a corresponding compound having the formula III

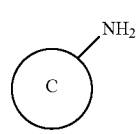

III in the presence di(1H-imidazol-2-yl)methanethione and a base; or (c) for a compound of Formula I where X is O, coupling a corresponding compound having the formula II

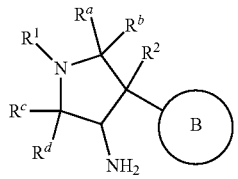

II with a corresponding compound having the formula IV

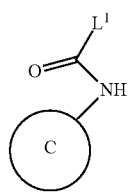

IV where $L^1$ is a leaving group, in the presence of a base; or (d) for a compound of Formula I where X is O, coupling a corresponding compound having the formula V

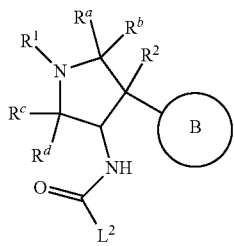

V where $L^2$ is a leaving group, with a corresponding compound having the formula III

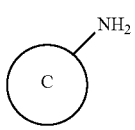

III in the presence of a base; or (e) for a compound of Formula I where X is O, activating a corresponding compound having the formula VI

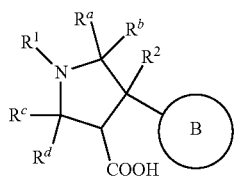

VI with diphenylphosphoryl azide followed by coupling the activated intermediate with a corresponding compound having the formula III

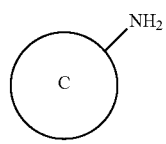

III in the presence a base; or (f) for a compound of Formula I where X is O, coupling a corresponding compound having the formula II

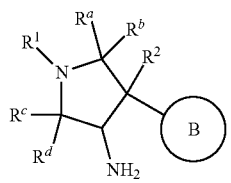

II with a corresponding compound having the formula VII

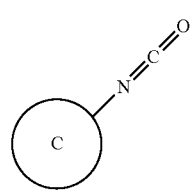

VII in the presence of a base; or (g) for a compound of Formula I where X is O, coupling a corresponding compound having the formula VIII

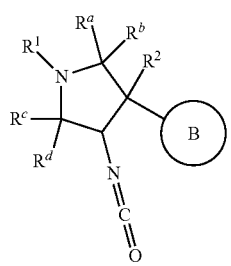

VIII with a corresponding compound having the formula III

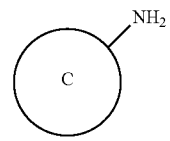

III in the presence of a base; or (h) for a compound of Formula I where $R^1$ is (trifluoromethoxy)(1-6C)alkyl, (1-3C sulfanyl)(1-6C)alkyl, monofluoro(1-6C)alkyl, difluoro(1-6C)alkyl, trifluoro(1-6C)alkyl, tetrafluoro(2-6C)alkyl, or pentafluoro(2-6C)alkyl, reacting a corresponding compound having the formula IX

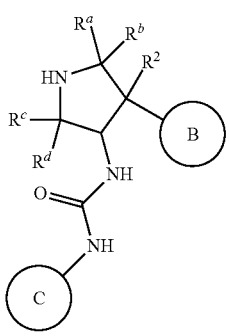

IX with a corresponding compound having the (trifluoromethoxy)(1-6C)alkyl-$L^3$, (1-3C sulfanyl)(1-6C)alkyl-$L^3$, monofluoro(1-6C)alkyl-$L^3$, difluoro(1-6C)alkyl-$L^3$, trifluoro(1-6C)alkyl-$L^3$, tetrafluoro(2-6C)alkyl-$L^3$, or pentafluoro(2-6C)alkyl-$L^3$, where $L^3$ is a leaving atom or a leaving group, in the presence of a base; or (i) reacting a compound having the formula X:

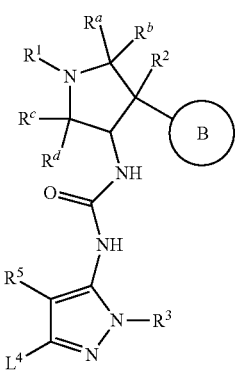

X where $L^4$ is Br or OTf, and $R^1$, $R^a$, $R^b$, $C^c$, $R^d$, $R^2$, $R^3$ and $R^5$ are as defined for Formula I, provided that $R^5$ is not halogen, with a corresponding boronic ester or boronic acid having the formula:

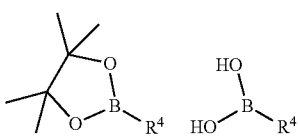

respectively, in the presence of a palladium catalyst and a base; and optionally removing protecting groups and optionally preparing a pharmaceutically acceptable salt thereof.

In the above methods, the term "corresponding" means that the definitions for the "corresponding compound" are as defined for Formula I unless stated otherwise.

Referring to method (a), the base may be an amine base, such as triethylamine or diisopropylethylamine. Suitable solvents include dichloromethane, dichloroethane, THF, DMA and DMF. The reaction is conveniently performed at ambient temperature.

Referring to method (b), the base may be an amine base, such as triethylamine or diisopropylethylamine. Suitable solvents include dichloromethane, dichloroethane, THF, DMA and DMF. The reaction is conveniently performed at ambient temperature.

Referring to method (c), the leaving group may be, for example, phenoxy or 4-nitrophenoxy. The base may be an amine base, such as triethylamine or diisopropylethylamine. Suitable solvents include DMA, DMF and DCE. The reaction is conveniently performed at ambient temperature.

Referring to method (d), the leaving group may be, for example, phenoxy or 4-nitrophenoxy. The base may be an amine base, such as triethylamine or diisopropylethylamine. Suitable solvents include DCE, DMA and DMF. The reaction is conveniently performed at ambient temperature.

Referring to method (e), the base may be an amine base, such as triethylamine or diisopropylethylamine. Suitable solvents include toluene and DMF. The reaction is conveniently performed at elevated temperatures, for example the reflux temperature of the solvent.

Referring to method (f), the base may be an amine base, such as triethylamine or diisopropylethylamine. Suitable solvents include DCM, DCE, DMF and THF. The reaction is conveniently performed at temperatures between about 0° C. and ambient temperature.

A compound of Formula VII may be prepared by reacting a compound of Formula III with bis(trichloromethyl) carbonate in the presence of a base, such as an amine base.

Referring to method (h), the base may be an amine base, such as triethylamine or diisopropylethylamine. Suitable solvents include DMF, DMA and THF. The reaction is conveniently performed at temperatures between ambient temperature and 60° C.

Referring to method (i), the reaction is conveniently performed in the presence of a ligand, such as $PPh_3$ or tricyclohexylphosphine. Suitable palladium catalysts include $Pd_2dba_3$ or $Pd(PPh_3)_4$. Suitable bases include an alkali metal carbonate, such as sodium carbonate, potassium carbonate, cesium carbonate, or potassium phosphate. Examples of suitable solvents include dioxane, toluene, or DME. The reaction is conveniently performed at temperatures between 80-110° C.

Amine groups in compounds described in any of the above methods may be protected with any convenient amine protecting group, for example as described in Greene & Wuts, eds., "Protecting Groups in Organic Synthesis", $2^{nd}$ ed. New York; John Wiley & Sons, Inc., 1991. Examples of amine protecting groups include acyl and alkoxycarbonyl groups, such as t-butoxycarbonyl (BOC) and [2-(trimethylsilyl)ethoxy]methyl (SEM). Likewise, carboxyl groups may be protected with any convenient carboxyl protecting group, for example as described in Greene & Wuts, eds., "Protecting Groups in Organic Synthesis", $2^{nd}$ ed. New York; John Wiley & Sons, Inc., 1991. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", $2^{nd}$ ed. New York; John Wiley & Sons, Inc., 1991. Examples of alcohol protecting groups include benzyl, trityl, silyl ethers, and the like.

The compounds of the formulas II, III, III, IV, V, VI, VII and VIII are provided as further aspects of the invention. In one embodiment, The compounds of the formulas II, III, III, IV, V, VI, VII and VIII are useful as intermediates for the synthesis of compounds of Formula I.

In one embodiment of the above-described processes (a), (b), (c), and (f), where ring B is $Ar^1$ and $R^a$, $R^b$, $R^d$ and $R^2$ are hydrogen, a single enantiomer of intermediate II, namely enantiomer 1 of II-A is prepared by chiral crystallization prior to use. Accordingly, in one embodiment, a process for preparing enantiomer 1 of II-A comprises:

preparing racemic trans II-A

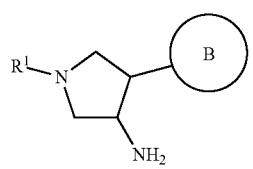

II-A where Ring B and the $NH_2$ group are in the trans configuration; Ring B is $Ar^1$ or $hetAr^1$; $Ar^1$ is phenyl optionally substituted with one or more substituents independently selected from halogen, $CF_3$, $CF_3O$—, (1-4C)alkoxy, hydroxy(1-4C)alkyl, (1-6C)alkyl and CN; and $hetAr^1$ is a 5-6 membered heteroaryl having 1-3 ring heteroatoms independently selected from N, S and O, and optionally substituted with 1-2 groups independently selected from (1-6C) alkyl, halogen, OH, $CF_3$, $NH_2$ and hydroxy(1-2C)alkyl; said method comprising:

treating racemic trans II-A with di-p-toluoyl-D-tartaric acid to provide the di-p-toluoyl-D-tartaric acid salt of racemic trans II-A;

recrystallizing the di-p-toluoyl-D-tartaric acid salt of trans II-A to provide the di-p-toluoyl-D-tartaric acid salt of enantiomer 1 of trans II-A; and treating the di-p-toluoyl-D-tartaric acid salt of enantiomer 1 of trans II-A with an inorganic base to provide free base of enantiomer 1 of trans II-A having the absolute configuration as illustrated:

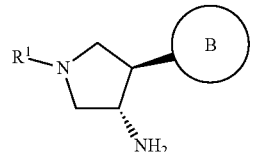

enantiomer 1 of II-A

In one embodiment of enantiomer 1 of trans II-A, $R^1$ is 2-methoxyethoxy and Ring B is 4-fluorophenyl, and racemic trans II-A is prepared by the process comprising: reacting 4-fluorobenzaldehyde with nitromethane in the presence of acetic acid and ammonium acetate to provide (E)-1-fluoro-4-(2-nitrovinyl)benzene

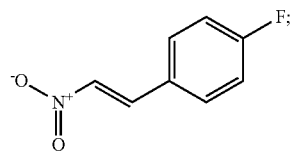

reacting (E)-1-fluoro-4-(2-nitrovinyl)benzene with 2-methoxy-N-(methoxymethyl)-N-((trimethylsilyl)methyl) ethanamine in the presence of a catalytic amount of an acid (such as TFA) to provide trans-3-(4-fluorophenyl)-1-(2-methoxyethyl)-4-nitropyrrolidine

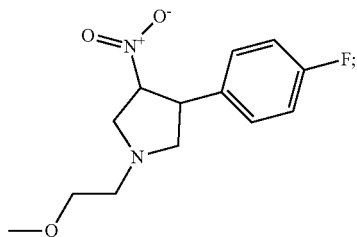 [SMILES: COCCN1CC(c2ccc(F)cc2)C([N+](=O)[O-])C1]

and
treating trans-3-(4-fluorophenyl)-1-(2-methoxyethyl)-4-nitropyrrolidine with platinum (IV) oxide or Raney Nickel in a hydrogen atmosphere to provide trans-4-(4-fluorophenyl)-1-(2-methoxyethyl)pyrrolidin-3-amine

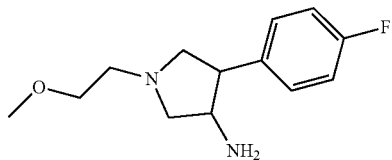 [SMILES: COCCN1CC(N)C(c2ccc(F)cc2)C1]

wherein the 4-fluorophenyl and amino group are in the trans configuration.

In one embodiment of enantiomer 1 of trans II-A, $R^1$ is 2-methoxyethoxy and Ring B is 3,4-difluorophenyl.

In one embodiment, the inorganic base is an alkali metal hydroxide such as sodium hydroxide.

A similar process as above may be used utilizing di-p-toluoyl-L-tartaric acid to provide enantiomer 2 of II-A:

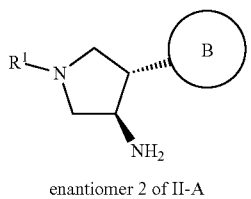

enantiomer 2 of II-A where $R^1$ and Ring B are as defined herein. In one embodiment of enantiomer 2 of trans II-A, $R^1$ is 2-methoxyethoxy and Ring B is 4-fluorophenyl. In one embodiment of enantiomer 2 of trans II-A, $R^1$ is 2-methoxyethoxy and Ring B is 3,4-difluorophenyl.

The ability of compounds of the invention to act as TrkA inhibitors may be demonstrated by the assay described in Example A.

Compounds of Formula I are useful in the treatment of pain, cancer, inflammation/inflammatory diseases, neurodegenerative diseases, certain infectious diseases, Sjogren's syndrome, endometriosis, diabetic peripheral neuropathy, prostatitis or pelvic pain syndrome.

In one embodiment, compounds of Formula I are useful for treating pain, including chronic and acute pain. For example, compounds of Formula I are useful in the treatment of multiple types of pain including inflammatory pain, neuropathic pain, and pain associated with cancer, surgery or bone fracture.

In one embodiment, compounds of Formula I are useful for treating acute pain. Acute pain, as defined by the International Association for the Study of Pain, results from disease, inflammation, or injury to tissues. This type of pain generally comes on suddenly, for example, after trauma or surgery, and may be accompanied by anxiety or stress, and is confined to a given period of time and severity. In some instances, it can become chronic.

In one embodiment, compounds of Formula I are useful for treating chronic pain. Chronic pain, as defined by the International Association for the Study of Pain, is widely believed to represent a disease in itself. It can be made much worse by environmental and psychological factors. Chronic pain persists over a longer period than acute pain and is resistant to most medical treatments, generally over 3 months or more. It can and often does cause severe problems for patients.

Compounds of Formula I are also useful for treating cancer. Particular examples include neuroblastoma, ovarian, pancreatic, colorectal and prostate cancer.

Compounds of Formula I are also useful for treating inflammation and certain infectious diseases. For example, compounds of Formula I may be used to treat interstitial cystitis (IC), painful bladder syndrome (PBS), urinary incontinence, asthma, atopic dermatitis, and psoriasis.

Compounds of Formula I are also useful for treating a neurodegenerative disease in a mammal, comprising administering to said mammal one or more compounds of Formula I or a pharmaceutically acceptable salt thereof in an amount effective to treat said neurodegenerative disease. In one embodiment, compounds of Formula I may also be used to treat demyelination and dysmyelination by promoting myelination, neuronal survival, and oligodendrocyte differentiation via blocking Sp35-TrkA interaction. In one embodiment, the neurodegenerative disease is multiple sclerosis. In one embodiment, the neurodegenerative disease is Parkinson's disease. In one embodiment, the neurodegenerative disease is Alzheimer's disease.

Compounds of Formula I are also useful for treating certain infectious diseases such as *Trypanosoma cruzi* infection in a mammal.

Compounds of Formula I are also useful for treating Sjogren's syndrome in a mammal.

Compounds of Formula I are also useful for treating endometriosis in a mammal.

Compounds of Formula I are also useful for treating diabetic peripheral neuropathy in a mammal.

Compounds of Formula I are also useful for treating prostatitis in a mammal.

Compounds of Formula I are also useful for treating pelvic pain syndrome in a mammal.

Compounds of Formula I are also useful in treating diseases related to an imbalance of the regulation of bone remodeling, such as osteoporosis, rheumatoid arthritis, and bone metastases.

As used herein, terms "treat" or "treatment" refer to therapeutic or palliative measures. Beneficial or desired clinical results include, but are not limited to, alleviation, in whole or in part, of symptoms associated with a disorder or condition, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment.

In certain embodiments, compounds of Formula I are useful for preventing diseases and disorders as defined herein. The term "preventing" as used herein means the prevention of the onset, recurrence or spread, in whole or in part, of the disease or condition as described herein, or a symptom thereof, and includes to the administration of a compound of Formula I prior to the onset of symptoms.

Accordingly, one embodiment of this invention provides a method of treating pain in a mammal, comprising administering to said mammal in need thereof one or more compounds of Formula I or a pharmaceutically acceptable salt thereof in an amount effective to treat said pain. In one embodiment, the pain is chronic pain. In one embodiment, the pain is acute pain. In one embodiment, the pain is inflammatory pain, neuropathic pain, or pain associated with cancer, surgery, or bone fracture.

Another embodiment of this invention provides a method of preventing pain in a mammal, comprising administering to said mammal in need thereof one or more compounds of Formula I or a pharmaceutically acceptable salt thereof in an amount effective to prevent said pain. In one embodiment, the pain is chronic pain. In one embodiment, the pain is acute pain. In one embodiment, the pain is inflammatory pain, neuropathic pain, or pain associated with cancer, surgery, or bone fracture.

Another embodiment of this invention provides a method of treating cancer in a mammal, comprising administering to said mammal in need thereof one or more compounds of Formula I or a pharmaceutically acceptable salt thereof in an amount effective to treat said cancer. In one embodiment, provided herein is a method for treating a patient diagnosed with a cancer having a dysregulation of TrkA, comprising administering to the patient a therapeutically effective amount of a compound of the invention or a pharmaceutically acceptable salt thereof.

In one embodiment, the dysregulation of TrkA comprises overexpression of wild-type TrkA (autocrine activation).

In one embodiment, the dysregulation of TrkA comprises one or more chromosome translocations or inversions resulting in TrkA gene fusions. In one embodiment, the dysregulation is a result of genetic translocations in which the expressed protein is a fusion protein containing residues from non-TrkA and TrkA proteins, and at a minimum the TrkA kinase domain. In one embodiment, the TrkA fusion protein is LMNA-TrkA, TFG-TrkA, TPM3-TrkA, CD74-TrkA, NFASC-TrkA, MPRIP-TrkA, BCAN-TrkA, or TPR-TrkA, where:

LMNA=Prelamin-A/C;
TFG=TRK-fused gene protein;
TPM3=Tropomysin alpha-3;
CD74=HLA class II histocompatibility antigen gamma chain;
NFASC=Neurofascin;
MPRIP=MPRIP protein;
BCAN=Brevican core protein; and
TPR=Nucleoprotein TPR In one embodiment, the dysregulation of TrkA comprises one or more deletions, insertions or mutations in the TrkA protein. In one embodiment, the dysregulation comprises a deletion of one or more residues from the TrkA protein, resulting in constitutive activity of TrkA kinase. In one embodiment the deletion includes deletion of residues 303-377 in TrkA Isoform 2.

In one embodiment, the dysregulation of TrkA comprises a splice variation in which the expressed protein is an alternatively spliced variant of TrkA having one or more residues deleted resulting in constitutive activity of TrkA kinase. In one embodiment, an alternatively spliced form of TrkA with constitutive activity has deletions of exons 8, 9, and 11 resulting in an expressed protein missing residues 192-284 and 393-398 relative to TrkA Isoform 2.

Cancers identified as having dysregulation of TrkA (see literature references below; also see www.cancer.gov and www nccn.org) include:

(A) Cancers wherein the dysregulation of TrkA comprises one or more chromosome translocations or inversions resulting in TrkA gene fusions, including:

| Cancer | Literature reference(s) | Standard of Care |
|---|---|---|
| Non-Small Cell Lung Cancer | Vaishnavi et al. 2013: Nature Medicine 19, 1469-1472 | radiotherapy (e.g. radioiodide therapy, external-beam radiation, radium 223 therapy), chemotherapeutics as single agents (e.g. afatinib dimaleate, bevacizumab, carboplatin, cetuximab, cisplatin, crizotinib, erlotinib, gefitinib, gemcitabine, methotrexate, paclitaxel, pemetrexed) or combinations (e.g. carboplatin-paclitaxel, gemcitabine-paclitaxel, chemoradiation) |
| Papillary Thyroid Carcinoma | Caria et al. 2010: Cancer Genetics and Cytogenetics 203: 21-29 | Radiotherapies (e.g. radioiodide therapy, external-beam radiation) and chemotherapeutics (e.g. sorafenib, sunitinib, pazopanib) |
| Glioblastoma Multiforme | Frattini et al. 2013: Nature Genet. 45(10): 1141-9 | Chemotherapeutics (e.g. bevacizumab, everolimus, lomustine, temozolomide) |
| Colorectal Carcinoma | Martin-Zanca et al. 1986: Nature 319: 743 | Chemotherapeutics as single agents (aflibercept, bevacizumab, capecitabine, |

| Cancer | Literature reference(s) | Standard of Care |
|---|---|---|
| | | cetuximab, fluorouracil, irinotecan, leucovorin, oxaliplatin, panitumumab, regorafenib) or combinations (e.g. folfox, folfiri, capox, folfiri-bevacizumab, folfiri-cetuximab, xelox) |
| Melanoma | WO 2013/059740 A1 | Chemotherapeutics (e.g. aldesleukin, dabrafenib, dacarbazine, interferon alfa-2b, ipilimumab, peginterferon alfa-2b, trametinib, vemurafenib) |

(B) Cancers wherein the dysregulation of TrkA comprises one or more deletions, insertions or mutations in the TrkA protein, including:

| Cancer | Literature reference(s) | Standard of care |
|---|---|---|
| Acute Myeloid leukemia | Meyer 2007: Leukemia 21: 2171-2180<br>Reuther et al. 2000: Mol Cell Biol 20: 8655-8666 | Chemotherapeutics as single agents (e.g. arsenic trioxide, cyclophosphamide, cytarabine, daunorubicin, doxorubicin, vincristine) or combinations (e.g. ADE) |
| Large Cell Neuroendocrine Carcinoma | Marchetti et al 2008: Human Mutation 29(5): 609-616 | Radiotherapy (e.g. radioiodide therapy, external-beam radiation, radium 223 therapy) and/or chemotherapeutics (e.g. cisplatin, carboplatin, etoposide) |
| Neuroblastoma | Tacconelli et al 2004: Cancer Cell 6: 347 | Chemotherapeutics (e.g. cyclophosphamide, doxorubicin, vincristine) |

(C) Cancers driven by overexpression of wild-type TrkA (autocrine activation), including:

| Cancer | Literature Reference(s) | Standard of care |
|---|---|---|
| Prostate Carcinoma | Walch et al: Clinical & Experimental Metastasis 17: 307-314<br>Papatsoris et al 2007: Expert Opinion on Investigational Drugs 16(3): 303-309 | Radiotherapy (e.g. radium 223 therapy) or chemotherapeutics (e.g. abiraterone, cabazitaxel, degarelix, denosumab, docetaxel, enzalutamide, leuprolide, prednisone, sipuleucel-T) |
| Neuroblastoma | Van Noesel et al 2004: Gene 325: 1-15 | Chemotherapeutics (e.g. cyclophosphamide, doxorubicin, vincristine) |
| Pancreatic Carcinoma | Zhang et al 2005: Oncology Reports 14: 161-171 | Chemotherapeutics as single agents (e.g. erlotinib, fluorouracil, gemcitabine, mitomycin C) or combinations (e.g. gemcitabine-oxaliplatin) |
| Melanoma | Truzzi et al 2008: Journal of Investigative Dermatology 128(8): 2031 | Chemotherapeutics (e.g. aldesleukin, dabrafenib, dacarbazine, interferon alfa-2b, ipilimumab, peginterferon alfa-2b, trametinib, vemurafenib) |
| Head and Neck Squamous Cell Carcinoma | Kolokythas et al 2010: Journal of Oral and Maxillofacial Surgery 68(6): 1290-1295 | Radiotherapy and/or chemotherapeutics (e.g. bleomycin, cetuximab, cisplatin, docetaxel, fluorouracil, methotrexate) |
| Gastric Carcinoma | Ni et al 2012: Asian Pacific Journal of Cancer Prevention 13: 1511 | Chemotherapeutics (e.g. docetaxel, doxorubicin, fluorouracil, mitomycin C, trastuzumab) |

In one embodiment, provided herein is a method for treating a patient diagnosed with a cancer having a dysregulation of TrkA, comprising administering to the patient a therapeutically effective amount of a compound of the invention, or a pharmaceutically acceptable salt thereof, wherein the cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma.

In one embodiment, the compounds of the present invention are useful for treating cancer in combination with one or more additional therapeutic agents or therapies that work by the same or a different mechanism of action.

In one embodiment, the additional therapeutic agent(s) is selected from receptor tyrosine kinase-targeted therapeutic agents, including cabozantinib, crizotinib, erlotinib, gefitinib, imatinib, lapatinib, nilotinib, pazopanib, pertuzumab, regorafenib, sunitinib, and trastuzumab.

In one embodiment, the additional therapeutic agent(s) is selected from signal transduction pathway inhibitors, including Ras-Raf-MEK-ERK pathway inhibitors (e.g. sorafenib, trametinib, vemurafenib), PI3K-Akt-mTOR-S6K pathway inhibitors (e.g. everolimus, rapamycin, perifosine, temsirolimus) and modulators of the apoptosis pathway (e.g. obataclax).

In one embodiment, the additional therapeutic agent(s) is selected from cytotoxic chemotherapeutics, including arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

In one embodiment, the additional therapeutic agent(s) is selected from angiogenesis-targeted therapies, including aflibercept and bevacizumab.

In one embodiment, the additional therapeutic agent(s) is selected from immune-targeted agents, including aldesleukin, ipilimumab, lambrolizumab, nivolumab, sipuleucel-T.

In one embodiment, the additional therapeutic agent(s) is selected from agents active against the TrkA pathway, including NGF-targeted biopharmaceuticals such as NGF antibodies, and panTrk inhibitors.

In one embodiment, the additional therapeutic agent or therapy is radiotherapy, including radioiodide therapy, external-beam radiation and radium 223 therapy.

In one embodiment, the additional therapeutic agent(s) includes any one of the above listed therapies or therapeutic agents which are standards of care in cancers wherein the cancer has a dysregulation of TrkA.

In one embodiment, provided herein is a method of treating cancer in a patient, comprising administering to said patient a compound of the invention or a pharmaceutically acceptable salt thereof, in combination with at least one additional therapy or therapeutic agent selected from radiotherapy (e.g. radioiodide therapy, external-beam radiation, radium 223 therapy), cytotoxic chemotherapeutics (e.g. arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, vincristine), tyrosine kinase targeted-therapeutics (e.g. afatinib, cabozantinib, cetuximab, crizotinib, dabrafenib, erlotinib, gefitinib, imatinib, lapatinib, nilotinib, pazopanib, panitumumab, pertuzumab, regorafenib, sunitinib, trastuzumab), apoptosis modulators and signal transduction inhibitors (e.g. everolimus, perifosine, rapamycin, sorafenib, temsirolimus, trametinib, vemurafenib), immune-targeted therapies (e.g. aldesleukin, interferon alfa-2b, ipilimumab, lambrolizumab, nivolumab, prednisone, sipuleucel-T) and angiogenesis-targeted therapies (e.g. aflibercept, bevacizumab), wherein the amount of the compound of the invention or a pharmaceutically acceptable salt thereof is, in combination with the additional therapy or therapeutic agent, is effective in treating said cancer. These additional therapeutic agents may be administered with one or more compounds of the invention as part of the same or separate dosage forms, via the same or different routes of administration, and on the same or different administration schedules according to standard pharmaceutical practice known to one skilled in the art.

Also provided herein is (i) a pharmaceutical combination for treating cancer in a patient in need thereof, which comprises (a) a compound of the invention or a pharmaceutically acceptable salt thereof, (b) an additional therapeutic agent and (c) optionally at least one pharmaceutically acceptable carrier for simultaneous, separate or sequential use for the treatment of a tumor disease, wherein the amounts of the compound or salt thereof and of the additional therapeutic agent are together effective in treating said cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer a patient in need thereof.

In one embodiment, the combination therapy is for treating a cancer is selected from non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma and gastric carcinoma.

Another embodiment of this invention provides a method of treating inflammation or an inflammatory disease or disorder in a mammal, comprising administering to said mammal in need thereof one or more compounds of Formula I or a pharmaceutically acceptable salt thereof in an amount effective to treat said inflammation. In one embodiment, the inflammatory disease is inflammatory lung diseases (such as asthma), interstitial cystitis, bladder pain syndrome, inflammatory bowel diseases (including ulcerative colitis and Crohn's disease), and inflammatory skin diseases such as atopic dermatitis.

In one embodiment, the method of treating inflammation or an inflammatory disease or disorder comprises administering a compound of the invention in combination with one or more additional agents. Examples of additional agents include anti-TNF treatments (for example monoclonal antibody such as infliximab (Remicade), adalimumab (Humira), certolizumab pegol (Cimzia), and golimumab (Simponi), or a circulating receptor fusion protein such as etanercept (Enbrel)), antimetabolite and antifolate drug (for example Methotrexate), or targeted kinase inhibitors (for example JAK family inhibitors Ruxolitinib, Tofacitinib, CYT387, Lestaurtinib, Pacritinib and TG101348).

Another embodiment of this invention provides a method of treating *Trypanosoma cruzi* infection in a mammal, comprising administering to said mammal in need thereof one or more compounds of Formula I or a pharmaceutically acceptable salt thereof in an amount effective to treat said *Trypanosoma cruzi* infection.

Another embodiment of this invention provides a method of treating Sjogren's syndrome in a mammal, comprising administering to said mammal in need thereof one or more compounds of Formula I or a pharmaceutically acceptable salt thereof in an amount effective to treat said syndrome.

Another embodiment of this invention provides a method of treating endometriosis in a mammal, comprising administering to said mammal in need thereof one or more compounds of Formula I or a pharmaceutically acceptable salt thereof in an amount effective to treat said endometriosis.

Another embodiment of this invention provides a method of treating diabetic peripheral neuropathy in a mammal, comprising administering to said mammal in need thereof one or more compounds of Formula I or a pharmaceutically acceptable salt thereof in an amount effective to treat said diabetic peripheral neuropathy.

Another embodiment of this invention provides a method of treating prostatitis in a mammal, comprising administering to said mammal in need thereof one or more compounds of Formula I or a pharmaceutically acceptable salt thereof in an amount effective to treat said prostatitis.

Another embodiment of this invention provides a method of treating pelvic pain syndrome in a mammal, comprising administering to said mammal in need thereof one or more compounds of Formula I or a pharmaceutically acceptable salt thereof in an amount effective to treat said pelvic pain syndrome.

Another embodiment of this invention provides a method of treating a neurodegenerative disease in a mammal, comprising administering to said mammal in need thereof one or more compounds of Formula I or a pharmaceutically acceptable salt thereof in an amount effective to treat said neurodegenerative disease.

Another embodiment of this invention provides a method of treating diseases related to an imbalance of the regulation of bone remodeling in a mammal, comprising administering to said mammal in need thereof one or more compounds of Formula I or a pharmaceutically acceptable salt thereof in an amount effective to treat said disease. In one embodiment, the disease is osteoporosis, rheumatoid arthritis, and bone metastases.

In one embodiment, the method for treating diseases related to an imbalance of the regulation of bone remodeling in a mammal comprises administering a TrkA inhibitor of the invention in combination with one or more additional therapeutic agents or therapies. Examples of additional therapeutic agents or therapies include anti-TNF treatments (for example monoclonal antibody such as infliximab (Remicade), adalimumab (Humira), certolizumab pegol (Cimzia), and golimumab (Simponi), or with a circulating receptor fusion protein such as etanercept (Enbrel)), antimetabolite and antifolate drug (for example Methotrexate), or targeted kinase inhibitors (for example JAK family inhibitors Ruxolitinib, Tofacitinib, CYT387, Lestaurtinib, Pacritinib and TG101348).

As used herein, an "effective amount" means an amount of compound that, when administered to a mammal in need of such treatment, is sufficient to (i) treat a particular disease, condition, or disorder which can be treated with a compound of Formula I, or (ii) attenuate, ameliorate, or eliminate one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

The compounds of the present invention can be used in combination with one or more additional therapeutic agents that work by the same or a different mechanism of action. Examples of additional therapeutic agents include anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), and chemotherapeutic agents.

Also provided herein is a pharmaceutical combination comprising an effective amount of: (a) at least one compound of Formula I; and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), for use in the treatment of pain in a mammal, wherein (a) and (b) can be in separate dosage forms or in the same dosage form.

The term "pharmaceutical combination" as used herein refers to a pharmaceutical therapy resulting from the mixing or combining of more than one active ingredient and includes both fixed and non-fixed combinations of the active ingredients. The term "fixed combination" means that at least one of the compounds of Formula I, and at least one additional therapeutic agent are both administered to a patient simultaneously in the form of a single entity or dosage. The term "non-fixed combination" means that at least one of the compounds of Formula I, and at least one additional therapeutic agent, are administered to a patient as separate entities either simultaneously or sequentially with variable intervening time limits, wherein such administration provides effective levels of the two or more compounds in the body of the patient. These also apply to cocktail therapies, e.g. the administration of three or more active ingredients.

Also provided herein is a method of treating pain in a mammal, comprising co-administering to a mammal in need thereof an effective amount of: (a) at least one compound of Formula I; and (b) at least one additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), opioids (such as morphine), calcitonin gene-related peptide receptor antagonists, subtype-selective ion channel modulators, anticonvulsants (for example Pregabalin and gabapentin), dual serotonin-norepinephrin reuptake inhibitors (for example duloxetine, venlafaxine and milnacipran), and tricyclic antidepressants (such as amitriptyline, nortriptyline and desipramine).

The term "co-administering" is meant to encompass administration of the selected therapeutic agents to a single patient, and is intended to include treatment regimens in which the agents are administered by the same or different route of administration or at the same or different times. This term encompasses administration of two or more agents to a mammal so that both agents and/or their metabolites are present in the mammal at the same time. It includes simultaneous administration in separate compositions, administration at different times in separate compositions, and/or administration in a composition in which both agents are present. In some embodiments, the compound(s) of the invention and the other therapeutic agent(s) are administered in a single composition. In some embodiments, compound(s) of the invention and the other agent(s) are admixed in the composition.

Also provided herein is a medicament containing a compound of Formula I for treatment of pain in a mammal in combination with an additional therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine).

Also provided herein is a medicament containing a therapeutic agent selected from anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine) for treatment of pain in a mammal in combination with a compound of Formula I. Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

Another formulation may be prepared by mixing a compound described herein and a carrier or excipient. Suitable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound described herein or pharmaceutical composition thereof) or aid in the manufacturing of the pharmaceutical product (i.e., medicament).

Accordingly, another aspect of the present invention provides a pharmaceutical composition, which comprises a compound of Formula I or a pharmaceutically acceptable salt thereof, as defined hereinabove, together with a pharmaceutically acceptable diluent or carrier. According to another embodiment, the present invention provides a compound of Formula I or a pharmaceutically acceptable salt thereof, for use in the treatment of pain in a mammal. In one embodiment, the pain is chronic pain. In one embodiment the pain is acute pain. In one embodiment, the pain is inflammatory pain, neuropathic pain, or pain associated with cancer, surgery, or bone fracture.

According to another embodiment, the present invention provides a compound of Formula I or a pharmaceutically acceptable salt thereof, for use in the treatment of cancer in a mammal.

In another embodiment, the present invention provides a compound of Formula I or a pharmaceutically acceptable salt thereof, for use in the treatment of inflammation or an inflammatory disease or disorder in a mammal. In one embodiment, the inflammatory disease is inflammatory lung diseases (such as asthma), interstitial cystitis, bladder pain syndrome, inflammatory bowel diseases (including ulcerative colitis and Crohn's disease), and inflammatory skin diseases such as atopic dermatitis.

In another embodiment, the present invention provides a compound of Formula I or a pharmaceutically acceptable salt thereof, for use in the treatment of infectious diseases, for example *Trypanosoma cruzi* infection, in a mammal.

In another embodiment, the present invention provides a compound of Formula I or a pharmaceutically acceptable salt thereof, for use in the treatment of Sjogren's syndrome in a mammal.

In another embodiment, the present invention provides a compound of Formula I or a pharmaceutically acceptable salt thereof, for use in the treatment of endometriosis in a mammal.

In another embodiment, the present invention provides a compound of Formula I or a pharmaceutically acceptable salt thereof, for use in the treatment of diabetic peripheral neuropathy in a mammal, In another embodiment, the present invention provides a compound of Formula I or a pharmaceutically acceptable salt thereof, for use in the treatment of prostatitis in a mammal, In another embodiment, the present invention provides a compound of Formula I or a pharmaceutically acceptable salt thereof, for use in the treatment of pelvic pain syndrome in a mammal, In another embodiment, the present invention provides a compound of Formula I or a pharmaceutically acceptable salt thereof, for use in the treatment of a neurodegenerative disease in a mammal.

According to a further aspect, the present invention provides the use of a compound of Formula I or a pharmaceutically acceptable salt thereof, in the manufacture of a medicament for the treatment of a condition selected from pain, cancer, inflammation, neurodegenerative disease or *Trypanosoma cruzi* infection. In one embodiment, the condition is chronic pain. In one embodiment, the condition is acute pain. In one embodiment, the pain is inflammatory pain, neuropathic pain, or pain associated with cancer, surgery, or bone fracture. In one embodiment, the condition is cancer. In one embodiment, the condition is inflammation. In one embodiment, the condition is a neurodegenerative disease. In one embodiment, the condition is *Trypanosoma cruzi* infection. In one embodiment, the condition is Sjogren's syndrome. In one embodiment, the condition is endometriosis. In one embodiment, the condition is diabetic peripheral neuropathy. In one embodiment, the condition is prostatitis. In one embodiment, the condition is pelvic pain syndrome.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel or C-18 reverse phase column, or on a silica SepPak cartridge (Waters).

Biological Assay

Example A

TrkA Kinase Binding Assay

TrkA binding activity was determined in a TrkA LanthaScreen™ Eu Kinase Binding Assay. 5 nM His-tagged recombinant human TrkA (6HIS tagged cytoplasmic domain from Invitrogen, Catalog No. PV3144) was incubated with 4 nM Alexa-Fluor® Tracer 236 (Invitrogen Cat. No. PV5592), 2 nM biotinylated anti-His (Invitrogen Cat. No. PV6090), and 2 nM europium-labeled Streptavidin (Invitrogen Cat. No. PV5899), in buffer (25 mM MOPS, pH 7.5, 5 mM $MgCl_2$, 0.005% Triton X-100). Three fold serial dilutions of compounds of the invention in DMSO were added to a final percentage of 2% DMSO. After 60-minute incubation at 22° C., the reaction was measured using the EnVision mutlimode plate reader (PerkinElmer) via TR-FRET dual wavelength detection at 615 nM and 665 nM. The percent of control was calculated using a ratiometric emission factor. The $IC_{50}$ values were determined by fitting a four parameter model to the percent of control data.

Table A provides averaged $IC_{50}$ values for compounds of the invention when tested in the assay of Example A, where A represents an averaged $IC_{50}$ value <100 nM.

Example B p38 Kinase Binding Assay p38α binding activity was determined in a p38a LanthaScreen™ Eu Kinase Binding Assay. 5 nM of inactive, GST-tagged recombinant human p38a (GST-tagged cytoplasmic domain from Invitrogen, Catalog No. PV3305) was incubated with 5 nM Alexa-Fluor® Tracer 199 (Invitrogen Cat. No. PV5830), and 2 nM europium labeled anti-GST antibody (Invitrogen Cat. No. PV5594), in buffer (25 mM [Na+] HEPES pH 7.3, 10 mM $MgCl_2$, 100 μM $NaVO_4$). Three fold serial dilutions of compounds of the invention in DMSO were added to a final percentage of 2% DMSO. After 60-minute incubation at 22° C., the reaction was measured using the EnVision multimode plate reader (PerkinElmer) via TR-FRET dual wavelength detection at 615 nM and 665 nM. The percent of control was calculated using a ratiometric emission factor. The $IC_{50}$ values were determined by fitting a four parameter model to the percent of control data. The compounds of Examples 1-31 were tested in this assay, and all compounds were found to be 1000 fold more potent against TrkA than p38α.

TABLE A

| Example No. | TrkA Enzyme $IC_{50}$ (nM) |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |

TABLE A-continued

| Example No. | TrkA Enzyme $IC_{50}$ (nM) |
|---|---|
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 28 | A |
| 29 | A |
| 30 | A |
| 31 | A |

Example C

Off-Target Kinase Profiling

Two representative compounds (Example 2, 14) of the invention were tested for off-target kinase activity at a concentration of 10 μM by Millipore, Inc. in their KinaseProfiler™ service against all the kinases available in their full kinase panel. These compounds were run in duplicate at a concentration of ATP near the Km for each individual kinase according to Millipore's specifications. The results are shown in Table B. Data are reported as percent of control (POC) and are the average of the two replicates.

In the KinaseProfiler™ the compounds of Example 2 and Example 14 showed remarkable and unexpected selectivity for inhibiting TrkA versus other kinases in the panel. In fact, the compounds were largely inactive against off-target kinases at a concentration of 10 and thus would not be expected to inhibit off-target kinases at therapeutic doses in mammals. The ability of compounds of the invention to selectively inhibit the Trk pathway without inhibiting other off-target kinases could translate into drug profiles that are essentially free of side-effects related to inhibition of off-target kinases. Such a drug profile would represent a safer approach to treating pain, inflammation, cancer and certain skin diseases than has been previously reported.

TABLE B

| Kinase | Example 2 Avg POC | Example 14 Avg POC |
|---|---|---|
| Abl2 | 101 | 95.5 |
| Abl-P | 113.5 | 102.5 |
| AKT1 | 109.5 | 98.5 |
| AKT2 | 113 | 119.5 |
| AKT3 | 110 | 104 |
| ALK | 111 | 102.5 |
| ALK4 | 112.5 | 115 |
| AMPK(A1/B1/G1) | 118 | 106.5 |
| ARK5 | 89 | 85 |
| AURKA | 116 | 106 |
| Axl | 117 | 103 |
| BLK | 92 | 91.5 |
| Bmx | 115.5 | 105.5 |
| BrSK1 | 104 | 94 |
| BrSK2 | 93 | 99 |
| BTK | 109 | 97.5 |

TABLE B-continued

| Kinase | Example 2 Avg POC | Example 14 Avg POC |
|---|---|---|
| CAMK1 | 107 | 103.5 |
| CAMK1d | 100 | 103.5 |
| CAMK2b | 90.5 | 93 |
| CAMK2d | 91.5 | 105.5 |
| CAMK2g | 89.5 | 99 |
| CAMK4 | 97.5 | 83.5 |
| CDK1/cyclinB | 104 | 97 |
| CDK2/cyclinA | 111 | 113.5 |
| CDK2/cyclinE | 103 | 98.5 |
| CDK3/cyclinE | 98 | 100.5 |
| CDK5/p25 | 104 | 99 |
| CDK5/p35 | 113 | 115.5 |
| CDK6/cyclinD3 | 96 | 99.5 |
| CDK7/cyclinH/MAT1 | 88 | 97.5 |
| CDK9/cyclinT1 | 104 | 104 |
| CHK1 | 114.5 | 104.5 |
| CHK2 | 101 | 97.5 |
| CK1_y | 103 | 97.5 |
| CK1delta | 108 | 108.5 |
| CK1gamma1 | 92 | 80 |
| CK1gamma2 | 73.5 | 53 |
| CK1gamma3 | 87.5 | 95 |
| CK2alpha2 | 119.5 | 120 |
| CLK2 | 125 | 111.5 |
| CLK3 | 94 | 94 |
| c-RAF | 103.5 | 89 |
| CSK | 113 | 103 |
| DAPK1 | 97 | 99.5 |
| DAPK2 | 109 | 107 |
| DAPK3 | 107 | 105.5 |
| DCAMKL2 | 105 | 114.5 |
| DDR2 | 100.5 | 96 |
| DMPK | 98.5 | 105 |
| DRAK1 | 86.5 | 101.5 |
| DYRK2 | 90.5 | 85 |
| eEF-2K | 98.5 | 103 |
| EGFR | 105.5 | 96.5 |
| EphA1 | 97 | 99 |
| EphA2 | 110.5 | 96 |
| EphA3 | 101.5 | 106.5 |
| EphA4 | 108.5 | 103.5 |
| EphA5 | 102.5 | 101.5 |
| EphA7 | 101.5 | 106.5 |
| EphA8 | 104.5 | 104.5 |
| EphB1 | 93.5 | 97.5 |
| EphB2 | 109.5 | 120 |
| EphB3 | 105.5 | 138.5 |
| EphB4 | 104 | 96 |
| ErbB4 | 98 | 101.5 |
| ERK1 | 103 | 78.5 |
| ERK2 | 106.5 | 92.5 |
| FAK | 111.5 | 98.5 |
| FAK2 | 99.5 | 107 |
| Fer | 105 | 100.5 |
| Fes | 135.5 | 125 |
| FGFR1 | 106.5 | 101.5 |
| FGFR2 | 91.5 | 103 |
| FGFR3 | 111.5 | 133.5 |
| FGFR4 | 105.5 | 110 |
| Fgr | 108.5 | 80.5 |
| Flt1 | 86 | 81 |
| Flt3 | 119.5 | 90 |
| Flt4 | 95 | 92.5 |
| Fms | 101.5 | 76 |
| Fyn | 97 | 91.5 |
| GRK5 | 103.5 | 91 |
| GRK6 | 96.5 | 97 |
| GRK7 | 104 | 97 |
| GSK3alpha | 94 | 101.5 |
| GSK3beta | 108 | 114.5 |
| Haspin | 71.5 | 96 |
| Hck | 116.5 | 108.5 |
| HIPK1 | 96.5 | 97.5 |
| HIPK2 | 95 | 99 |
| HIPK3 | 99.5 | 89 |
| IGF-1R | 63 | 79 |
| IGF-1R Activated | 102 | 106 |
| IKKalpha | 121 | 118.5 |
| IKKbeta | 87 | 99 |
| IR | 74.5 | 84 |
| IR Activated | 106.5 | 100.5 |
| IRAK1 | 112.5 | 108.5 |
| IRAK4 | 132 | 110.5 |
| IRR | 105 | 96 |
| ITK | 111 | 101 |
| JAK2 | 112.5 | 109 |
| JAK3 | 103.5 | 101 |
| JNK1alpha1 | 98 | 105 |
| JNK2alpha2 | 100 | 97 |
| JNK3 | 111.5 | 121 |
| KDR | 116.5 | 99 |
| KIT | 101.5 | 101.5 |
| Lck | 113 | 112.5 |
| LIMK1 | 100 | 98 |
| LKB1 | 89.5 | 103.5 |
| LOK | 109 | 105 |
| Lyn | 112 | 105.5 |
| MAP3K5 | 97.5 | 104 |
| MAP4K2 | 105.5 | 99.5 |
| MAPKAP-K2 | 111 | 101 |
| MAPKAP-K3 | 101.5 | 105.5 |
| MAPKAP-K5 | 100 | 123.5 |
| MARK1 | 97.5 | 98 |
| MARK2 | 90 | 99.5 |
| MEK1 | 100.5 | 91 |
| MELK | 110 | 111.5 |
| Mer | 90.5 | 78 |
| Met | 106 | 96.5 |
| MINK | 98 | 89.5 |
| MKK4_m | 115 | 116.5 |
| MKK6 | 106.5 | 99.5 |
| MKK7 | 97.5 | 111 |
| MKNK2 | 101 | 101 |
| MLK1 | 103.5 | 102 |
| MRCKalpha | 113 | 124.5 |
| MRCKbeta | 105 | 98.5 |
| MSK1 | 102.5 | 106 |
| MSK2 | 120 | 116 |
| MSSK1 | 118 | 109 |
| MST1 | 94 | 97.5 |
| MST2 | 99.5 | 101 |
| MST3 | 101 | 105.5 |
| mTOR | 108.5 | 102.5 |
| mTOR/FKBP12 | 108.5 | 113 |
| MuSK | 103.5 | 98.5 |
| MYLK | 86.5 | 101.5 |
| NEK11 | 97 | 91 |
| NEK2 | 96 | 97.5 |
| NEK3 | 97 | 101 |
| NEK6 | 105.5 | 102 |
| NEK7 | 117 | 106.5 |
| NLK | 111.5 | 108.5 |
| p38alpha | 112 | 101 |
| p38beta | 101.5 | 93 |
| p38delta | 107.5 | 102.5 |
| p38gamma | 92 | 92.5 |
| p70S6K | 105.5 | 98 |
| PAK2 | 95.5 | 92.5 |
| PAK4 | 103.5 | 100.5 |
| PAK5 | 103 | 107 |
| PAK6 | 106 | 102 |
| PASK | 102.5 | 100.5 |
| PDGFRalpha | 110.5 | 114.5 |
| PDGFRbeta | 108.5 | 120 |
| PDK1 | 94.5 | 101.5 |
| PhKgamma2 | 90 | 88 |
| Pim-1 | 99.5 | 103.5 |
| Pim-2 | 86.5 | 103.5 |
| Pim-3 | 104 | 108.5 |
| PKAC-alpha | 94.5 | 109 |
| PKCalpha | 96 | 93 |
| PKCbetaI | 95 | 101 |
| PKCbetaII | 101.5 | 92 |
| PKCdelta | 102.5 | 99.5 |

TABLE B-continued

| Kinase | Example 2 Avg POC | Example 14 Avg POC |
|---|---|---|
| PKCepsilon | 103.5 | 114.5 |
| PKCeta | 108.5 | 100 |
| PKCgamma | 100.5 | 89.5 |
| PKCiota | 95 | 104.5 |
| PKCtheta | 98.5 | 98 |
| PKCzeta | 100 | 99.5 |
| PKD1 | 96 | 97 |
| PKD2 | 101.5 | 108 |
| Plk1 | 100 | 113 |
| Plk2 | 99.5 | 102 |
| Plk3 | 101 | 93.5 |
| PRK2 | 105 | 106.5 |
| PRKG1alpha | 108 | 100.5 |
| PRKG1beta | 97.5 | 101.5 |
| PrKX | 110.5 | 94 |
| PTK5 | 108 | 91 |
| PTK6 | 101 | 108.5 |
| Ret | 106.5 | 84 |
| RIPK2 | 105.5 | 93.5 |
| ROCK-I | 98 | 109.5 |
| ROCK-II | 102.5 | 93.5 |
| Ron | 122.5 | 104 |
| Ros | 105 | 91 |
| Rse | 96 | 96.5 |
| Rsk1 | 111 | 111.5 |
| Rsk2 | 106 | 99.5 |
| Rsk3 | 98 | 96 |
| Rsk4 | 136.5 | 113.5 |
| SGK1 | 98.5 | 99 |
| SGK2 | 99 | 100 |
| SGK3 | 106 | 107 |
| SIK | 106.5 | 96 |
| SRC | 105 | 103.5 |
| SRPK1 | 97.5 | 109.5 |
| SRPK2 | 96.5 | 102.5 |
| STK33 | 94 | 103.5 |
| Syk | 86 | 88 |
| TAK1 | 93 | 88 |
| TAO1 | 102.5 | 96.5 |
| TAO2 | 97 | 102.5 |
| TAO3 | 97.5 | 100.5 |
| TBK1 | 116.5 | 103 |
| TEC Activated | 107 | 83.5 |
| Tie2 | 71.5 | 71 |
| TLK2 | 92.5 | 93.5 |
| TNK2 | 109.5 | 97.5 |
| TrkA | 0.5 | 1 |
| TrkB | 1.5 | 4.5 |
| TSSK1 | 105 | 104.5 |
| TSSK2 | 107 | 107.5 |
| Txk | 99.5 | 98.5 |
| ULK2 | 96.5 | 106.5 |
| ULK3 | 100 | 98 |
| VRK2 | 101.5 | 109.5 |
| WNK2 | 98 | 99.5 |
| WNK3 | 99 | 96 |
| Yes | 104 | 55.5 |
| ZAP-70 | 93 | 101 |

Preparation of Synthetic Intermediates

Preparation A

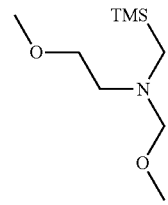

2-methoxy-N-(methoxymethyl)-N-((trimethylsilyl)methyl)ethanamine

Step A: Preparation of 2-methoxy-N-((trimethylsilyl)methyl)ethanamine

To a DMSO solution (15 mL) of 2-methoxyethanamine (14.2 mL, 163 mmol) at 90° C. was added a DMSO (10 mL) solution of (chloromethyl)trimethylsilane (11.4 mL, 81.5 mmol) by addition funnel over 40 minutes. The mixture was heated at 90° C. for 3.5 hours then cooled to ambient temperature. The mixture was then diluted with $H_2O$ (150 mL) and extracted with EtOAc (2×150 mL). The combined organic extracts were washed with brine (150 mL), dried with $MgSO_4$, filtered and concentrated to yield the product as a yellow oil (8.14 g, 62% yield). MS (apci) m/z=162.0 (M+H).

Step B: Preparation of 2-methoxy-N-(methoxymethyl)-N-((trimethylsilyl)methyl)ethanamine A MeOH (2.45 mL) solution of formaldehyde (37% aqueous, 4.91 g, 60.6 mmol) was cooled to 0° C., and treated with a dropwise addition of 2-methoxy-N-((trimethylsilyl)methyl)ethanamine (8.14 g, 50.5 mmol). The biphasic mixture was stirred at 0° C. for 3 hours, then $K_2CO_3$ (6.97 g, 50.5 mmol) was added and the mixture was stirred at 0° C. for 1 hour. The yellow oil was decanted onto $K_2CO_3$ (2.00 g, 14.4 mmol), and the mixture was stirred at ambient temperature for 2 hours. After the yellow oil was decanted, the solid $K_2CO_3$ was washed with $Et_2O$ (2×10 mL), and the $Et_2O$ washings were combined with the decanted yellow oil and concentrated on a rotary evaporator to yield the title compound as a yellow oil (9.92 g, 96% yield). $^1H$ NMR ($CDCl_3$) δ 4.00 (s, 2H), 3.37-3.43 (m, 2H), 3.29 (s, 3H), 3.19 (s, 3H), 2.77-2.82 (m, 2H), 2.18 (s, 2H), 0.00 (s, 9H).

Preparation B1

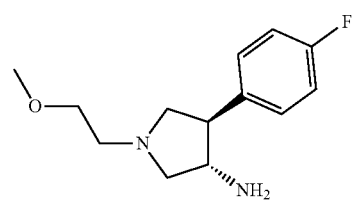 [SMILES: COCCN1C[C@@H](N)[C@H](c2ccc(F)cc2)C1]

(3S,4R)-4-(4-fluorophenyl)-1-(2-methoxyethyl)pyrrolidin-3-amine

Step A: Preparation of (E)-1-fluoro-4-(2-nitrovinyl)benzene

Acetic acid (2.0 L, 35.5 mol) and ammonium acetate (310.5 g, 4.03 mol) were stirred at ambient temperature for 1 hour, then nitromethane (611 mL, 11.3 mol) and 4-fluorobenzaldehyde (200 g, 1.61 mol) were added and the reaction mixture was heated to 90° C. for 3 hours. The reaction was allowed to cool to ambient temperature, then $H_2O$ (4 L) was added over 2 hours with mechanical stirring. The suspension was stirred 1 hour, then filtered and washed with 2:1 water/acetic acid (500 mL). The solids were dried in a vacuum oven (50° C.) to afford the title product as a pale yellow solid (238 g, 1.42 mol, 88% yield). $^1$H NMR (CDCl$_3$) δ 7.98 (1H), 7.55 (3H), 7.16 (2H).

Step B: Preparation of trans-3-(4-fluorophenyl)-1-(2-methoxyethyl)-4-nitro-pyrrolidine To a suspension of (E)-1-fluoro-4-(2-nitrovinyl)benzene (201 g, 1.20 mol) in DCM (1.09 L) and TFA (9.3 mL, 120 mmol) was added dropwise over 30 minutes 2-methoxy-N-(methoxymethyl)-N-((trimethylsilyl)methyl)ethanamine (Preparation A; 383 g, 1.86 mol) and the internal reaction temperature was maintained between 23-36° C. by cooling in an ice bath. The reaction mixture was poured into aqueous phosphate buffer solution (pH 7, 500 mL) and diluted with DCM (300 mL). The phases were separated and the aqueous phase was extracted with DCM (400 mL). The organic phases were combined, washed with brine (300 mL), dried (MgSO$_4$), filtered and concentrated under reduced pressure. The crude oil was purified by silica column chromatography eluting with 40% EtOAc/heptane to afford the title compound as a yellow oil (245 g, 76% yield). MS (apci) m/z=269.1 (M+H).

Step C: Preparation of trans-4-(4-fluorophenyl)-1-(2-methoxyethyl)pyrrolidin-3-amine To a solution of trans-3-(4-fluorophenyl)-1-(2-methoxyethyl)-4-nitropyrrolidine (289 g, 1.08 mol) in EtOH (1 L) was added platinum(IV) oxide (24.5 g, 108 mmol) in a Parr vessel and installed into a Parr shaker. The vessel was evacuated and backfilled with nitrogen (3×), then evacuated and backfilled with hydrogen (60 psi). The vessel was recharged with hydrogen as needed until the reaction was complete. The reaction mixture was filtered through Celite® and rinsed with MeOH (50 mL), then concentrated under reduced pressure to afford the title compound as a yellow oil (243 g, 95% yield). MS (apci) m/z=239.1 (M+H).

Step D: Preparation of (3S,4R)-4-(4-fluorophenyl)-1-(2-methoxyethyl)pyrrolidin-3-amine (2S,3S)-2,3-bis(4-methylbenzoyloxy)succinate To a solution of (3S,4R)-4-(4-fluorophenyl)-1-(2-methoxyethyl)pyrrolidin-3-amine (120 g, 504 mmol) in THF (3.0 L) and $H_2O$ (333 mL) was added di-p-toluoyl-D-tartaric acid (195 g, 504 mmol). Stirred at ambient temperature for 1 hour, then placed in a freezer (−11° C.) for 18 hours. The mixture was stirred to give a slurry, filtered, and rinsed with Et$_2$O (4×100 mL). The solid was dried in vacuum oven (40° C.) for 4 hours, then recrystallized twice by the following procedure: the solid was dissolved in THF (1.06 mL) and $H_2O$ (118 mL) with heating to 45° C., then allowing to cool to ambient temperature over 2 hours, then placed in a freezer (−11° C.) for 18 hours; the mixture was stirred to give a slurry, filtered, and rinsed with Et$_2$O (4×100 mL). After two recrystallizations, the solid was dried in vacuum oven (40° C.) for 18 hours to afford the title compound as a white crystalline solid (96 g, 31% yield). MS (apci) m/z=239.2 (M+H).

Step E: Preparation of (3S,4R)-4-(4-fluorophenyl)-1-(2-methoxyethyl)pyrrolidin-3-amine (3S,4R)-4-(4-fluorophenyl)-1-(2-methoxyethyl)pyrrolidin-3-amine (2S,3S)-2,3-bis(4-methylbenzoyloxy)succinate (20 g, 32.0 mmol) was dissolved in DCM (300 mL) and washed with 1M NaOH (2×200 mL). The combined aqueous phases were extracted with DCM (200 mL). The combined organic extracts were washed with brine (200 mL), dried (MgSO$_4$), filtered and concentrated, then dried under vacuum to afford the title compound as a yellow oil (6.17 g, 81%, >99% ee). MS (apci) m/z=239.1 (M+H).

The following pyrrolidine intermediates B2 and B3 were made according to the method of Preparation B1, Steps A-E, including chiral crystallization and using the appropriate benzaldehyde in Step A and replacing EtOH and platinum (IV) oxide with MeOH and Raney nickel respectively in Step C. Intermediates B4-B7 were made according to the method of Preparation B1, Steps A-C.

| Preparation # | Structure | Name | Data |
|---|---|---|---|
| B2 | 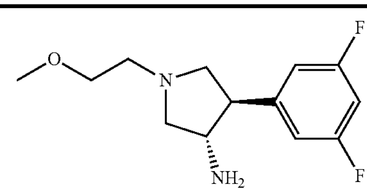 | (3S,4R)-4-(3,5-difluorophenyl)-1-(2-methoxyethyl)pyrrolidin-3-amine | MS (apci) m/z = 257.1 (M + H) |
| B3 | 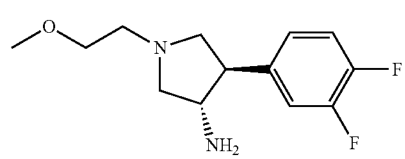 [SMILES: COCCN1C[C@@H](N)[C@H](c2ccc(F)c(F)c2)C1] | (3S,4R)-4-(3,4-difluorophenyl)-1-(2-methoxyethyl)pyrrolidin-3-amine (2S,3S)-2,3-bis(4-methylbenzoyloxy)succinate | MS (apci) m/z = 257.1 (M + H) |

-continued

| Preparation # | Structure | Name | Data |
|---|---|---|---|
| B4 | 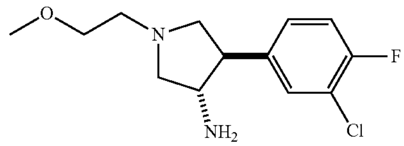 [SMILES: COCCN1C[C@@H](N)[C@H](c2ccc(F)c(Cl)c2)C1] | trans-4-(3-chloro-4-fluoro-phenyl)-1-(2-methoxyethyl)pyrrolidin-3-amine | MS (apci) m/z = 273.1 (M + H) |
| B5 | 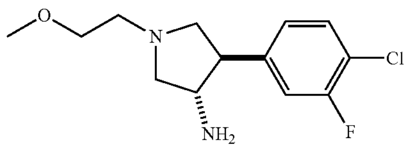 [SMILES: COCCN1C[C@@H](N)[C@H](c2ccc(Cl)c(F)c2)C1] | trans-4-(4-chloro-3-fluoro-phenyl)-1-(2-methoxyethyl)pyrrolidin-3-amine | MS (apci) m/z = 273.1 (M + H) |
| B6 | 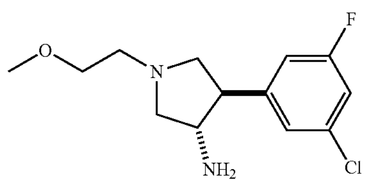 [SMILES: COCCN1C[C@@H](N)[C@H](c2cc(F)cc(Cl)c2)C1] | trans-4-(3-chloro-5-fluoro-phenyl)-1-(2-methoxyethyl)pyrrolidin-3-amine | MS (apci) m/z = 273.1 (M + H) |
| B7 | 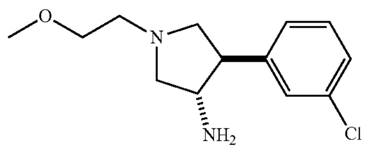 | trans-4-(3-chlorophenyl)-1-(2-methoxyethyl)pyrrolidin-3-amine | MS (apci) m/z = 255.1 (M + H) |

Preparation C

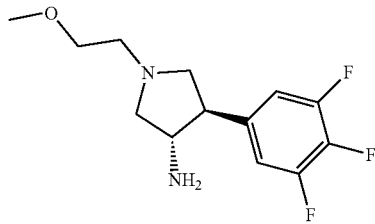 [SMILES: COCCN1C[C@@H](N)[C@H](c2cc(F)c(F)c(F)c2)C1]

(3S,4R)-1-(2-methoxyethyl)-4-(3,4,5-trifluorophenyl)pyrrolidin-3-amine dihydro chloride Step A: Preparation of (E)-3-(3,4,5-trifluorophenyl)acryloyl chloride To a suspension of (E)-3-(3,4,5-trifluorophenyl)acrylic acid (5.15 g, 25.5 mmol) in toluene (50 mL) was added oxalyl chloride (4.43 mL, 51.0 mmol) and the mixture was stirred for 5 minutes at ambient temperature. The mixture was cooled to 0° C. and DMF (0.0493 mL, 0.637 mmol) was added (immediate, mild gas evolution). The mixture was stirred for 10 minutes, the ice bath was removed and the mixture allowed to reach ambient temperature (sustained gas evolution). Stirring was continued for 16 hours and the mixture was concentrated in vacuo. The residue was dissolved in Et$_2$O (100 mL), treated with activated carbon and filtered through a packed Celite® plug capped with a MgSO$_4$ layer (Et$_2$O elution). The filtrate was concentrated in vacuo to afford (E)-3-(3,4,5-trifluorophenyl)acryloyl chloride (6.1 g, 109%) as a faint green oil which was used directly in the next step. $^1$H NMR (CDCl$_3$) δ 7.66 (d, J=15.6 Hz, 1H), 7.22 (m, 2H), 6.57 (d, J=15.6 Hz, 1H) ppm.

Step B: Preparation of (R,E)-4-phenyl-3-(3-(3,4,5-trifluorophenyl)acryloyl)oxazolidin-2-one A solution of (R)-4-phenyloxazolidin-2-one (3.92 g, 24.0 mmol) in THF (60 mL) was cooled to −78° C. and lithium bis(trimethylsilyl)amide (25.2 mL, 25.2 mmol, 1.0 M in THF) was added dropwise over 10 minutes. The mixture was stirred at −78° C. for 45 minutes and a solution of (E)-3-(3,4,5-trifluorophenyl)acryloyl chloride (5.56 g, 25.2 mmol) in THF (15 mL) was added. The mixture was stirred for 17 hours during which time the mixture reached ambient temperature and was poured into cold water (300 mL). The aqueous mixture was extracted with 50% EtOAc/hexanes (3×) and the combined organic phases were washed with brine, dried over MgSO$_4$/activated carbon and filtered through a packed SiO$_2$ plug capped with a MgSO$_4$ layer (50% EtOAc/hexanes for elution). The filtrate was concentrated in vacuo to afford (R,E)-4-phenyl-3-(3-(3,4,5-trifluorophenyl)acryloyl)oxazolidin-2-one (8.40 g, 100%) as an ivory white solid. $^1$H NMR (CDCl$_3$) δ 7.84 (d, J=15.7 Hz, 1H), 7.57 (d, J=15.7 Hz, 1H), 7.42-7.33 (m, 5H), 7.21-7.18 (m, 2H), 5.54 (dd, J=8.7, 3.9 Hz, 1H), 4.75 (t, J=8.8 Hz, 1H), 4.34 (dd, J=8.9, 3.9 Hz, 1H) ppm.

Step C: Preparation of (R)-3-((3S,4R)-1-(2-methoxyethyl)-4-(3,4,5-trifluorophenyl)pyrrolidine-3-carbonyl)-4-phenyloxazolidin-2-one A solution of (R,E)-4-phenyl-3-(3-(3,4,5-trifluorophenyl)acryloyl)oxazolidin-2-one (9.50 g, 27.4 mmol) and TFA (2.11 mL, 2.74 mmol) in toluene (270 mL) was cooled to 0°

C. and 2-methoxy-N-(methoxymethyl)-N-((trimethylsilyl)methyl)ethanamine (Preparation A, 8.43 g, 41.0 mmol) in toluene (25 mL) was added dropwise over 15 minutes. The mixture was stirred for 2.5 hours at 0° C., was treated with 1M $K_2CO_3$ (200 mL) and warmed to ambient temperature. The organic layer was separated and was washed with water and brine. The solution was dried over $MgSO_4$ and filtered through a packed $SiO_2$ plug capped with a $MgSO_4$ layer eluting with $Et_2O$ then 30% EtOAc/hexanes. The filtrate was concentrated and the residue purified by silica column chromatography eluting with 25% EtOAc/hexanes to afford (R)-3-((3S,4R)-1-(2-methoxyethyl)-4-(3,4,5-trifluorophenyl)pyrrolidine-3-carbonyl)-4-phenyloxazolidin-2-one (7.1 g, 58% yield) as a colorless syrup. $^1$H NMR ($CDCl_3$) δ 7.42-7.35 (m, 3H), 7.28-7.26 (m, 2H), 6.96-6.93 (m, 2H), 5.40 (dd, J=8.8, 4.1 Hz, 1H), 4.67 (t, J=8.9 Hz, 1H), 4.26 (dd, J=9.0, 4.1 Hz, 1H), 4.12 (q, J=14.3, 7.1 Hz, 1H), 4.14-4.01 (m, 1H), 3.47 (t, J=5.7 Hz, 2H), 3.39 (t, J=9.5 Hz, 1H), 3.33 (s, 3H), 3.02 (m, 1H), 2.73-2.59 (m, 4H) ppm.

Step D: Preparation of (3S,4R)-1-(2-methoxyethyl)-4-(3,4,5-trifluorophenyl)pyrrolidine-3-carboxylic acid A 1M aqueous solution of LiOH (39.0 mL, 39.0 mmol) was cooled to 0° C. and $H_2O_2$ (3.37 mL, 33.0 mmol, 30 wt %) was added. The chilled mixture was added to solution of (R)-3-((3S,4R)-1-(2-methoxyethyl)-4-(3,4,5-trifluorophenyl)pyrrolidine-3-carbonyl)-4-phenyloxazolidin-2-one (7.0 g, 15.6 mmol) in THF (75 mL) over 30 minutes at 0° C. After stirring for 1 hour, 2.0 M aqueous $Na_2SO_3$ (33.0 mL, 65.9 mmol) was introduced and the reaction mixture was warmed to ambient temperature. After stirring for 2 hours, the mixture was diluted with water (100 mL) and acidified with 6 N HCl to pH 5. The mixture was treated with NaCl and extracted with 10% iPrOH/DCM (8×). The combined organic layers were dried over $Na_2SO_4$ and filtered through a packed Celite® plug capped with a $MgSO_4$ layer eluting with DCM. The filtrate was concentrated in vacuo to afford (3S,4R)-1-(2-methoxyethyl)-4-(3,4,5-trifluorophenyl)pyrrolidine-3-carboxylic acid (4.0 g, 85% yield) as a colorless syrup. MS (apci) m/z=304.1 (M+H).

Step E: Preparation of benzyl (3S,4R)-1-(2-methoxyethyl)-4-(3,4,5-trifluorophenyl)pyrrolidin-3-ylcarbamate To a solution of (3S,4R)-1-(2-methoxyethyl)-4-(3,4,5-trifluorophenyl)pyrrolidine-3-carboxylic acid (4.0 g, 11.9 mmol) in toluene (50 mL) was added DIEA (5.18 mL, 29.7 mmol) followed by diphenyl phosphoryl azide (5.3 mL, 27.3 mmol). The mixture was stirred at ambient temperature for 1 hour and then heated to reflux for 1 hour. Benzyl alcohol (2.47 mL, 23.7 mmol) was added and the reaction mixture was refluxed for 3 hours. The reaction mixture was cooled to ambient temperature and added to water (150 mL). The layers were separated and the aqueous layer was extracted with EtOAc (2×). The combined organic phases were washed with brine, dried over $MgSO_4$/activated carbon and filtered through packed Celite®. The filtrate was concentrated in vacuo and the residue purified by silica column chromatography (50% EtOAc/hexanes, EtOAc, 5% MeOH/EtOAc step gradient) to afford benzyl (3S,4R)-1-(2-methoxyethyl)-4-(3,4,5-trifluorophenyl)pyrrolidin-3-ylcarbamate (1.07 g, 22% yield) as a bronze syrup. MS (apci) m/z=409.1 (M+H).

Step F: Preparation of (3S,4R)-1-(2-methoxyethyl)-4-(3,4,5-trifluorophenyl)pyrrolidin-3-amine dihydrochloride A mixture of benzyl (3S,4R)-1-(2-methoxyethyl)-4-(3,4,5-trifluorophenyl)pyrrolidin-3-ylcarbamate (1.05 g, 2.31 mmol) and TFA (15 mL) was heated at 60° C. for 7 hours. Additional TFA (10 mL) was added and the mixture heated at 75° C. for 1 hour. The reaction mixture was cooled to ambient temperature and concentrated in vacuo. The residue was dissolved in a minimal amount of DCM and added dropwise to 1M HCl in $Et_2O$ (200 mL) at 0° C. The resulting suspension was filtered and the collected solid was washed with ether and dried in vacuo to afford the title compound (785 mg, 98% yield) as a light grey powder. $^1$H NMR ($D_2O$) δ 7.06-7.10 (m, 2H), 4.13-4.20 (m, 1H), 3.92-3.99 (m, 2H), 3.71-3.74 (m, 1H), 3.57-3.63 (m, 3H), 3.41-3.49 (m, 3H), 3.25 (s, 3H) ppm.

Preparation D

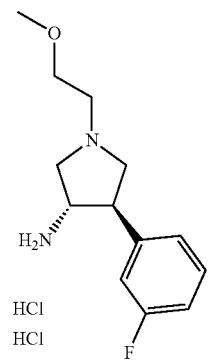 [SMILES: COCCN1C[C@@H](N)[C@H](c2cccc(F)c2)C1 ; Cl ; Cl]

(3S,4R)-4-(3-fluorophenyl)-1-(2-methoxyethyl)pyrrolidin-3-amine dihydrochloride

Step A: Preparation of tert-butyl (3S,4R)-4-(3-fluorophenyl)-1-(2-methoxyethyl)pyrrolidin-3-ylcarbamate A solution of tert-butyl (3S,4R)-4-(3-fluorophenyl)pyrrolidin-3-ylcarbamate (250 mg, 0.89 mmol, commercially available), DIEA (0.48 mL, 2.68 mmol) and 1-bromo-2-methoxyethane (149 mg, 1.07 mmol) in DMF (3 mL) was stirred at ambient temperature for 2 hours, then heated to 60° C. for 4 hours, then cooled to ambient temperature overnight. After partitioning between EtOAc and saturated $NaHCO_3$ (10 mL each), the organic layer was washed with water and brine (2×10 mL each), dried over $Na_2SO_4$, filtered and concentrated to yield tert-butyl (3S,4R)-4-(3-fluorophenyl)-1-(2-methoxyethyl)pyrrolidin-3-ylcarbamate (250 mg, 83% yield) as a viscous orange oil. LCMS (apci) m/z=339.1 (M+H).

Step B: Preparation of (3S,4R)-4-(3-fluorophenyl)-1-(2-methoxyethyl)pyrrolidin-3-amine dihydrochloride A solution of tert-butyl (3S,4R)-4-(3-fluorophenyl)-1-(2-methoxyethyl)pyrrolidin-3-ylcarbamate (250 mg, 0.74 mmol) in 5-6 N HCl in isopropyl alcohol (14.8 mL, 73.9 mmol) was stirred at ambient temperature for 1 hour. The mixture was concentrated in vacuo and triturated with Et$_2$O to afford the title compound (230 mg, 100% yield) as beige solid. LCMS (apci) m/z=239.1 (M+H).

Preparation A-100

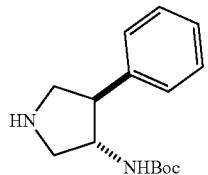 [SMILES: CC(C)(C)OC(=O)N[C@@H]1CNC[C@H]1c1ccccc1]

tert-butyl trans-4-phenylpyrrolidin-3-ylcarbamate

Step A: Preparation of trans-1-benzyl-3-nitro-4-phenylpyrrolidine

To a DCM (2 L) solution of (E)-(2-nitrovinyl)benzene (149 g, 1.00 mol) was added TFA (19.5 mL, 0.250 mol), followed by cooling to 15° C. and then slow addition of a DCM (500 mL) solution of N-methoxymethyl-N-(trimethylsilylmethyl)benzylamine (274 g, 1.00 mol) over 3 hours, maintaining the reaction temperature between 15 and 10° C. The reaction was warmed up to ambient temperature and stirred for 18 hours, then washed with 2 N NaOH (500 mL) and treated with 2 N HCl (1 L). The resulting white suspension was stirred for 1 hour before being filtered and washed with DCM. DCM (1 L) and 2 N NaOH (750 mL) were then added to the collected white solid and stirred until all solid dissolved. After phase-separation, the aqueous layer was extracted with DCM (2×1 L). The combined organic layers were dried with MgSO$_4$, filtered and concentrated to afford the title product as an off-white solid (205 g, 73% yield). MS (apci) m/z=283.1 (M+H).

Step B: Preparation of trans-1-benzyl-4-phenylpyrrolidin-3-amine

To a suspension of trans-1-benzyl-3-nitro-4-phenyl-pyrrolidine (93.9 g, 333 mmol) in EtOH (1.20 L) was added concentrated HCl (450 mL), followed by addition of zinc dust (173 g, 2.66 mol) in small portions over 1.5 hours while maintaining the temperature between 55-60° C. The reaction mixture was stirred at ambient temperature for 18 hours, then cooled in an ice/water bath followed by addition of concentrated NH$_4$OH (900 mL). The mixture (pH=10-11) was filtered and the collected zinc was washed with CHCl$_3$. The filtrate was then phase-separated, and the aqueous layer was extracted with CHCl$_3$ (2×400 mL). The combined organics was washed with H$_2$O, brine, dried with MgSO$_4$, filtered and concentrated to afford the title compound as an amber oil (85.0 g, 100% yield). MS (apci) m/z=253.2 (M+H).

Step C: Preparation of trans-(1-benzyl-4-phenyl-pyrrolidin-3-yl)-carbamic acid tert-butyl ester To a mixture of trans-1-benzyl-4-phenylpyrrolidin-3-amine (85.0 g, 333 mmol), THF (750 mL) and triethylamine (69.6 mL, 500 mmol), was slowly added (Boc)$_2$O (72.7 g, 333 mmol) in portions over 30 minutes. The reaction mixture was stirred at ambient temperature for 16 hours and was concentrated in vacuo. The residue was dissolved in CHCl$_3$ and was washed with aqueous Na$_2$CO$_3$ and brine. The organic layer was dried with MgSO$_4$, filtered and concentrated to afford the title compound as a pale-yellow solid (116 g, 99% yield). MS (apci) m/z=353.0 (M+H).

Step D: Preparation of tert-butyl trans-4-phenylpyrrolidin-3-ylcarbamate

A 2 gallon Parr reactor was charged with trans-(1-benzyl-4-phenyl-pyrrolidin-3-yl)-carbamic acid tert-butyl ester (114 g, 323 mmol), EtOH (2 L) and 10% Pd/C (50% wet, 11.0 g). The reactor was purged with N$_2$ several times, filled with H$_2$ to 56-57 psi and agitated at 80° C. When the reaction was complete according to HPLC analysis, the reaction mixture was filtered and the filtrate concentrated to provide the crude product as a yellow solid. The crude material was triturated from toluene to afford the title product as a white solid (68.4 g, 78% yield). MS (apci) m/z=262.9 (M+H).

Preparation A-101

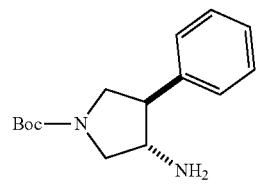 [SMILES: CC(C)(C)OC(=O)N1C[C@@H](N)[C@H](c2ccccc2)C1]

trans-tert-butyl 3-amino-4-phenylpyrrolidine-1-carboxylate

Step A: Preparation of trans-N-(1-benzyl-4-phenylpyrrolidin-3-yl)-2,2,2-trifluoroacetamide To a solution of trans-1-benzyl-4-phenylpyrrolidin-3-amine (Preparation A-100, Step B, 61.9 g, 245 mmol) in DCM (400 mL) was added DIEA (64.1 mL, 368 mmol) and the mixture was cooled in an ice bath. Trifluoroacetic anhydride (38.1 mL, 270 mmol) was added dropwise over 30 minutes under a N$_2$ atmosphere. After the addition, the mixture was stirred for 30 minutes and then concentrated in vacuo. The residue was dissolved in DCM and washed with saturated aqueous NaHCO$_3$ and brine. The solution was dried with MgSO$_4$, filtered and concentrated in vacuo. The crude material was treated with hexanes and the resulting yellow suspension was stirred at ambient temperature for 1 hour. The solid was collected by filtration, washed with hexanes and dried under vacuum to afford the title compound (78.7 g, 92% yield) as a yellow solid. MS (apci) m/z=349.1 (M+H).

Step B: Preparation of trans-tert-butyl-3-phenyl-4-(2,2,2-trifluoroacetamido) pyrrolidine-1-carboxylate A solution of trans-N-(1-benzyl-4-phenyl pyrrolidin-3-yl)-2,2,2-trifluoroacetamide (78.7 g, 226 mmol) in EtOH (400 mL) was purged with N$_2$ and treated with 20% Pd(OH)$_2$ on activated carbon (31.7 g, 45.2 mmol). The mixture was agitated at ambient temperature under 30 psi of H$_2$ in a parr reactor for 7 hours, and then filtered through GF/F paper and concentrated in vacuo. The residue was dissolved in DCM (250 mL), followed by the addition of TEA (49.4 mL, 355 mmol) and cooling in an ice bath. Boc₂O (56.8 g, 260 mmol) was added slowly over 15 minutes and the reaction mixture was warmed to ambient temperature and stirred for 1 hour. The mixture was washed with saturated aqueous NaHCO₃ and brine, then dried with MgSO₄. The solution was filtered, concentrated and the residue was purified by silica column chromatography eluting with 40% EtOAc/hexanes to provide the title compound as a white solid (63.2 g, 75% yield). ¹H NMR (CDCl₃) δ 7.23-7.39 (m, 5H), 6.36 (br s, 1H), 4.47-4.55 (m, 1H), 3.92-4.00 (m, 1H), 3.78-4.00 (m, 1H), 3.50-3.59 (m, 1H), 3.22-3.45 (m, 2H), 1.49 (s, 9H).

Step C: Preparation of trans-tert-butyl 3-amino-4-phenylpyrrolidine-1-carboxylate A solution of trans tert-butyl 3-phenyl-4-(2,2,2-trifluoroacetamido)pyrrolidine-1-carboxylate (63.2 g, 176 mmol) in MeOH (200 mL) was cooled in an ice bath and 2 N NaOH (220 mL, 440 mmol) was added. The reaction mixture was allowed to warm to ambient temperature overnight, then concentrated to approximately 200 mL and diluted with H₂O (200 mL). The aqueous mixture was extracted with DCM and the combined extracts were washed with brine and dried over Na₂SO₄. The solution was filtered and concentrated to give the title compound as a light yellow oil (46.2 g, 99% yield). MS (apci) m/z=163.0 (M+H-Boc).

Preparation B-100

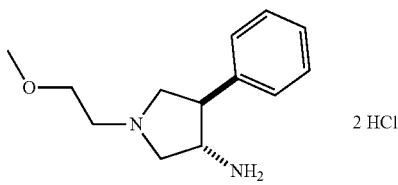 [SMILES: COCCN1C[C@@H](N)[C@H](c2ccccc2)C1]

trans-1-(2-methoxyethyl)-4-phenylpyrrolidin-3-amine dihydrochloride

Step A: Preparation of tert-butyl trans-1-(2-methoxyethyl)-4-phenylpyrrolidin-3-ylcarbamate To a solution of tert-butyl trans-4-phenylpyrrolidin-3-ylcarbamate (Preparation A-100, 4.82 g, 17.5 mmol) in dry DMF (50 mL) was added sequentially DIEA (9.12 mL, 52.4 mmol) and 1-bromo-2-methoxyethane (1.97 mL, 20.9 mmol). The mixture was stirred at ambient temperature for 46 hours and then poured into H₂O (300 mL). The mixture was extracted with EtOAc (3×150 mL) and the combined extracts were washed with brine, dried over MgSO₄/activated carbon, filtered through a SiO₂ plug capped with packed MgSO₄, and eluted with EtOAc. The solution was concentrated and dried in vacuo yielding the product as a white solid (5.15 g, 92% yield). MS (apci) m/z=321.1 (M+H).

Step B: Preparation of trans-1-(2-methoxyethyl)-4-phenylpyrrolidin-3-amine dihydrochloride To a solution of tert-butyl trans-1-(2-methoxyethyl)-4-phenylpyrrolidin-3-ylcarbamate (5.10 g, 15.9 mmol) in 2:1 EtOAc-MeOH (150 mL) was added 4 N HCl in dioxane (59.7 mL, 239 mmol). The mixture was stirred at ambient temperature for 90 minutes and then concentrated in vacuo. The resulting foam was treated with EtOAc (200 mL), sonicated for 5 minutes and stirred vigorously until a fine white suspension formed. The suspension was filtered, washed with EtOAc and dried under vacuum to afford the title compound as a white powder (5.10 g, 100% yield). MS (apci) m/z=221.1 (M+H).

Preparation D-100

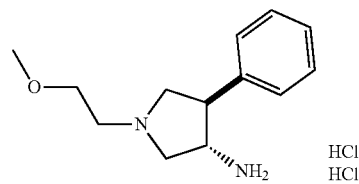 [SMILES: COCCN1C[C@@H](N)[C@H](c2ccccc2)C1 ; "HClHCl"]

(3S,4R)-1-(2-methoxyethyl)-4-phenylpyrrolidin-3-amine dihydrochloride

Step A: Preparation of (R)-3-cinnamoyl-4-phenyloxazolidin-2-one

A THF (50 mL) solution of (R)-4-phenyloxazolidin-2-one (5.90 g, 36.2 mmol) was cooled to −78° C. and treated with lithium bis(trimethylsilyl)amide (36.9 mL, 36.9 mmol, 1.0 M in THF) dropwise over 15 minutes. After 15-minute stirring at −78° C., a THF (10 mL) solution of cinnamoyl chloride (6.33 g, 38.0 mmol) was then introduced. The mixture was stirred for 1 hour at −78° C. and 2 hours at ambient temperature before it was quenched with saturated NaHCO₃ (50 mL) and stirred for 1 hour. The mixture was diluted with EtOAc (200 mL), washed with water and brine, dried over MgSO₄, filtered and concentrated to give the product as a pale yellow solid (10.6 g, 99.9% yield). MS (apci) m/z=293.9 (M+H).

Step B: Preparation of (R)-3-((3S,4R)-1-(2-methoxyethyl)-4-phenylpyrrolidine-3-carbonyl)-4-phenyloxazolidin-2-one A toluene (500 mL) solution of (R)-3-cinnamoyl-4-phenyloxazolidin-2-one (8.00 g, 27.3 mmol) and TFA (0.210 mL, 2.73 mmol) was first cooled to 5-10° C., followed by dropwise addition of a toluene (30 mL) solution of 2-methoxy-N-(methoxymethyl)-N-((trimethylsilyl)methyl) ethanamine (Preparation C, 8.40 g, 40.9 mmol). The resulting mixture was warmed up to ambient temperature and stirred for 3 hours, then washed with saturated NaHCO₃ and water, dried with MgSO₄, filtered and concentrated in vacuo. The crude material was purified by silica column chromatography, eluting with 16-20% EtOAc/hexanes, to afford the product (6.5 g, 60% yield). MS (apci) m/z=395.2 (M+H).

Step C: Preparation of (3S,4R)-1-(2-methoxyethyl)-4-phenylpyrrolidine-3-carboxylic acid To a 1M aqueous solution of LiOH (41.2 mL, 41.2 mmol) at 0° C. was added H₂O₂ (3.37 mL, 33.0 mmol, 30 wt %). The mixture was then added to solution of (R)-3-((3S,4R)-1-(2-methoxyethyl)-4-phenylpyrrolidine-3-carbonyl)-4- phenyloxazolidin-2-one (6.50 g, 16.5 mmol) in THF (100 mL) over 10 minutes at 0° C. After 1 hour stirring, 2.0 M aqueous Na$_2$SO$_3$ (33.0 mL, 65.9 mmol) was introduced at 0° C. and the reaction mixture was warmed to ambient temperature. After stirring for 10 minutes, the mixture was washed with EtOAc (50 mL). The aqueous layer was acidified with 1 N HCl until pH 3-5, then treated with NaCl (10 g), then extracted with 10% iPrOH/DCM. The organic layer was dried with MgSO$_4$, filtered and concentrated to give the product (4.11 g, 100% yield). MS (apci) m/z=250.1 (M+H).

Step D: Preparation of benzyl (3S,4R)-1-(2-methoxyethyl)-4-phenylpyrrolidin-3-ylcarbamate To a solution of (3S,4R)-1-(2-methoxyethyl)-4-phenylpyrrolidine-3-carboxylic acid (4.11 g, 16.5 mmol) in toluene (70 mL) was added TEA (5.74 mL, 41.2 mmol) followed by diphenyl phosphoryl azide (4.99 mL, 23.1 mmol). The mixture was stirred at ambient temperature for 1 hour and then heated to reflux for 1 hour. Benzyl alcohol (3.42 mL, 33.0 mmol) was then added and the reaction mixture was refluxed for 15 hours. The reaction mixture was treated with EtOAc, washed with water, dried over MgSO$_4$, filtered and concentrated in vacuo. The crude material was purified by silica column chromatography, eluting with 1% MeOH/DCM to afford the product (2.5 g, 43% yield). MS (apci) m/z=355.2 (M+H).

Step E: Preparation of (3S,4R)-1-(2-methoxyethyl)-4-phenylpyrrolidin-3-amine dihydrochloride Benzyl (3S,4R)-1-(2-methoxyethyl)-4-phenylpyrrolidin-3-ylcarbamate (0.257 g, 0.725 mmol) and TFA (3.91 mL, 50.8 mmol) were heated at 60° C. for 17 hours. The reaction mixture was concentrated in vacuo, using toluene to azeotrope, then treated with 2 N HCl in Et$_2$O and concentrated again to give the title compound (0.21 g, 100% yield) as an off-white solid. MS (apci) m/z=221.2 (M+H).

Preparation E-100

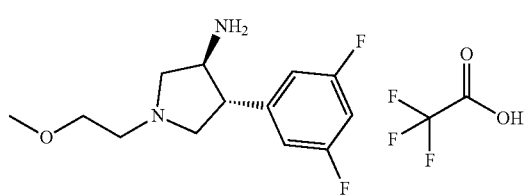

(3S,4R)-4-(3,5-difluorophenyl)-1-(2-methoxyethyl) pyrrolidin-3-amine trifluoroacetate Step A: Preparation of (R,E)-3-(3-(3,5-difluorophenyl)acryloyl)-4-phenyloxazolidin-2-one To a solution of (E)-3-(3,5-difluorophenyl)acrylic acid (10.0 g, 54.3 mmol) in Et$_2$O (150 mL) at 0° C. was added DIEA (9.48 mL, 54.3 mmol) followed by pivaloyl chloride (6.69 mL, 54.3 mmol). The mixture was stirred at 0° C. for 1 hour and cooled to −78° C. Meanwhile (R)-4-phenyloxazolidin-2-one (8.86 g, 54.3 mmol) in THF (200 mL) was cooled to −78° C. and butyllithium (21.7 mL, 2.5 M, 54.3 mmol) was added slowly. The mixture was stirred for 20 minutes at −78° C. and transferred by cannula to the solution of mixed anhydride. The combined mixture was stirred at −78° C. for 15 min, allowed to warm to 0° C. and stirred for an additional 30 minutes. The reaction mixture was quenched with saturated NH$_4$Cl (25 mL), diluted with EtOAc (600 mL), washed with water, NaHCO$_3$, and brine, dried over MgSO$_4$, and concentrated in vacuo. The crude material was purified by silica column chromatography, eluting with 10-20% Ethyl acetate/Hexanes to afford the product (11.0 g, 61.5% yield).

Step B: Preparation of (3S,4R)-4-(3,5-difluorophenyl)-1-(2-methoxyethyl)pyrrolidin-3-amine trifluoroacetic acid salt Prepared by the methods described in Preparation D-100, Steps B through E, replacing (R)-3-cinnamoyl-4-phenyloxazolidin-2-one with (R,E)-3-(3-(3,5-difluorophenyl)acryloyl)-4-phenyloxazolidin-2-one to afford the title compound (1.70 g, 102% yield). MS (apci) m/z=257.2 (M+H).

Preparation F-100

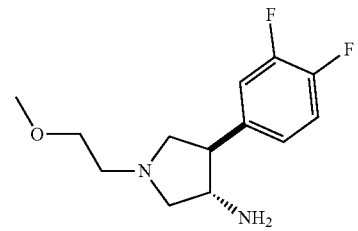 [SMILES: COCCN1C[C@@H](N)[C@H](c2ccc(F)c(F)c2)C1]

(3S,4R)-4-(3,4-difluorophenyl)-1-(2-methoxyethyl) pyrrolidin-3-amine

Prepared according to the method described in Preparation D-100, replacing cinnamoyl chloride with (E)-3-(3,4-difluorophenyl)acryloyl chloride. MS (apci) m/z=257.1 (M+H).

Preparation G-100

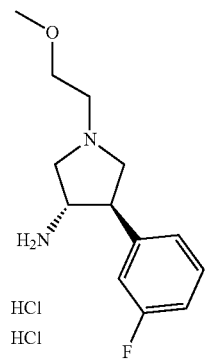 [SMILES: COCCN1C[C@@H](N)[C@H](c2cccc(F)c2)C1 ; Cl ; Cl]

(3S,4R)-1-(2-methoxyethyl)-4-(3-(trifluoromethyl)phenyl)pyrrolidin-3-amine dihydrochloride

Step A: Preparation of tert-butyl (3S,4R)-1-(2-methoxyethyl)-4-(3-(trifluoromethyl)-phenyl)pyrrolidin-3-ylcarbamate A solution of tert-butyl (3S,4R)-4-(3-(trifluoromethyl)phenyl)-pyrrolidin-3-ylcarbamate (100 mg, 0.303 mmol, commercially available), N,N-diethylpropan-2-amine (0.145 mL, 0.908 mmol) and 1-bromo-2-methoxyethane (0.0361 mL, 0.363 mmol) in DMF (1 mL) was stirred at ambient temperature for 2 hours, then heated to 60° C. for 4 hours, then cooled to ambient temperature overnight. After partitioning between EtOAc and saturated NaHCO₃ (10 mL each), the organic layer was washed with water and brine (2×10 mL each), dried over Na₂SO₄, filtered and concentrated to yield the crude product as white solid (80 mg, 68% yield). LCMS (apci) m/z=389.1 (M+H).

Step B: Preparation of (3S,4R)-1-(2-methoxyethyl)-4-(3-(trifluoromethyl)phenyl)-pyrrolidin-3-amine dihydrochloride A solution of tert-butyl (3S,4R)-1-(2-methoxyethyl)-4-(3-(trifluoromethyl)phenyl)pyrrolidin-3-ylcarbamate (80.0 mg, 0.206 mmol) in 5-6 N HCl in IPA (4.12 mL, 20.6 mmol) was stirred at ambient temperature for 1 hour, followed by concentrating in vacuo and triturating with Et₂O to afford the product as beige solid (74 mg, 99.5% yield). LCMS (apci) m/z=289.1 (M+H).

Preparation 11-100

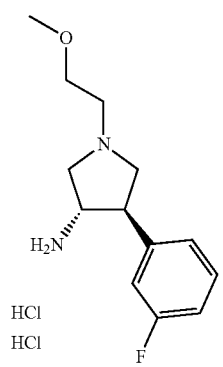 [SMILES: Cl ; Cl ; COCCN1C[C@@H](N)[C@H](c2cccc(F)c2)C1]

(3S,4R)-4-(3-fluorophenyl)-1-(2-methoxyethyl)pyrrolidin-3-amine dihydrochloride

Prepared according to the method of Preparation G-100, replacing tert-butyl (3S,4R)-4-(3-(trifluoromethyl)phenyl)-pyrrolidin-3-ylcarbamate with tert-butyl (3S,4R)-4-(3-fluorophenyl)pyrrolidin-3-ylcarbamate to afford the title compound. LCMS (apci) m/z=239.1 (M+H).

Preparation I-100

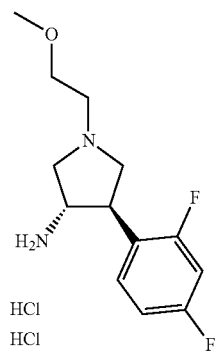 [SMILES: COCCN1C[C@@H](N)[C@H](c2ccc(F)cc2F)C1 ; Cl ; Cl]

(3S,4R)-4-(2,4-difluorophenyl)-1-(2-methoxyethyl)pyrrolidin-3-amine dihydrochloride Prepared according to the method of Preparation G-100, replacing tert-butyl (3S,4R)-4-(3-(trifluoromethyl)phenyl)-pyrrolidin-3-ylcarbamate with tert-butyl (3S,4R)-4-(2,4-di-fluoro-phenyl)pyrrolidin-3-ylcarbamate to afford the title compound. LCMS (apci) m/z=257.1 (M+H).

Preparation J-100

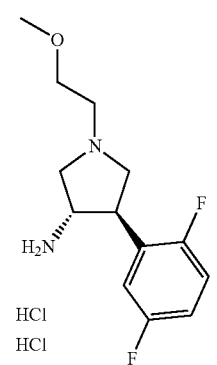 [SMILES: COCCN1C[C@@H](N)[C@H](c2cc(F)ccc2F)C1 ; Cl ; Cl]

(3S,4R)-4-(2,5-difluorophenyl)-1-(2-methoxyethyl)pyrrolidin-3-amine dihydrochloride Prepared according to the method of Preparation G-100, replacing tert-butyl (3S,4R)-4-(3-(trifluoromethyl)phenyl)-pyrrolidin-3-ylcarbamate with tert-butyl (3S,4R)-4-(2,5-di-fluoro-phenyl)pyrrolidin-3-ylcarbamate to afford the title compound. LCMS (apci) m/z=257.1 (M+H).

Preparation K-100

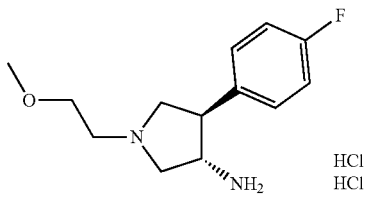 [SMILES: COCCN1C[C@@H](N)[C@H](c2ccc(F)cc2)C1]

(3S,4R)-4-(4-fluorophenyl)-1-(2-methoxyethyl)pyrrolidin-3-amine dihydrochloride Prepared according to the method described in Preparation D-100, replacing cinnamoyl chloride with (E)-3-(4-fluorophenyl)acryloyl chloride. MS (apci) m/z=239.1 (M+H).

The following pyrrolidine intermediates were made according to the method of Preparation B1, Steps A-C, using the appropriate benzaldehyde in Step A and replacing EtOH and platinum(IV) oxide with MeOH and Raney nickel respectively in Step C.

| Preparation # | Structure | Name | Data |
|---|---|---|---|
| L-101 | 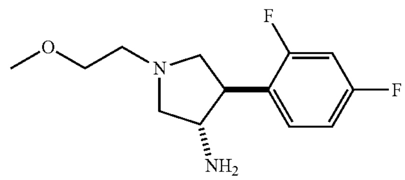 [SMILES: COCCN1C[C@@H](N)[C@H](c2ccc(F)cc2F)C1] | trans-4-(2,4-difluorophenyl)-1-(2-methoxyethyl)pyrrolidin-3-amine | MS (apci) m/z = 256.1 (M + H) |
| L-102 | 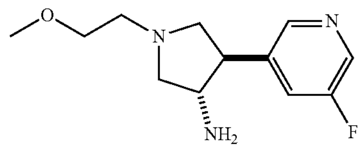 [SMILES: COCCN1C[C@@H](N)[C@H](c2cncc(F)c2)C1] | trans-4-(5-fluoropyridin-3-yl)-1-(2-methoxyethyl)pyrrolidin-3-amine | MS (apci) m/z = 240.1 (M + H) |
| L-103 | 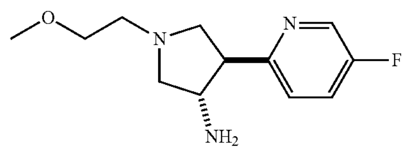 | trans-4-(5-fluoropyridin-2-yl)-1-(2-methoxyethyl)pyrrolidin-3-amine | $^1$H NMR consistent with expected product |
| L-104 | 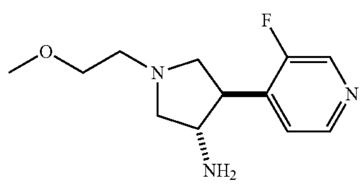 [SMILES: COCCN1C[C@@H](N)[C@H](c2ccncc2F)C1] | trans-4-(3-fluoropyridin-4-yl)-1-(2-methoxyethyl)pyrrolidin-3-amine | Not available |
| L-105 | 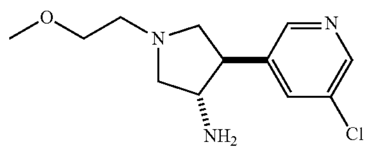 [SMILES: COCCN1C[C@@H](N)[C@H](c2cncc(Cl)c2)C1] | trans-4-(5-chloropyridin-3-yl)-1-(2-methoxyethyl)pyrrolidin-3-amine | MS (apci) m/z = 256.1 (M + H) |
| L-106 | 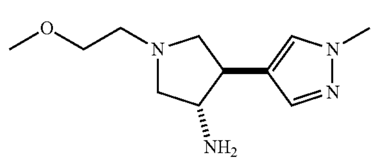 | trans-1-(2-methoxyethyl)-4-(1-methyl-1H-pyrazol-4-yl)pyrrolidin-3-amine | $^1$H NMR consistent with expected product |
| L-107 | 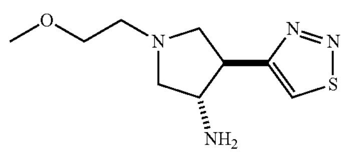 | trans-1-(2-methoxyethyl)-4-(1,2,3-thiadiazol-4-yl)pyrrolidin-3-amine | Not available |

Preparation L-108

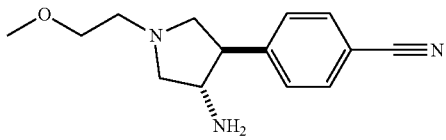

4-(trans-4-amino-1-(2-methoxyethyl)pyrrolidin-3-yl)benzonitrile

Prepared according to the method described in Preparation B1, Steps A to C, replacing 4-fluorobenzaldehyde with 4-formylbenzonitrile in Step A and replacing EtOH and platinum(IV) oxide with MeOH, Zn (dust) and saturated NH₄Cl, respectively in Step C. MS (apci) m/z=246.1 (M+H).

Preparation L-109

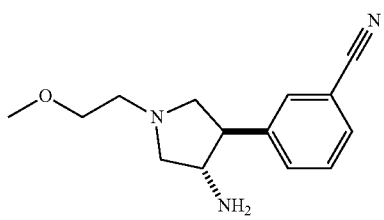 [SMILES: COCCN1C[C@@H](N)[C@H](c2cccc(C#N)c2)C1]

3-(trans-4-amino-1-(2-methoxyethyl)pyrrolidin-3-yl)benzonitrile

Prepared according to the method described in Preparation B1, Steps A to C, replacing 4-fluorobenzaldehyde with 3-formylbenzonitrile in Step A, and replacing EtOH and platinum(IV) oxide with MeOH, Zn (dust) and saturated NH₄Cl, respectively, in Step C. MS (apci) m/z=246.2 (M+H).

Preparation N-100

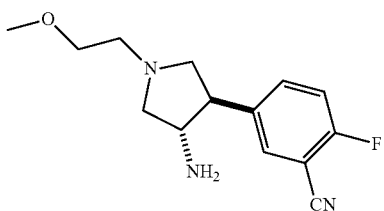 [SMILES: COCCN1C[C@@H](N)[C@H](c2ccc(F)c(C#N)c2)C1]

Trans-5-(4-amino-1-(2-methoxyethyl)pyrrolidin-3-yl)-2-fluorobenzonitrile

Step A: (E)-2-fluoro-5-(2-nitrovinyl)benzonitrile

To a solution of 2-fluoro-5-formylbenzonitrile (3.84 g, 25.0 mmol) in 3:1 CH₃NO₂/CH₃CN (25 mL) was added DMAP (0.305 g, 2.50 mmol) and the mixture stirred at ambient temperature for 23 hours. The mixture was cooled on an ice bath and Ac₂O (3.54 mL, 37.5 mmol) was added. The mixture was stirred for 5 minutes, allowed to reach ambient temperature and stirred for 1 hour. The mixture was concentrated to a yellow solid. The solid was suspended in iPrOH (70 mL) and stirred for 10 minutes. The suspension was collected via vacuum filtration, the cake washed with iPrOH and dried in vacuum to afford the title compound as a light tan powder (3.36 g, 70%). ¹H NMR (CDCl₃) δ 7.96 (d, 1H), 7.79-7.88 (m, 2H), 7.57 (d, 1H), 7.36 (t, 1H).

Step B: Trans-2-fluoro-5-(1-(2-methoxyethyl)-4-nitropyrrolidin-3-yl)benzonitrile Using (E)-2-fluoro-5-(2-nitrovinyl)benzonitrile in Step B of the procedure describe in Preparation B1, the title compound was prepared as light gold syrup (1.56 g, 53%). MS (apci) m/z=294.1 (M+H).

Step C: Trans-5-(4-amino-1-(2-methoxyethyl)pyrrolidin-3-yl)-2-fluorobenzonitrile A solution of trans-2-fluoro-5-(1-(2-methoxyethyl)-4-nitropyrrolidin-3-yl)benzonitrile (450 mg, 1.53 mmol) in MeOH (6.0 mL) was cooled to 0°. Zn dust (1.00 mg, 15.3 mmol) and saturated aqueous NH₄Cl (1.0 mL) were added sequentially and the mixture was stirred for 5 minutes. The mixture was allowed to reach ambient temperature and stirred until complete by LCMS analysis. The mixture was filtered through packed Celite® using MeOH for rinsing and elution and the filtrate was concentrated to a colorless syrup. The syrup was treated with 1M K₂CO₃ (15 mL), mixed and extracted with CH₂Cl₂ (3×). The combined CH₂Cl₂ extracts were dried over Na₂SO₄, filtered and concentrated to provide the title compound as a colorless syrup (412 mg, 100%). MS (apci) m/z=264.1 (M+H).

Preparation O-100

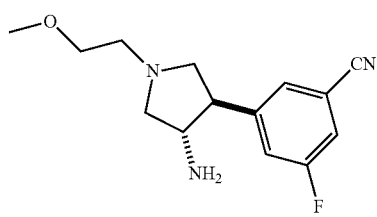 [SMILES: COCCN1C[C@@H](N)[C@H](c2cc(F)cc(C#N)c2)C1]

Trans-3-(4-amino-1-(2-methoxyethyl)pyrrolidin-3-yl)-5-fluorobenzonitrile

Step A: 3-fluoro-5-formylbenzonitrile

A solution of 3-bromo-5-fluorobenzonitrile (5.00 g, 25.0 mmol) in dry THF (25 mL) was cooled to 0° C. and 2M iPrMgCl (15.0 mL, 30.0 mmol) in THF was added dropwise over 5 minutes. The mixture was stirred at 0° C. for 15 minutes then at ambient temperature for 1 hour. The mixture was cooled to 0° C. and dry DMF (5.81 mL, 75.0 mmol) was added. The mixture was stirred for 17 hours during which time the temperature reached ambient temperature after 2 hours. The mixture was added to ice water (150 mL) and Et₂O (100 mL). The biphasic mixture was stirred and treated with 6M HCl to aqueous pH=3. The organic layer was removed and the aqueous layer extracted with Et₂O (2×). The combined Et₂O fractions were washed with saturated NaCl and dried over MgSO₄/activated carbon. The dried solution was filtered through a SiO₂ plug eluting with Et₂O. The filtrate was concentrated to give the title compound as a yellow solid that was dried in vacuum (3.68 g, 99%). ¹H NMR (CDCl₃) δ 10.0 (s, 1H), 8.00 (s, 1H), 7.81-7.86 (m, 1H), 7.62-7.67 (m, 1H).

Step B: Trans-3-(4-amino-1-(2-methoxyethyl)pyrrolidin-3-yl)-5-fluorobenzonitrile The tile compound was prepared using 3-fluoro-5-formylbenzonitrile in the procedure described for the preparation of trans-5-(4-amino-1-(2-methoxyethyl)pyrrolidin-3-yl)-2-fluorobenzonitrile (Preparation N-100). The compound was isolated as a colorless syrup (542 mg, 93%). MS (apci) m/z=264.1 (M+H).

Preparation P-100

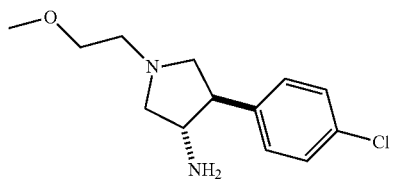 [SMILES: COCCN1C[C@@H](N)[C@H](c2ccc(Cl)cc2)C1]

Trans-1-(2-methoxyethyl)-4-(4-chlorophenyl)pyrrolidin-3-amine

Step A: Trans-3-(4-chlorophenyl)-1-(2-methoxyethyl)-4-nitropyrrolidine

Using (E)-1-chloro-4-(2-nitrovinyl)benzene in Step B of the procedure describe in Preparation B1, the title compound was prepared as viscous colorless oil (5.10 g, 64%). MS (apci) m/z=285.0 (M+H).

Step B: Trans-1-(2-methoxyethyl)-4-(4-chlorophenyl)pyrrolidin-3-amine

To a suspension of 2800 Raney Nickel (50 wt % in H₂O, 0.873 g, 5.10 mmol) in MeOH (25 mL) was added trans-3-(4-chlorophenyl)-1-(2-methoxyethyl)-4-nitropyrrolidine (2.90 g, 10.2 mmol) in MeOH (25 mL). The mixture was flushed with H₂ gas and stirred under a balloon atmosphere of H₂ for 16 hours. The mixture was purged with N₂ gas and filtered through packed Celite® using MeOH for rinsing and elution. The filtrate was concentrated to a cloudy oil. The oil was dissolved in CH₂Cl₂ and dried over Na₂SO₄/activated carbon. The solution was filtered and concentrated to provide the title compound as a light gold oil that was dried in vacuum (2.46 g, 95%). MS (apci) m/z=255.1 (M+H).

Preparation E

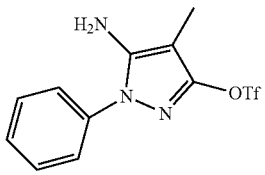 [SMILES: Cc1c(OS(=O)(=O)C(F)(F)F)nn(-c2ccccc2)c1N]

5-amino-4-methyl-1-phenyl-1H-pyrazol-3-yl trifluoromethanesulfonate

Step A: Preparation of 5-amino-4-methyl-1-phenyl-1H-pyrazol-3(2H)-one

A mixture of ethyl 2-cyanopropanoate (50.5 g, 397.2 mmol) and phenylhydrazine (39 mL, 397.2 mmol) in dioxane (100 mL) was heated at 110° C. for 5 days. The cooled mixture was concentrated to ½ volume then cooled in ice and triturated with cold Et₂O. Solids were filtered, washed extensively with Et₂O and dried in vacuo to afford 5-amino-4-methyl-1-phenyl-1H-pyrazol-3(2H)-one (34.69 g, 46% yield) as a fluffy white powder. MS (apci) m/z=190.1 (M+H).

Step B: Preparation of 5-amino-4-methyl-1-phenyl-1H-pyrazol-3-yl trifluoromethane sulfonate A suspension of 5-amino-4-methyl-1-phenyl-1H-pyrazol-3(2H)-one (13.72 g, 72.5 mmol) and N-phenylbis(trifluoromethylsulfonamide) (27.2 g, 76.1 mmol) in DMF (100 mL) was treated with DIEA (37.9 mL, 217.5 mmol) and the mixture stirred at ambient temperature for 16 hours. The mixture was partitioned between saturated NaHCO₃ (400 mL) and EtOAc (200 mL) and the aqueous layer was extracted with EtOAc (2×200 mL). The combined organic phases were washed with water (5×50 mL) and brine (50 mL) then dried over Na₂SO₄, filtered and concentrated in vacuo. The residue was purified by silica column chromatography eluting with 4:1 hexanes/EtOAc, to afford the title compound (23.1 g, 99% yield) as a pale yellow solid. MS (apci) m/z=322.0 (M+H).

Preparation F

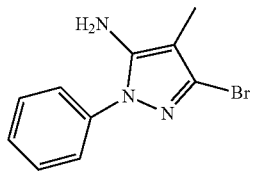

3-bromo-4-methyl-1-phenyl-1H-pyrazol-5-amine

To a suspension of 5-amino-4-methyl-1-phenyl-1H-pyrazol-3(2H)-one [Preparation E, step A] (1.60 g, 8.46 mmol) in acetonitrile (30 mL) was added phosphorus oxybromide (3.64 g, 12.7 mmol) in one portion. The mixture was stirred at reflux for 3 hours then cooled and concentrated in vacuo. The residue was treated with DCM (50 mL) then saturated NaHCO$_3$ (50 mL) was slowly added. The mixture was stirred for 30 minutes then the layers separated and the aqueous layer extracted with DCM (2×50 mL). The combined organic phases were washed with brine (20 mL), dried over Na$_2$SO$_4$, filtered and concentrated in vacuo. The residue was purified by silica column chromatography eluting with 2:1 hexanes/EtOAc, to afford the title compound (273 mg, 13% yield) as a white solid. MS (apci) m/z=254.0 (M+H).

Preparation G

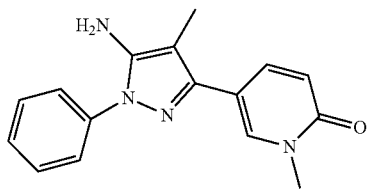 [SMILES: Cc1c(-c2ccc(=O)n(C)c2)nn(-c2ccccc2)c1N]

5-(5-amino-4-methyl-1-phenyl-1H-pyrazol-3-yl)-1-methylpyridin-2 (1H)-one 3-bromo-4-methyl-1-phenyl-1H-pyrazol-5-amine [Preparation F] (763 mg, 3.03 mmol), 1-methyl-5-(4,4,5,5-tetramethyl-1,3,2-dioxaborolan-2-yl)pyridin-2(1H)one (1.42 g, 6.05 mmol), K$_2$CO$_3$ (1.67 g, 12.1 mmol) and Pd(PPh$_3$)$_4$ (350 mg, 0.30 mmol) were combined in toluene (10 mL), water (5 mL) and EtOH (2.5 mL) and warmed to 95° C. in a sealed tube for 16 hours. The cooled mixture was filtered and the filtrate partitioned between water (30 mL) and EtOAc (30 mL). The aqueous layer was extracted with EtOAc (2×20 mL) and the combined organic phases were washed with brine (20 mL), dried over Na$_2$SO$_4$, filtered and concentrated in vacuo. The residue was purified by silica column chromatography eluting with 2% MeOH/DCM to afford the title compound (504 mg, 59% yield) as a yellow foam. MS (apci) m/z=281.2 (M+H).

Preparation H

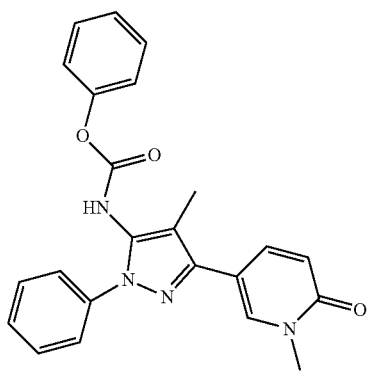 [SMILES: Cc1c(-c2ccc(=O)n(C)c2)nn(-c2ccccc2)c1NC(=O)Oc1ccccc1]

phenyl(4-methyl-3-(1-methyl-6-oxo-1,6-dihydro-pyridin-3-yl)-1-phenyl-1H-pyrazol-5-yl)carbamate To a suspension of 5-(5-amino-4-methyl-1-phenyl-1H-pyrazol-3-yl)-1-methylpyridin-2(1H)-one [Preparation G] (2.80 g, 9.99 mmol) in EtOAc (120 mL) was added 2N NaOH (14.98 mL, 29.97 mmol) followed by phenyl chloroformate (2.5 mL, 19.98 mmol). The mixture was stirred at ambient temperature for 16 hours then partitioned between water (100 mL) and EtOAc (100 mL) and the aqueous layer extracted with EtOAc (2×50 mL). The combined organic phases were washed with saturated NaHCO$_3$ (50 mL) and brine (50 mL), then dried over Na$_2$SO$_4$, filtered and concentrated to afford the title compound as a pale yellow syrup which was used directly without purification, assuming 100% yield. MS (apci) m/z=401.2 (M+H).

SYNTHETIC EXAMPLES

Example 1

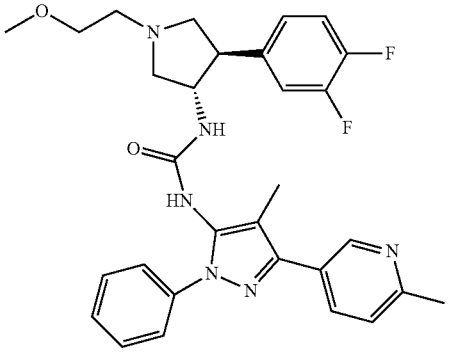

1-((3S,4R)-4-(3,4-difluorophenyl)-1-(2-methoxy-ethyl)pyrrolidin-3-yl)-3-(4-methyl-3-(6-methylpyri-din-3-yl)-1-phenyl-1H-pyrazol-5-yl)urea Step A: Preparation of 4-methyl-3-(6-methylpyri-din-3-yl)-1-phenyl-1H-pyrazol-5-amine 5-Amino-4-methyl-1-phenyl-1H-pyrazol-3-yl trifluoromethane sulfonate [Preparation E] (1.01 g, 3.11 mmol), (6-methylpyridin-3-yl)boronic acid (639 mg, 4.67 mmol), K$_2$CO$_3$ (1.72 g, 12.45 mmol) and Pd(PPh$_3$)$_4$ (360 mg, 0.31 mmol) were combined in toluene (10 mL), water (5 mL) and EtOH (2.5 mL) and stirred at 95° C. in a sealed tube for 18 hours. The cooled mixture was filtered through GF paper and the filtrate partitioned between water (50 mL) and EtOAc (50 mL). The aqueous layer was extracted with EtOAc (2×30 mL) and the combined organic phases were washed with brine (30 mL), dried over Na$_2$SO$_4$, filtered and concentrated in vacuo. The residue was purified by silica column chromatography eluting with 2% MeOH/DCM to afford 4-methyl-3-(6-methylpyridin-3-yl)-1-phenyl-1H-pyrazol-5-amine (529 mg, 64% yield) as a red solid. MS (apci) m/z=265.1 (M+H).

Step B: Preparation of 1-((3S,4R)-4-(3,4-difluoro-phenyl)-1-(2-methoxyethyl)pyrrolidin-3-yl)-3-(4-methyl-3-(6-methylpyridin-3-yl)-1-phenyl-1H-pyra-zol-5-yl)urea To a solution of 4-methyl-3-(6-methylpyridin-3-yl)-1-phenyl-1H-pyrazol-5-amine (40 mg, 0.15 mmol) in DCM (2 mL) was added triphosgene (22 mg, 0.07 mmol) followed by DIEA (79 µL, 0.46 mmol). The solution was stirred for 30 minutes at ambient temperature then treated with (3S,4R)-4-(3,4-difluorophenyl)-1-(2-methoxyethyl)pyrrolidin-3-amine [Preparation B3] (50 mg, 0.15 mmol) and DIEA (79 ΞL, 0.46 mmol). After stirring at ambient temperature for 16 hours the mixture was partitioned between saturated NH₄Cl (10 mL) and DCM (10 mL) and the aqueous layer extracted with DCM (2×10 mL). The combined organic phases were washed with brine (10 mL), dried over Na₂SO₄, filtered and concentrated in vacuo. The residue was purified by silica column chromatography eluting with 2.5-5% MeOH/DCM to afford the title compound (63 mg, 76% yield) as a pale yellow solid. MS (apci) m/z=547.2 (M+H).

Example 2

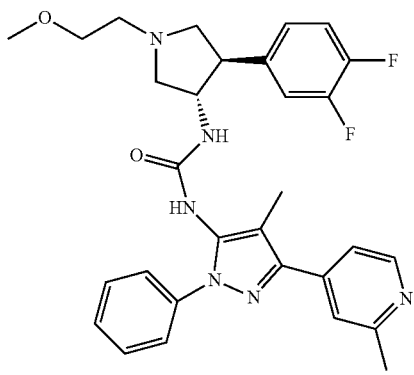 [SMILES: COCCN1C[C@@H](NC(=O)Nc2c(C)c(-c3ccnc(C)c3)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(4-methyl-3-(2-methylpyridin-4-yl)-1-phenyl-1H-pyrazol-5-yl)urea Prepared according to the procedure of Example 1, replacing (6-methylpyridin-3-yl)boronic acid with (2-methylpyridin-4-yl)boronic acid in Step A. The crude material was purified by silica column chromatography eluting with 3-5% MeOH/DCM, then reverse phase HPLC (5-95% ACN/water/0.1% TFA) to afford the title compound (27 mg, 16% yield) as a white solid. MS (apci) m/z=547.3 (M+H).

Example 3

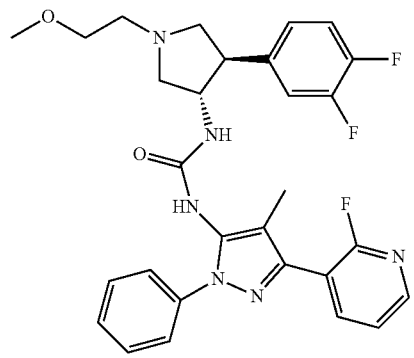 [SMILES: COCCN1C[C@@H](NC(=O)Nc2c(C)c(-c3cccnc3F)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(3-(2-fluoropyridin-3-yl)-4-methyl-1-phenyl-1H-pyrazol-5-yl)urea Prepared according to the procedure of Example 1, replacing (6-methylpyridin-3-yl)boronic acid with (2-fluoropyridin-3-yl)boronic acid in Step A. The crude material was purified by silica column chromatography eluting with 1-2.5% MeOH/DCM to afford the title compound (69 mg, 75% yield) as a cream solid. MS (apci) m/z=551.2 (M+H).

Example 4

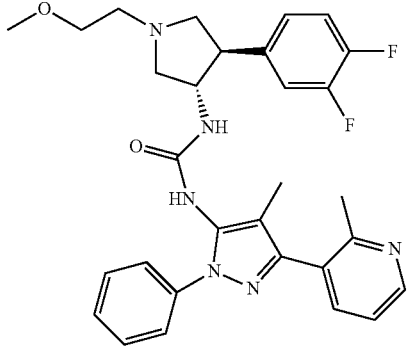 [SMILES: COCCN1C[C@@H](NC(=O)Nc2c(C)c(-c3cccnc3C)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(4-methyl-3-(2-methylpyridin-3-yl)-1-phenyl-1H-pyrazol-5-yl)urea Prepared according to the procedure of Example 1, replacing (6-methylpyridin-3-yl)boronic acid with (2-methylpyridin-3-yl)boronic acid in Step A. The crude material was purified by silica column chromatography eluting with 2-5% MeOH/DCM to afford the title compound (70 mg, 68% yield) as a colorless gum. MS (apci) m/z=547.3 (M+H).

Example 5

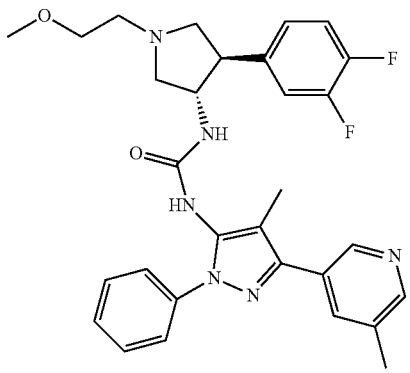 [SMILES: COCCN1C[C@@H](NC(=O)Nc2c(C)c(-c3cncc(C)c3)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(4-methyl-3-(5-methylpyridin-3-yl)-1-phenyl-1H-pyrazol-5-yl)urea Prepared according to the procedure of Example 1, replacing (6-methylpyridin-3-yl)boronic acid with (5-methylpyridin-3-yl)boronic acid in Step A. The crude material was purified by silica column chromatography eluting with 2.5% MeOH/DCM to afford the title compound (51 mg, 49% yield) as a white solid. MS (apci) m/z=547.2 (M+H).

Example 6

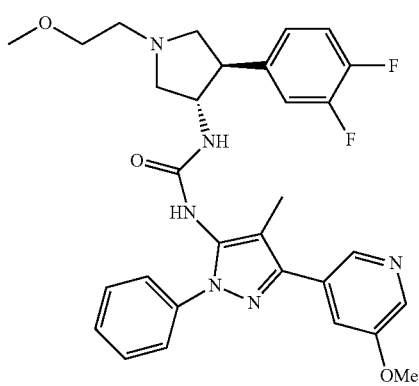 [SMILES: COCCN1C[C@@H](NC(=O)Nc2c(C)c(-c3cncc(OC)c3)nn2-c2ccccc2)[C@H](c2ccc(F)c(F)c2)C1]

1-((3S,4R)-4-(3,4-difluorophenyl)-1-(2-methoxy-ethyl)pyrrolidin-3-yl)-3-(3-(5-methoxypyridin-3-yl)-4-methyl-1-phenyl-1H-pyrazol-5-yl)urea Prepared according to the procedure of Example 1, replacing (6-methylpyridin-3-yl)boronic acid with (5-methoxypyridin-3-yl)boronic acid in Step A. The crude material was purified by silica column chromatography eluting with 2.5% MeOH/DCM to afford the title compound (51 mg, 49% yield) as a white solid. MS (apci) m/z=547.2 (M+H).

Example 7

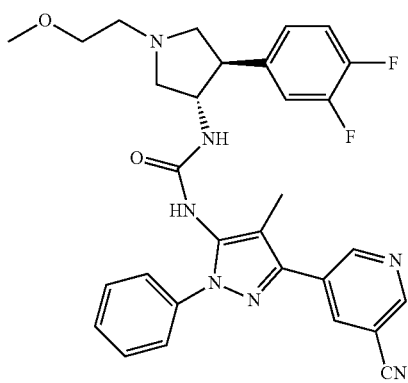 [SMILES: COCCN1C[C@@H](NC(=O)Nc2c(C)c(-c3cncc(C#N)c3)nn2-c2ccccc2)[C@H](c2ccc(F)c(F)c2)C1]

1-(3-(5-cyanopyridin-3-yl)-4-methyl-1-phenyl-1H-pyrazol-5-yl)-3-((3S,4R)-4-(3,4-difluorophenyl)-1-(2-methoxyethyl)pyrrolidin-3-yl)urea Prepared according to the procedure of Example 1, replacing (6-methylpyridin-3-yl)boronic acid with 5-(4,4,5,5-tetramethyl-1,3,2-dioxaborolan-2-yl)nicotinonitrile in Step A. The crude material was purified by silica column chromatography eluting with 2% MeOH/DCM to afford the title compound (70 mg, 69% yield) as a pale pink solid. MS (apci) m/z=558.2 (M+H).

Example 8

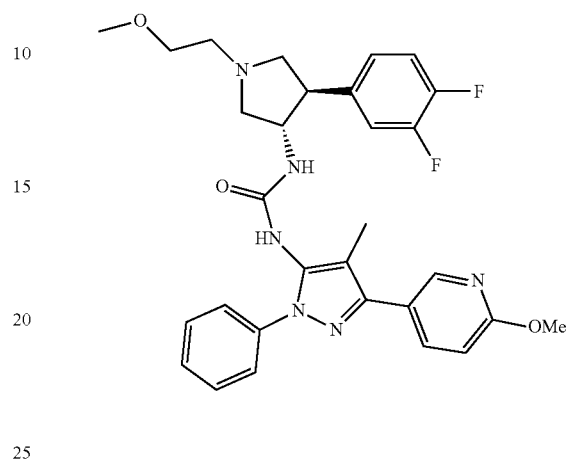

1-((3S,4R)-4-(3,4-difluorophenyl)-1-(2-methoxy-ethyl)pyrrolidin-3-yl)-3-(3-(6-methoxypyridin-3-yl)-4-methyl-1-phenyl-1H-pyrazol-5-yl)urea Prepared according to the procedure of Example 1, replacing (6-methylpyridin-3-yl)boronic acid with (6-methoxypyridin-3-yl)boronic acid in Step A. The crude material was purified by silica column chromatography eluting with 2.5% MeOH/DCM to afford the title compound (31 mg, 31% yield) as a white solid. MS (apci) m/z=563.3 (M+H).

Example 9

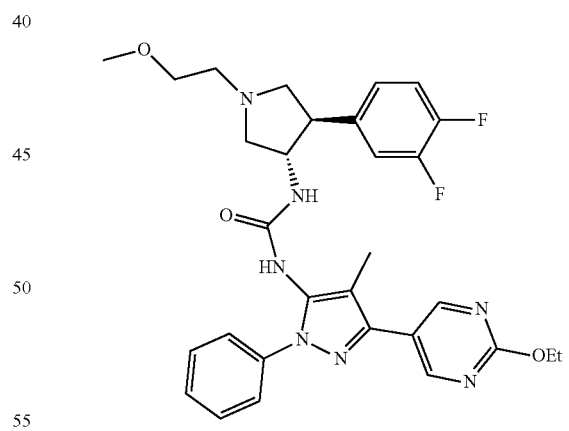

1-((3S,4R)-4-(3,4-difluorophenyl)-1-(2-methoxy-ethyl)pyrrolidin-3-yl)-3-(3-(2-ethoxypyrimidin-5-yl)-4-methyl-1-phenyl-1H-pyrazol-5-yl)urea Prepared according to the procedure of Example 1, replacing (6-methylpyridin-3-yl)boronic acid with (2-ethoxypyrimidin-5-yl)boronic acid in Step A. The crude material was purified by silica column chromatography eluting with 2-4% MeOH/DCM to afford the title compound (42 mg, 43% yield) as a white solid. MS (apci) m/z=578.3 (M+H).

Example 10

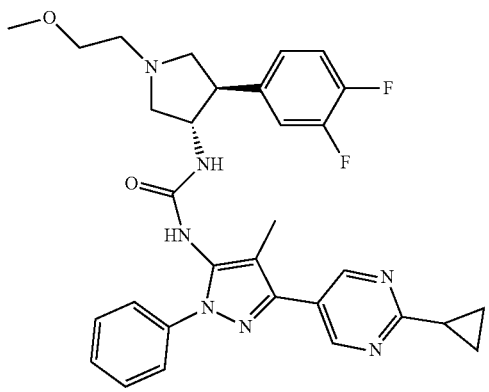 [SMILES: COCCN1C[C@@H](NC(=O)Nc2c(C)c(-c3cnc(C4CC4)nc3)nn2-c2ccccc2)[C@H](c2ccc(F)c(F)c2)C1]

1-(3-(2-cyclopropylpyrimidin-5-yl)-4-methyl-1-phenyl-1H-pyrazol-5-yl)-3-((3S,4R)-4-(3,4-difluorophenyl)-1-(2-methoxyethyl)pyrrolidin-3-yl)urea Prepared according to the procedure of Example 1, replacing (6-methylpyridin-3-yl)boronic acid with 2-cyclopropyl-5-(4,4,5,5-tetramethyl-1,3,2-dioxaborolan-2-yl)pyrimidine in Step A. The crude material was purified by silica column chromatography eluting with 2.5-5% MeOH/DCM to afford the title compound (38 mg, 39% yield) as a pale yellow solid. MS (apci) m/z=574.3 (M+H).

Example 11

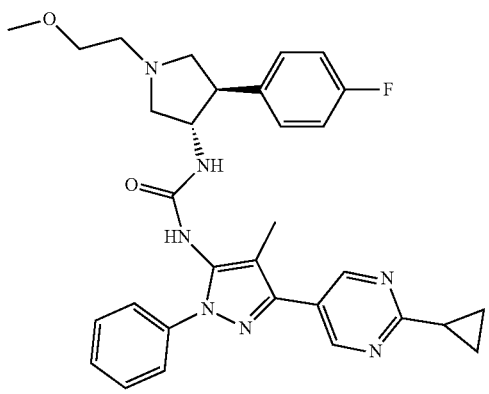 [SMILES: COCCN1C[C@@H](NC(=O)Nc2c(C)c(-c3cnc(C4CC4)nc3)nn2-c2ccccc2)[C@H](c2ccc(F)cc2)C1]

1-(3-(2-cyclopropylpyrimidin-5-yl)-4-methyl-1-phenyl-1H-pyrazol-5-yl)-3-((3S,4R)-4-(4-fluorophenyl)-1-(2-methoxyethyl)pyrrolidin-3-yl)urea Prepared according to the procedure of Example 10, replacing (3S,4R)-4-(3,4-difluorophenyl)-1-(2-methoxyethyl)pyrrolidin-3-amine [Preparation B3] with (3S,4R)-4-(4-fluorophenyl)-1-(2-methoxyethyl)pyrrolidin-3-amine [Preparation B1] in Step B. The crude material was purified by silica column chromatography eluting with 2.5-5% MeOH/DCM to afford the title compound (44 mg, 47% yield) as a pale yellow solid. MS (apci) m/z=556.3 (M+H).

Example 12

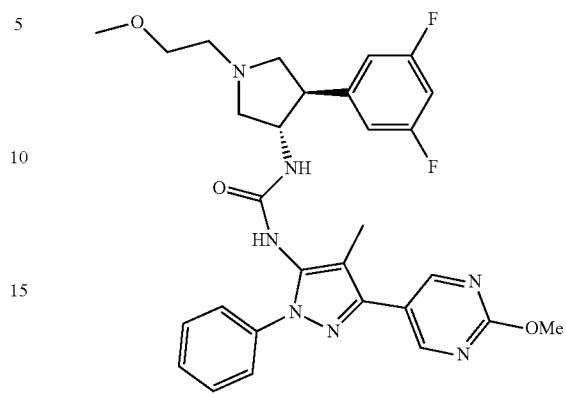

1-((3S,4R)-4-(3,5-difluorophenyl)-1-(2-methoxyethyl)pyrrolidin-3-yl)-3-(3-(2-methoxypyrimidin-5-yl)-4-methyl-1-phenyl-1H-pyrazol-5-yl)urea Prepared according to the procedure of Example 1, replacing (6-methylpyridin-3-yl)boronic acid with (2-methoxypyrimidin-5-yl)boronic acid in Step A and (3S,4R)-4-(3,4-difluorophenyl)-1-(2-methoxyethyl)pyrrolidin-3-amine [Preparation B3] with (3S,4R)-4-(3,5-difluorophenyl)-1-(2-methoxyethyl)pyrrolidin-3-amine [Preparation B2] in Step B. The crude material was purified by silica column chromatography eluting with 2.5-5% MeOH/DCM to afford the title compound (21 mg, 25% yield) as a cream solid. MS (apci) m/z=564.2 (M+H).

Example 13

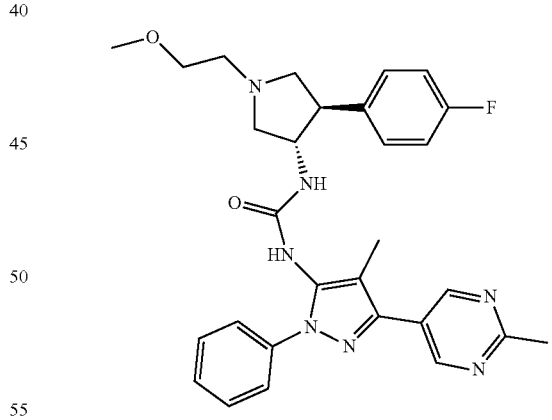

1-((3S,4R)-4-(4-fluorophenyl)-1-(2-methoxyethyl)pyrrolidin-3-yl)-3-(4-methyl-3-(2-methylpyrimidin-5-yl)-1-phenyl-1H-pyrazol-5-yl)urea Prepared according to the procedure of Example 1, replacing (6-methylpyridin-3-yl)boronic acid with 2-methyl-5-(4,4,5,5-tetramethyl-1,3,2-dioxaborolan-2-yl)pyrimidine in Step A and (3S,4R)-4-(3,4-difluorophenyl)-1-(2-methoxyethyl)pyrrolidin-3-amine [Preparation B3] with (3S,4R)-4-(4-fluorophenyl)-1-(2-methoxyethyl)pyrrolidin-3-amine

[Preparation B1] in Step B. The crude material was purified by silica column chromatography eluting with 3-5% MeOH/DCM to afford the title compound (49 mg, 44% yield) as a pale yellow solid. MS (apci) m/z=530.2 (M+H).

Example 14

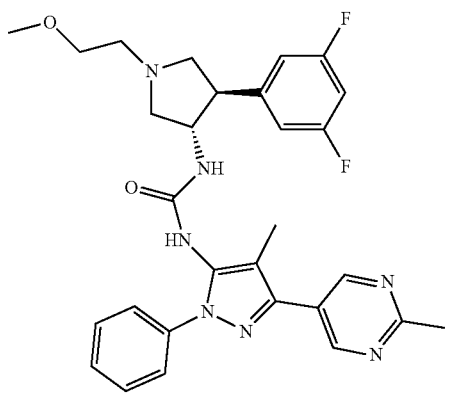

1-((3S,4R)-4-(3,5-difluorophenyl)-1-(2-methoxy-ethyl)pyrrolidin-3-yl)-3-(4-methyl-3-(2-methylpyrimidin-5-yl)-1-phenyl-1H-pyrazol-5-yl)urea Prepared according to the procedure of Example 13, replacing (3S,4R)-4-(3,4-difluorophenyl)-1-(2-methoxyethyl)pyrrolidin-3-amine [Preparation B3] with (3S,4R)-4-(3,5-difluorophenyl)-1-(2-methoxyethyl)pyrrolidin-3-amine [Preparation B2] in Step B. The crude material was purified by silica column chromatography eluting with 3-5% MeOH/DCM to afford the title compound (34 mg, 41% yield) as a cream solid. MS (apci) m/z=548.2 (M+H).

Example 15

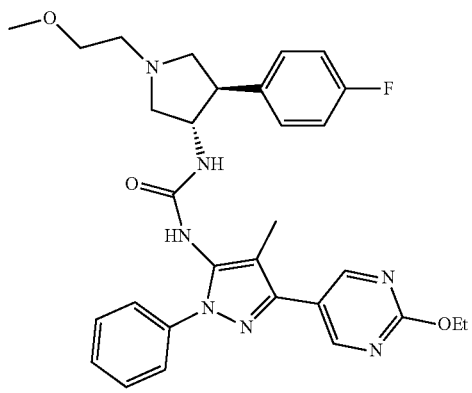 [SMILES: CCOc1ncc(-c2nn(-c3ccccc3)c(NC(=O)N[C@@H]3CN(CCOC)C[C@H]3c3ccc(F)cc3)c2C)cn1]

1-(3-(2-ethoxypyrimidin-5-yl)-4-methyl-1-phenyl-1H-pyrazol-5-yl)-3-((3S,4R)-4-(4-fluorophenyl)-1-(2-methoxyethyl)pyrrolidin-3-yl)urea Prepared according to the procedure of Example 9, replacing (3S,4R)-4-(3,4-difluorophenyl)-1-(2-methoxyethyl)pyrrolidin-3-amine [Preparation B3] with (3S,4R)-4-(4-fluorophenyl)-1-(2-methoxyethyl)pyrrolidin-3-amine [Preparation B1] in Step B. The crude material was purified by silica column chromatography eluting with 2.5% MeOH/DCM to afford the title compound (20 mg, 33% yield) as a white solid. MS (apci) m/z=560.3 (M+H).

Example 16

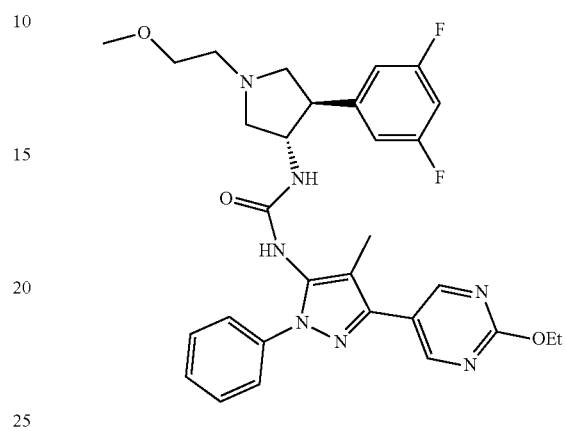

1-((3S,4R)-4-(3,5-difluorophenyl)-1-(2-methoxy-ethyl)pyrrolidin-3-yl)-3-(3-(2-ethoxypyrimidin-5-yl)-4-methyl-1-phenyl-1H-pyrazol-5-yl)urea Prepared according to the procedure of Example 9, replacing (3S,4R)-4-(3,4-difluorophenyl)-1-(2-methoxyethyl)pyrrolidin-3-amine [Preparation B3] with (3S,4R)-4-(3,5-difluorophenyl)-1-(2-methoxyethyl)pyrrolidin-3-amine [Preparation B2] in Step B. The crude material was purified by silica column chromatography eluting with 2.5% MeOH/DCM to afford the title compound (16 mg, 26% yield) as a white solid. MS (apci) m/z=578.3 (M+H).

Example 17

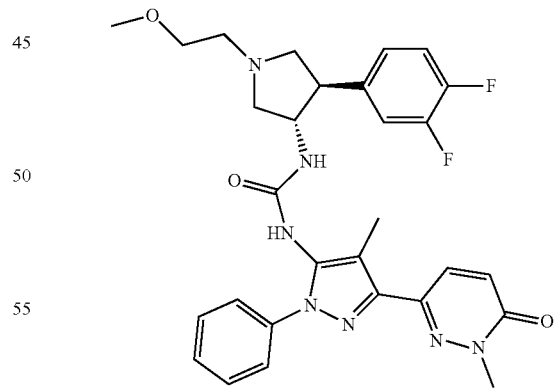

1-((3S,4R)-4-(3,4-difluorophenyl)-1-(2-methoxy-ethyl)pyrrolidin-3-yl)-3-(4-methyl-3-(1-methyl-6-oxo-1,6-dihydropyridazin-3-yl)-1-phenyl-1H-pyrazol-5-yl)urea Prepared according to the procedure of Example 1, replacing (6-methylpyridin-3-yl)boronic acid with 2-methyl-6-(4, 4,5,5-tetramethyl-1,3,2-dioxaborolan-2-yl)pyridazin-3(2H)-one in Step A. The crude material was purified by silica column chromatography eluting with 2-3% MeOH/DCM to afford the title compound (48 mg, 48% yield) as a white solid. MS (apci) m/z=564.3 (M+H).

Example 18

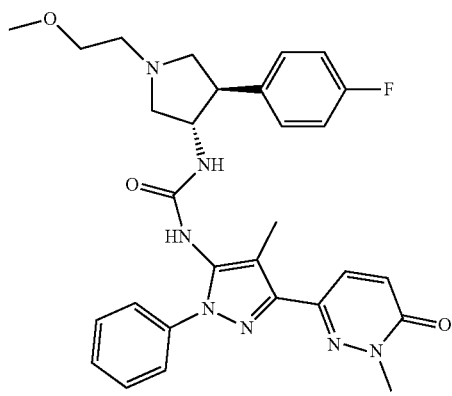 [SMILES: COCCN1C[C@@H](NC(=O)Nc2c(C)c(-c3ccc(=O)n(C)n3)nn2-c2ccccc2)[C@H](c2ccc(F)cc2)C1]

1-((3S,4R)-4-(4-fluorophenyl)-1-(2-methoxyethyl) pyrrolidin-3-yl)-3-(4-methyl-3-(1-methyl-6-oxo-1,6-dihydropyridazin-3-yl)-1-phenyl-1H-pyrazol-5-yl) urea Prepared according to the procedure of Example 17, replacing (3S,4R)-4-(3,4-difluorophenyl)-1-(2-methoxyethyl)pyrrolidin-3-amine [Preparation B3] with (3S,4R)-4-(4-fluorophenyl)-1-(2-methoxyethyl)pyrrolidin-3-amine [Preparation B1] in Step B. The crude material was purified by silica column chromatography eluting with 2.5-4% MeOH/DCM to afford the title compound (32 mg, 41% yield) as a cream solid. MS (apci) m/z=546.2 (M+H).

Example 19

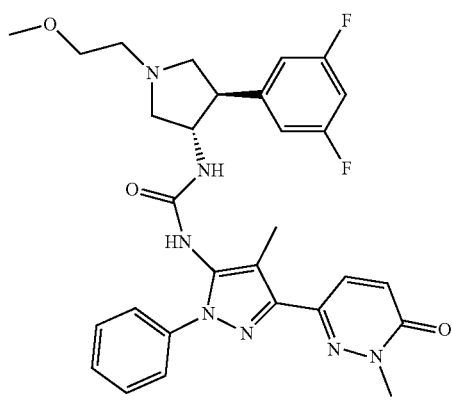 [SMILES: COCCN1C[C@@H](NC(=O)Nc2c(C)c(-c3ccc(=O)n(C)n3)nn2-c2ccccc2)[C@H](c2cc(F)cc(F)c2)C1]

1-((3S,4R)-4-(3,5-difluorophenyl)-1-(2-methoxyethyl)pyrrolidin-3-yl)-3-(4-methyl-3-(1-methyl-6-oxo-1,6-dihydropyridazin-3-yl)-1-phenyl-1H-pyrazol-5-yl)urea Prepared according to the procedure of Example 17, replacing (3S,4R)-4-(3,4-difluorophenyl)-1-(2-methoxyethyl)pyrrolidin-3-amine [Preparation B3] with (3S,4R)-4-(3,5-difluorophenyl)-1-(2-methoxyethyl)pyrrolidin-3-amine [Preparation B2] in Step B. The crude material was purified by silica column chromatography eluting with 2.5% MeOH/DCM to afford the title compound (25 mg, 31% yield) as a white solid. MS (apci) m/z=564.2 (M+H).

Example 20

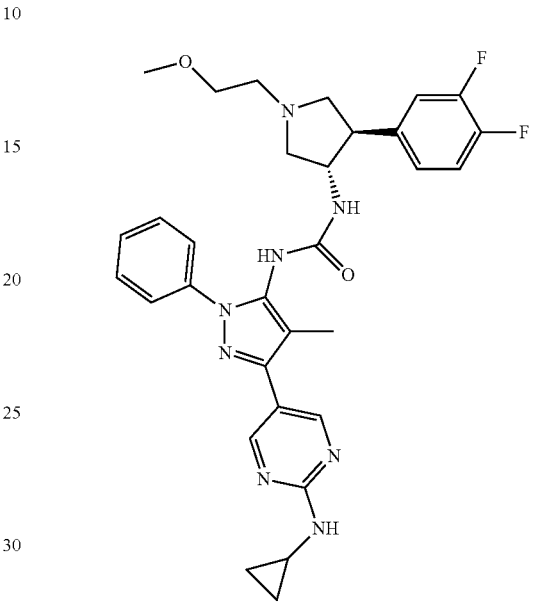

1-(3-(2-(cyclopropylamino)pyrimidin-5-yl)-4-methyl-1-phenyl-1H-pyrazol-5-yl)-3-((3S,4R)-4-(3,4-difluorophenyl)-1-(2-methoxyethyl)pyrrolidin-3-yl)urea Step A: Preparation of phenyl (3-bromo-4-methyl-1-phenyl-1H-pyrazol-5-yl)carbamate To a solution of 3-bromo-4-methyl-1-phenyl-1H-pyrazol-5-amine [Preparation F] (339 mg, 1.34 mmol) in EtOAc (10 mL) was added 2N NaOH (2 mL, 4.0 mmol) followed by phenyl chloroformate (337 µL, 2.69 mmol). The mixture was stirred at ambient temperature for 5 hours then partitioned between water (30 mL) and EtOAc (30 mL) and the aqueous layer extracted with EtOAc (2×20 mL). The combined organic phases were washed with saturated NaHCO₃ (30 mL) and brine (30 mL), then dried over Na₂SO₄, filtered and concentrated in vacuo to afford phenyl (3-bromo-4-methyl-1-phenyl-1H-pyrazol-5-yl)carbamate which was used directly in the next step, assuming quantitative yield. MS (apci) m/z=374.0 (M+H).

Step B: Preparation of 1-(3-bromo-4-methyl-1-phenyl-1H-pyrazol-5-yl)-3-((3S,4R)-4-(3,4-difluorophenyl)-1-(2-methoxyethyl)pyrrolidin-3-yl)urea To a solution of (3S,4R)-4-(3,4-difluorophenyl)-1-(2-methoxyethyl)pyrrolidin-3-amine [Preparation B3] (464 mg, 1.41 mmol) and phenyl (3-bromo-4-methyl-1-phenyl-1H-pyrazol-5-yl)carbamate (500 mg, 1.34 mmol) in DCM (10 mL) was added DIEA (819 µL, 4.7 mmol). The solution was stirred at ambient temperature for 18 hours. The reaction mixture was partitioned between saturated NH₄Cl (30 mL) and DCM (30 mL) and the aqueous layer was extracted with DCM (2×20 mL). The combined organic phases were washed with brine (20 mL), dried over $Na_2SO_4$, filtered and concentrated in vacuo. The residue was purified by silica column chromatography eluting with 2% MeOH/DCM to afford 1-(3-bromo-4-methyl-1-phenyl-1H-pyrazol-5-yl)-3-((3S,4R)-4-(3,4-difluorophenyl)-1-(2-methoxyethyl)pyrrolidin-3-yl)urea (483 mg, 67% yield) as a white solid. MS (apci) m/z=534.1 (M+).

Step C: 1-(3-(2-(cyclopropylamino)pyrimidin-5-yl)-4-methyl-1-phenyl-1H-pyrazol-5-yl)-3-((3S,4R)-4-(3,4-difluorophenyl)-1-(2-methoxyethyl)pyrrolidin-3-yl)urea 1-(3-Bromo-4-methyl-1-phenyl-1H-pyrazol-5-yl)-3-((3S,4R)-4-(3,4-difluorophenyl)-1-(2-methoxyethyl) pyrrolidin-3-yl)urea (100 mg, 0.19 mmol), N-cyclopropyl-5-(4,4,5,5-tetramethyl-1,3,2-dioxaborolan-2-yl)pyrimidin-2-amine (147 mg, 0.56 mmol) and tricyclohexyl phosphine (11 mg, 0.04 mmol) were combined in 1,4-dioxanes (3 mL) and purged with Argon for 5 minutes. $Pd_2ba_3$ (17 mg, 0.02 mmol) and $K_3PO_4$ (432 μL, 1.3M, 0.56 mmol) were added and the mixture purged with Argon for a further 30 seconds then sealed and stirred at 100° C. for 16 hours. The cooled mixture was filtered and the filtrate was partitioned between water (20 mL) and EtOAc (20 mL). The aqueous layer was extracted with EtOAc (2×10 mL) and the combined organic phases were washed with brine (10 mL), dried over $Na_2SO_4$, filtered and concentrated in vacuo. The residue was purified by silica column chromatography eluting with 2.5-5% MeOH/DCM, then triturated with DCM, filtered and the filtrate concentrated to afford the title compound (14 mg, 13% yield) as a pale yellow solid. MS (apci) m/z=589.3 (M+H).

Example 21

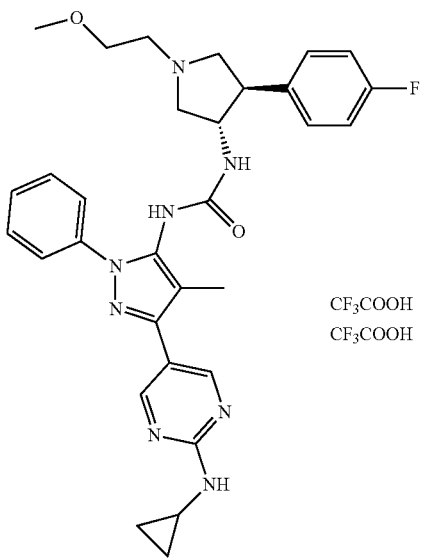 [SMILES: COCCN1C[C@@H](NC(=O)Nc2c(C)c(-c3cnc(NC4CC4)nc3)nn2-c2ccccc2)[C@H](c2ccc(F)cc2)C1 ; "CF3COOH" ; "CF3COOH"]

CF₃COOH
CF₃COOH 1-(3-(2-(cyclopropylamino)pyrimidin-5-yl)-4-methyl-1-phenyl-1H-pyrazol-5-yl)-3-((3S,4R)-4-(4-fluorophenyl)-1-(2-methoxyethyl)pyrrolidin-3-yl) urea di-trifluoroacetate Prepared according to the procedure of Example 20, replacing (3S,4R)-4-(3,4-difluorophenyl)-1-(2-methoxyethyl)pyrrolidin-3-amine [Preparation B3] with (3S,4R)-4-(4-fluorophenyl)-1-(2-methoxyethyl)pyrrolidin-3-amine [Preparation B1] in Step B. The crude material was purified by silica column chromatography eluting with 2.5-5% MeOH/DCM then reverse phase HPLC (5-95% ACN/water/0.1% TFA) to afford the title compound (26 mg, 17% yield) as a di-TFA salt as a colorless glass. MS (apci) m/z=571.3 (M+H).

Example 22

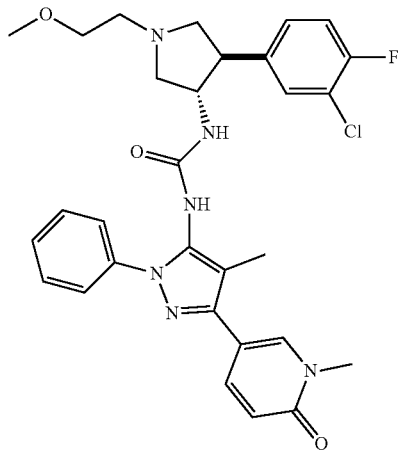 [SMILES: COCCN1C[C@@H](NC(=O)Nc2c(C)c(-c3ccc(=O)n(C)c3)nn2-c2ccccc2)[C@H](c2ccc(F)c(Cl)c2)C1]

1-(trans-4-(3-chloro-4-fluorophenyl)-1-(2-methoxyethyl)pyrrolidin-3-yl)-3-(4-methyl-3-(1-methyl-6-oxo-1,6-di hydropyridin-3-yl)-1-phenyl-1H-pyrazol-5-yl)urea To a solution of trans-4-(3-chloro-4-fluorophenyl)-1-(2-methoxyethyl)pyrrolidin-3-amine (Preparation B4, 12.7 mg, 0.0467 mmol) in DCM (1 mL) was added DIEA (0.016 mL, 0.093 mmol), followed by the addition of phenyl 4-methyl-3-(1-methyl-6-oxo-1,6-dihydropyridin-3-yl)-1-phenyl-1H-pyrazol-5-ylcarbamate (Preparation H, 18.7 mg, 0.047 mmol). The reaction mixture was stirred at ambient temperature for 1 hour, then purified by reverse-phase column chromatography, eluting with 0-70% acetonitrile/water, to afford the title compound (15 mg, 56% yield) as a pale yellow solid. MS (apci) m/z=579.2 (M+H).

Example 23

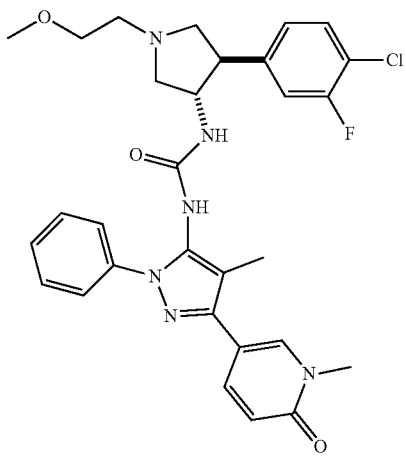 [SMILES: COCCN1C[C@@H](NC(=O)Nc2c(C)c(-c3ccc(=O)n(C)c3)nn2-c2ccccc2)[C@H](c2ccc(Cl)c(F)c2)C1]

1-(trans-4-(4-chloro-3-fluorophenyl)-1-(2-methoxyethyl)pyrrolidin-3-yl)-3-(4-methyl-3-(1-methyl-6-oxo-1,6-dihydropyridin-3-yl)-1-phenyl-1H-pyrazol-5-yl)urea Prepared according to the procedure of Example 22, replacing trans-4-(3-chloro-4-fluorophenyl)-1-(2-methoxyethyl)pyrrolidin-3-amine with trans-4-(4-chloro-3-fluorophenyl)-1-(2-methoxyethyl)pyrrolidin-3-amine [Preparation B5]. The reaction mixture was purified by reverse-phase column chromatography, eluting with 0-70% acetonitrile/water, to afford the title compound (16 mg, 60% yield) as a pale yellow solid. MS (apci) m/z=579.2 (M+H).

Example 24

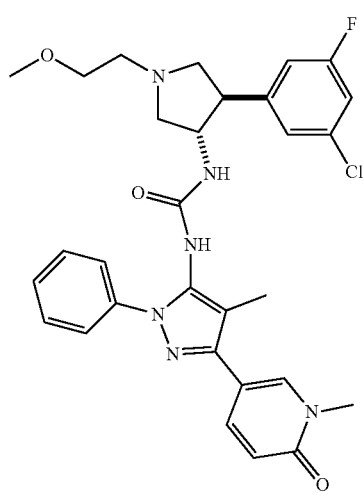

1-(trans-4-(3-chloro-5-fluorophenyl)-1-(2-methoxyethyl)pyrrolidin-3-yl)-3-(4-methyl-3-(1-methyl-6-oxo-1,6-di hydropyridin-3-yl)-1-phenyl-1H-pyrazol-5-yl)urea Prepared according to the procedure of Example 22, replacing trans-4-(3-chloro-4-fluorophenyl)-1-(2-methoxyethyl)pyrrolidin-3-amine with trans-4-(3-chloro-5-fluorophenyl)-1-(2-methoxyethyl)pyrrolidin-3-amine [Preparation B6]. The reaction mixture was purified by reverse-phase column chromatography, eluting with 0-70% acetonitrile/water, to afford the title compound (17 mg, 63% yield) as a pale yellow solid. MS (apci) m/z=579.2 (M+H).

Example 25

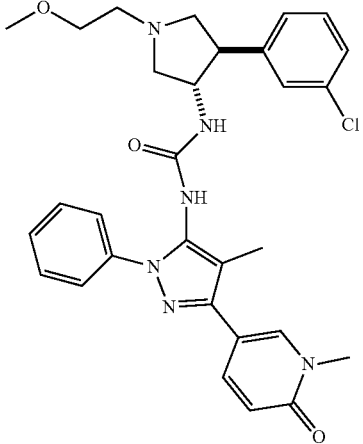

1-(trans-4-(3-chlorophenyl)-1-(2-methoxyethyl)pyrrolidin-3-yl)-3-(4-methyl-3-(1-methyl-6-oxo-1,6-di hydropyridin-3-yl)-1-phenyl-1H-pyrazol-5-yl)urea Prepared according to the procedure of Example 22, replacing trans-4-(3-chloro-4-fluorophenyl)-1-(2-methoxyethyl)pyrrolidin-3-amine with trans-4-(3-chlorophenyl)-1-(2-methoxyethyl)pyrrolidin-3-amine [Preparation B7]. The reaction mixture was purified by reverse-phase column chromatography, eluting with 0-70% acetonitrile/water, to afford the title compound (15 mg, 57% yield) as a white solid. MS (apci) m/z=561.2 (M+H).

Example 26

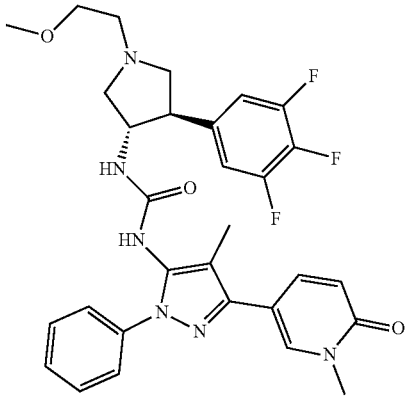 [SMILES: COCCN1C[C@@H](NC(=O)Nc2c(C)c(-c3ccc(=O)n(C)c3)nn2-c2ccccc2)[C@H](c2cc(F)c(F)c(F)c2)C1]

1-((3S,4R)-1-(2-methoxyethyl)-4-(3,4,5-trifluorophenyl)pyrrolidin-3-yl)-3-(4-methyl-3-(1-methyl-6-oxo-1,6-di hydropyridin-3-yl)-1-phenyl-1H-pyrazol-5-yl)urea A solution of triphosgene (23.1 mg, 0.0740 mmol) in dry CH₃CN (1 mL) was cooled to 0° C. and a solution of (3S,4R)-1-(2-methoxyethyl)-4-(3,4,5-trifluorophenyl)pyrrolidin-3-amine dihydrochloride (Preparation C, 76.4 mg, 0.220 mmol) and DIEA (115 µL, 0.660 mmol) in dry CH₃CN (0.5 mL) was added dropwise over 45 minutes. The mixture was stirred for 1 hour during which time temperature reached 15° C. 5-(5-Amino-4-methyl-1-phenyl-1H-pyrazol-3-yl)-1-methylpyridin-2(1H)-one (Preparation G, 56.1 mg, 0.200 mmol) was added in one portion and the mixture was stirred at ambient temperature for 7 hours followed by heating at 40° C. for 17 hours. The reaction mixture was cooled to ambient temperature and was diluted with chilled H₂O (4 mL) with thorough mixing. The cold mixture (pH=5) was treated with 2M NaOH to pH=10 and was extracted with EtOAc (3×). The combined extracts were washed with H₂O and saturated NaCl (2×). The EtOAc solution was dried over MgSO₄ and eluted through a short SiO₂ column eluting with EtOAc, 10% MeOH/EtOAc then 10% (9:1/CH₃OH—NH₄OH)/EtOAc. The product-containing pool was concentrated to a colorless glass. The glass was treated with Et₂O and agitated until white suspension formed. The solvent was decanted and the residual solid was washed with Et₂O (2×) and dried in vacuo to afford the title compound as a white solid (34 mg, 29% yield). MS (apci) m/z=581.2 (M+H).

Example 27

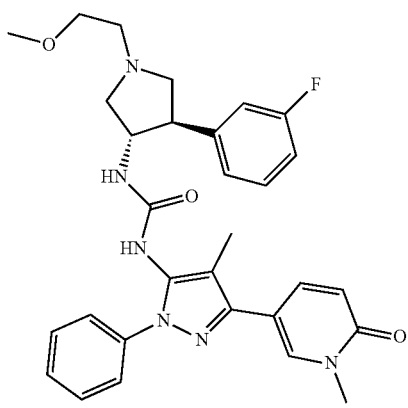 [SMILES: COCCN1C[C@@H](NC(=O)Nc2c(C)c(-c3ccc(=O)n(C)c3)nn2-c2ccccc2)[C@H](c2cccc(F)c2)C1]

1-((3S,4R)-4-(3-fluorophenyl)-1-(2-methoxyethyl) pyrrolidin-3-yl)-3-(4-methyl-3-(1-methyl-6-oxo-1,6-di hydropyridin-3-yl)-1-phenyl-1H-pyrazol-5-yl) urea A mixture of phenyl 4-methyl-3-(1-methyl-6-oxo-1,6-di hydropyridin-3-yl)-1-phenyl-1H-pyrazol-5-ylcarbamate (Preparation H, 60.1 mg, 0.150 mmol) and (3S,4R)-4-(3-fluorophenyl)-1-(2-methoxyethyl)pyrrolidin-3-amine dihydrochloride (Preparation D, 51.4 mg, 0.165 mmol) in DCM (1.0 mL) was treated with DIEA (86.3 µL, 0.495 mmol). The mixture was stirred at ambient temperature for 3 hours and was diluted with DCM (3 mL). The diluted reaction mixture was washed with H₂O (2×), 1M NaOH (2×) and H₂O and dried over Na₂SO₄/activated carbon. The solution was filtered, concentrated and the residue purified by silica column chromatography (EtOAc, 5% MeOH/EtOAc, 10% (9:1 MeOH/NH₄OH)/EtOAc step gradient elution). The resulting colorless glass was treated with Et₂O and agitated until a white granular suspension formed. The suspension was filtered, the solid washed with Et₂O and dried in vacuo to furnish the title compound as a white solid (46 mg, 56% yield). MS (apci) m/z=545.2 (M+H).

Example 28

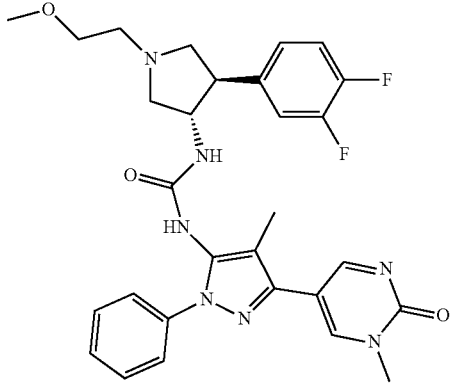 [SMILES: COCCN1C[C@@H](NC(=O)Nc2c(C)c(-c3cnc(=O)n(C)c3)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(4-methyl-3-(1-methyl-2-oxo-1,2-dihydropyrimidin-5-yl)-1-phenyl-1H-pyrazol-5-yl)urea Step A: Preparation of 5-(5-amino-4-methyl-1-phenyl-1H-pyrazol-3-yl)pyrimidin-2(1H)-one hydrochloride A solution of 3-(2-methoxypyrimidin-5-yl)-4-methyl-1-phenyl-1H-pyrazol-5-amine [Prepared as in 1, Step A] (200 mg, 0.71 mmol) in methanol (5 mL) was treated with 5-6 N HCl/isopropyl alcohol (5 mL) and stirred at reflux for 4 hours. The mixture was cooled to ambient temperature and the resulting solid filtered, washed with methanol and dried in vacuo to afford 3-(2-methoxypyrimidin-5-yl)-4-methyl-1-phenyl-1H-pyrazol-5-amine (152 mg, 72% yield) as a pale yellow powder. MS (apci) m/z=268.1 (M+H).

Step B: Preparation of 5-(5-amino-4-methyl-1-phenyl-1H-pyrazol-3-yl)-1-m ethylpyrimidin-2(1H)-one A solution of 3-(2-methoxypyrimidin-5-yl)-4-methyl-1-phenyl-1H-pyrazol-5-amine (50 mg, 0.16 mmol) DMA (1 mL) was treated with Cs₂CO₃ (161 mg, 0.49 mmol) and stirred at ambient temperature for 30 minutes. Methyl iodide (20 µL, 0.33 mmol) was then added and the mixture stirred, capped, at ambient temperature for 16 hours. The mixture was partitioned between water (20 mL) and EtOAc (20 mL) and the aqueous layer was extracted with EtOAc (2×10 mL). The combined organic phases were dried over Na₂SO₄, filtered and concentrated in vacuo. The residue was purified by silica column chromatography eluting with 2-5% MeOH/DCM to afford 5-(5-amino-4-methyl-1-phenyl-1H-pyrazol- 3-yl)-1-methyl pyrimidin-2(1H)-one (23 mg, 50% yield) as a pale yellow gum. MS (apci) m/z=282.1 (M+H).

Step C: Preparation of 1-((3S,4R)-4-(3,4-difluorophenyl)-1-(2-methoxyethyl)pyrrolidin-3-yl)-3-(4-methyl-3-(1-methyl-2-oxo-1,2-dihydropyrimidin-5-yl)-1-phenyl-1H-pyrazol-5-yl)urea To a solution of 5-(5-amino-4-methyl-1-phenyl-1H-pyrazol-3-yl)-1-methyl pyrimidin-2(1H)-one (23 mg, 0.08 mmol) in DCM (1 mL) was added triphosgene (12 mg, 0.04 mmol) and the mixture treated with DIEA (43 µL, 0.24 mmol). The solution was stirred for 30 minutes at ambient temperature then treated with (3S,4R)-4-(3,4-difluorophenyl)-1-(2-methoxyethyl)pyrrolidin-3-amine [Preparation B3] (27 mg, 0.08 mmol) and DIEA (42 µL, 0.24 mmol) and stirring continued for 48 hours. The mixture was partitioned between saturated $NH_4Cl$ (20 mL) and DCM (20 mL) and the aqueous layer extracted with DCM (2×10 mL) plus methanol (1 mL). The combined organic phases were filtered, concentrated in vacuo and purified by silica column chromatography eluting with 3-10% MeOH/DCM to afford the title compound (9 mg, 19% yield) as a pale yellow glass. MS (apci) m/z=564.2 (M+H).

Example 29

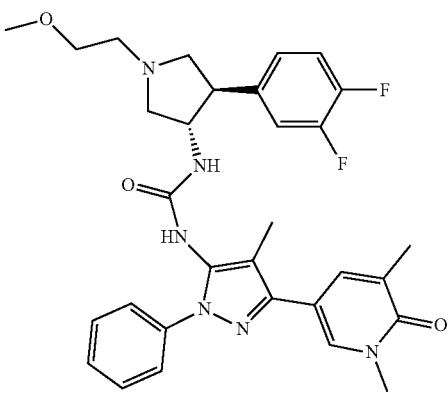 [SMILES: COCCN1C[C@@H](NC(=O)Nc2c(C)c(-c3cc(C)c(=O)n(C)c3)nn2-c2ccccc2)[C@H](c2ccc(F)c(F)c2)C1]

1-((3S,4R)-4-(3,4-difluorophenyl)-1-(2-methoxyethyl)pyrrolidin-3-yl)-3-(3-(1,5-dimethyl-6-oxo-1,6-di hydropyridin-3-yl)-4-methyl-1-phenyl-1H-pyrazol-5-yl)urea Step A: Preparation of 1,3-dimethyl-5-(4,4,5,5-tetramethyl-1,3,2-dioxaborolan-2-yl)pyridin-2(1H)-one 5-Bromo-1,3-dimethylpyridin-1(1H)-one (1.0 g, 4.94 mmol), bis(pinnacolato)diboron (1.38 g, 5.44 mmol) and potassium acetate (1.46 g, 14.8 mmol) were combined in dioxane (10 mL) in a sealed vessel and the mixture was de-gassed with argon for 5 minutes. Palladium acetate (111 mg, 0.49 mmol) and XPHOS (354 mg, 0.74 mmol) were added, and the mixture was degassed for an additional minute. The vessel was sealed and heated at 100° C. for 16 hours. The cooled mixture was filtered through GF paper and the filtrate was concentrated. The residue was triturated with ether and filtered, and the filtrate was concentrated to afford 1,3-dimethyl-5-(4,4,5,5-tetramethyl-1,3,2-dioxaborolan-2-yl)pyridin-2(1H)-one (assume quantitative yield) as a tan solid. MS (apci) m/z=250.2 (M+H).

Step B: Preparation of 5-(5-amino-4-methyl-1-phenyl-1H-pyrazol-3-yl)-1,3-dimethylpyridin-2(1H)-one 5-Amino-4-methyl-1-phenyl-1H-pyrazol-3-yl trifluoromethane sulfonate [Preparation E] (516 mg, 1.6 mmol), 1,3-dimethyl-5-(4,4,5,5-tetramethyl-1,3,2-dioxaborolan-2-yl)pyridin-2(1H)-one (600 mg, 2.41 mmol), $K_2CO_3$ (888 mg, 6.42 mmol) and Pd(PPh$_3$)$_4$ (185 mg, 0.16 mmol) were combined in toluene (10 mL), water (5 mL) and EtOH (2.5 mL) and warmed to 95° C. in a sealed vessel for 16 hours. The cooled mixture was filtered through GF paper and the filtrate was partitioned between water (50 mL) and EtOAc (50 mL). The aqueous layer was extracted with EtOAc (2×30 mL) and the combined organic phases were washed with brine (30 mL), dried over $Na_2SO_4$, filtered and concentrated. The residue was purified by silica column chromatography eluting with 2% MeOH/DCM to afford 5-(5-amino-4-methyl-1-phenyl-1H-pyrazol-3-yl)-1,3-dimethylpyridin-2(1H)-one (363 mg, 77% yield) as a dark pink foam. MS (apci) m/z=295.1 (M+H).

Step C: Preparation of 1-((3S,4R)-4-(3,4-difluorophenyl)-1-(2-methoxyethyl)pyrrolidin-3-yl)-3-(3-(1,5-dimethyl-6-oxo-1,6-di hydropyridin-3-yl)-4-methyl-1-phenyl-1H-pyrazol-5-yl)urea To a solution of 5-(5-amino-4-methyl-1-phenyl-1H-pyrazol-3-yl)-1,3-dimethylpyridin-2(1H)-one (45 mg, 0.15 mmol) in anhydrous DCM (2 mL) was added triphosgene (23 mg, 0.08 mmol) followed by DIEA (79 µL, 0.46 mmol). The solution was stirred for 30 minutes at ambient temperature and then treated with (3S,4R)-4-(3,4-difluorophenyl)-1-(2-methoxyethyl)pyrrolidin-3-amine [Preparation B3] (50 mg, 0.15 mmol) and DIEA (79 µL, 0.46 mmol) and stirred for 16 hours. The mixture was partitioned between saturated $NH_4Cl$ (20 mL) and DCM (20 mL) and the aqueous layer was extracted with DCM (2×10 mL). The combined organic phases were washed with brine (10 mL), dried over $Na_2SO_4$, filtered and concentrated. The residue was purified by silica column chromatography eluting with 3-5% MeOH/DCM to afford the title compound (33 mg, 38% yield) as a colorless glass. MS (apci) m/z=577.3 (M+H).

Example 30

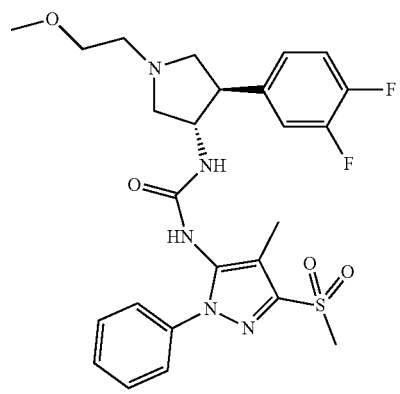 [SMILES: COCCN1C[C@@H](NC(=O)Nc2c(C)c(S(C)(=O)=O)nn2-c2ccccc2)[C@H](c2ccc(F)c(F)c2)C1]

1-((3S,4R)-4-(3,4-difluorophenyl)-1-(2-methoxy-ethyl)pyrrolidin-3-yl)-3-(4-methyl-3-(methylsulfonyl)-1-phenyl-1H-pyrazol-5-yl)urea

Step A: Preparation of 4-methyl-3-(methylsulfonyl)-1-phenyl-1H-pyrazol-5-amine 3-Bromo-4-methyl-1-phenyl-1H-pyrazol-5-amine [Preparation F] (300 mg, 1.19 mmol), sodium methanesulfinate (486 mg, 4.76 mmol) and copper iodide (249 mg, 1.31 mmol) were combined in DMSO (5 mL) and purged with bubbling argon for 5 minutes. The mixture was stirred at 100° C. in a sealed tube for 6 days, then the cooled mixture was partitioned between EtOAc (20 mL) and water (50 mL) containing a few drops of NH$_4$OH. The aqueous layer was extracted with EtOAc (2×30 mL) and the combined organic phases were washed with water (5×20 mL) and brine (20 mL), then dried over Na$_2$SO$_4$, filtered and concentrated. The residue was purified by silica column chromatography eluting with hexanes/EtOAc (2:1) to afford 4-methyl-3-(methylsulfonyl)-1-phenyl-1H-pyrazol-5-amine (89 mg, 30% yield) as a yellow, crystalline solid. MS (apci) m/z=252.1 (M+H).

Step B: Preparation of phenyl (4-methyl-3-(methylsulfonyl)-1-phenyl-1H-pyrazol-5-yl)carbamate To a solution of 4-methyl-3-(methylsulfonyl)-1-phenyl-1H-pyrazol-5-amine (45 mg, 0.18 mmol) in EtOAc (2 mL) was added 2N NaOH (269 μL, 0.54 mmol) followed by phenyl chloroformate (45 μL, 0.36 mmol). The mixture was stirred at ambient temperature for 16 hours, and then phenyl chloroformate (75 μL) was added and the mixture stirred for 4 hours. The mixture was partitioned between water (10 mL) and EtOAc (10 mL) and the aqueous layer extracted with EtOAc (2×10 mL). The combined organic phases were washed with brine (10 mL), then dried over Na$_2$SO$_4$, filtered and concentrated to afford phenyl (4-methyl-3-(methylsulfonyl)-1-phenyl-1H-pyrazol-5-yl)carbamate (50 mg, 75% yield) as a pale yellow foam. MS (apci) m/z=372.1 (M+H).

Step C: Preparation of 1-((3S,4R)-4-(3,4-difluorophenyl)-1-(2-methoxyethyl)pyrrolidin-3-yl)-3-(4-methyl-3-(methylsulfonyl)-1-phenyl-1H-pyrazol-5-yl)urea To a solution of (3S,4R)-4-(3,4-difluorophenyl)-1-(2-methoxyethyl)pyrrolidin-3-amine [Preparation B3] (38 mg, 0.15 mmol) in anhydrous DCM (2 mL) was added phenyl (4-methyl-3-(methylsulfonyl)-1-phenyl-1H-pyrazol-5-yl)carbamate (50 mg, 0.13 mmol) followed by DIEA (70 μL, 0.40 mmol). The mixture was stirred at ambient temperature for 16 hours, then partitioned between water (10 mL) and DCM (10 mL). The aqueous layer was extracted with DCM (2×10 mL) and the combined organic phases were washed with brine (10 mL), dried over Na$_2$SO$_4$, filtered and concentrated. The residue was purified by silica column chromatography eluting with 2% MeOH/DCM to afford the title compound (27 mg, 37% yield) as a white solid. MS (apci) m/z=534.2 (M+H).

Example 31

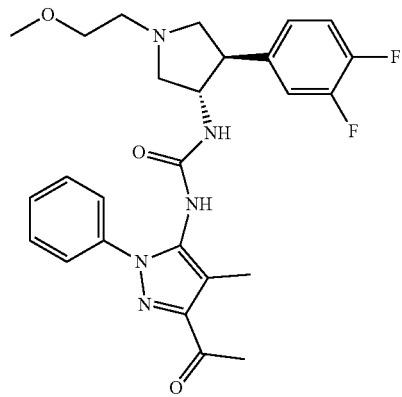 [SMILES: COCCN1C[C@@H](NC(=O)Nc2c(C)c(C(C)=O)nn2-c2ccccc2)[C@H](c2ccc(F)c(F)c2)C1]

1-(3-acetyl-4-methyl-1-phenyl-1H-pyrazol-5-yl)-3-((3S,4R)-4-(3,4-difluorophenyl)-1-(2-methoxyethyl)pyrrolidin-3-yl)urea

Step A: Preparation of ethyl 3-cyano-2-oxobutanoate

To a solution of lithium bis(trimethylsilyl)amide (1.0 M in THF) (73.63 mL, 73.63 mmol) and THF (75 mL) under N$_2$ at −78° C. was added propionitrile (6.304 mL, 88.35 mmol) dropwise over 2 minutes, and the mixture was stirred for 1 hour. The mixture was then treated with diethyl oxalate (10 mL, 73.63 mmol) dropwise over 5 minutes, stirred at −78° C. for 45 minutes, and then stirred at 0° C. for 1 hour. The mixture was diluted with H$_2$O (100 mL) and extracted with Et$_2$O (100 mL). The aqueous phase was adjusted to pH 5 with 6M HCl (13 mL) and then extracted with Et$_2$O (3×100 mL). These organic extracts were washed with brine (100 mL), dried over MgSO$_4$, filtered and concentrated to afford ethyl 3-cyano-2-oxobutanoate (11.42 g, 99% yield) as a yellow-orange oil.

Step B: Preparation of ethyl 5-amino-4-methyl-1-phenyl-1H-pyrazole-3-carboxylate To a solution of ethyl 3-cyano-2-oxobutanoate (11.42 g, 73.6 mmol) in EtOH (300 mL) was added phenylhydrazine (7.2 mL, 73.6 mmol) followed by hydrogen chloride (5-6 M in iPrOH) (14.7 mL, 73.6 mmol). The reaction mixture was stirred at reflux for 16 hours, then cooled and concentrated to 50 mL. The residue was diluted with saturated NaHCO$_3$ (150 mL) and H$_2$O (50 mL) and extracted with DCM (3×200 mL). The combined organic phases were dried over MgSO$_4$, filtered and concentrated. The residue was purified by silica column chromatography eluting with 0-50% acetone/hexanes to afford ethyl 5-amino-4-methyl-1-phenyl-1H-pyrazole-3-carboxylate (7.49 g, 49% yield) as an orange solid after drying in vacuo. MS (apci) m/z=246.1 (M+H).

Step C: Preparation of 5-amino-4-methyl-1-phenyl-1H-pyrazole-3-carboxylic acid To a solution of ethyl 5-amino-4-methyl-1-phenyl-1H-pyrazole-3-carboxylate (3.0 g, 12.2 mmol) in THF (24 mL) and MeOH (12 mL) was added LiOH (2M aq) (13.5 mL, 27.0 mmol) and the mixture was stirred at ambient temperature for 3 hours. The mixture was partially concentrated and then adjusted to pH 3 with 6M HCl (4.5 mL) and extracted with 10% MeOH/DCM (3×25 mL). The aqueous phase was further acidified with 6M HCl (1 mL) to pH 1, and then extracted with 10% MeOH/DCM (3×25 mL). The aqueous phase was saturated with NaCl and extracted with 10% MeOH/DCM (3×25 mL). The combined organic extracts were washed with brine (50 mL), dried over MgSO$_4$, filtered and concentrated to afford 5-amino-4-methyl-1-phenyl-1H-pyrazole-3-carboxylic acid (2.4 g, 90% yield) as a tan solid. MS (apci) m/z=218.1 (M+H).

Step D: Preparation of 5-amino-N-m ethoxy-N,4-dimethyl-1-phenyl-1H-pyrazole-3-carboxamide To a solution of 5-amino-4-methyl-1-phenyl-1H-pyrazole-3-carboxylic acid (1.0 g, 4.6 mmol) in ACN (46 mL) were added N,O-dimethylhydroxylamine hydrochloride (539 mg, 5.5 mmol) and DIEA (2.4 mL, 13.8 mmol). The mixture was stirred until a solution formed and was then treated with HATU (2.1 g, 5.52 mmol) and stirred at ambient temperature for 90 minutes. The reaction mixture was diluted with H$_2$O (50 mL) and extracted with DCM (2×50 mL). The combined organic extracts were washed with brine (50 mL), dried over MgSO$_4$, filtered and concentrated. The residue was purified by silica column chromatography eluting with 0-50% acetone in hexanes to afford 5-amino-N-methoxy-N,4-dimethyl-1-phenyl-1H-pyrazole-3-carboxamide (550 mg, 46% yield) as a peachy-tan solid. MS (apci) m/z=261.1 (M+H).

Step E: Preparation of 1-(5-amino-4-methyl-1-phenyl-1H-pyrazol-3-yl)ethanone

A solution of 5-amino-N-methoxy-N,4-dimethyl-1-phenyl-1H-pyrazole-3-carboxamide (365 mg, 1.40 mmol) in DCM (15 mL) was cooled to 0° C. under N$_2$, and added MeMgBr (3M in Et$_2$O) (491 µL, 1.47 mmol) was added dropwise, over 4 minutes. The mixture was stirred at ambient temperature for 1 hour and then treated with DCM (5 mL) and stirred for 90 minutes. The mixture was cooled to 0° C., and MeMgBr (0.3 mL) was added. The mixture was stirred at ambient temperature for 30 minutes, then cooled to 0° C. and treated with MeMgBr (0.4 mL). The mixture was stirred at ambient temperature for 15 minutes. The reaction mixture was cooled to 0° C., quenched with saturated NH$_4$Cl (25 mL), and extracted with DCM (3×25 mL). The combined organic extracts were dried over MgSO$_4$, filtered and concentrated. The residue was purified by silica column chromatography eluting with 0-50% acetone in hexanes to afford 1-(5-amino-4-methyl-1-phenyl-1H-pyrazol-3-yl)ethanone (189 mg, 63% yield). MS (apci) m/z=216.1 (M+H).

Step F: Preparation of phenyl (3-acetyl-4-methyl-1-phenyl-1H-pyrazol-5-yl)carbamate To a solution of 1-(5-amino-4-methyl-1-phenyl-1H-pyrazol-3-yl)ethanone (89 mg, 0.41 mmol) in EtOAc (4 mL) were added NaOH (0.41 mL, 2M, 0.83 mmol) then phenylchloroformate (62 µL, 0.49 mmol). The mixture was stirred at ambient temperature for 17 hours and then diluted with 10 mL EtOAc. The phases were separated, and the organic phase was washed with H$_2$O (20 mL) and brine (20 mL), then dried over MgSO$_4$, filtered and concentrated. The residue was treated with hexanes (3 mL) and sonicated. The resulting solids were allowed to settle, the hexanes removed with a pipette and the solids were dried in vacuo to afford phenyl (3-acetyl-4-methyl-1-phenyl-1H-pyrazol-5-yl)carbamate (133 mg, 99% yield) as pale yellow powder. MS (apci) m/z=336.1 (M+H).

Step G: Preparation of 1-(3-acetyl-4-methyl-1-phenyl-1H-pyrazol-5-yl)-3S,4R)-4-(3,4-difluorophenyl)-1-(2-methoxyethyl)pyrrolidin-3-yl)urea A solution of (3S,4R)-4-(3,4-difluorophenyl)-1-(2-methoxyethyl)pyrrolidin-3-amine [Preparation B3] (105.8 mg, 0.41 mmol) in iPrOH (2 mL) was added to phenyl (3-acetyl-4-methyl-1-phenyl-1H-pyrazol-5-yl)carbamate (133 mg, 0.40 mmol). The mixture was stirred at reflux for 10 minutes and then allowed to cool slowly to ambient temperature over 16 hours. The mixture was diluted with iPrOH (0.5 mL), then filtered, washed with iPrOH (2×0.5 mL) and Et$_2$O (3×1 mL) and dried in vacuo to afford the title product (113 mg, 57% yield) as an off-white solid. MS (apci) m/z=498.2 (M+H).

What is claimed is:

1. A method for treating a disease or disorder selected from pain and cancer, in a mammal in need thereof, which comprises administering to said mammal a therapeutically effective amount of a compound of Formula I compound of Formula I:

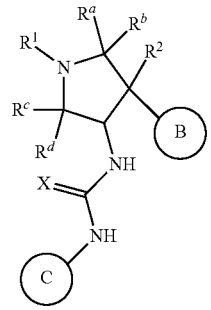

I or a pharmaceutically acceptable salt thereof, wherein:
Ring B and the NH—C(=X)—NH moiety are in the trans configuration;
R$^a$, R$^b$, R$^c$ and R$^d$ are H;
X is O;
R$^1$ is (1-3C alkoxy)(1-6C)alkyl;
R$^2$ is H;
Ring B is Ar$^1$;
Ar$^1$ is phenyl optionally substituted with one or more substituents independently selected from halogen;
Ring C is

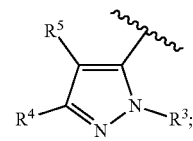

R$^3$ is Ar$^2$;
Ar$^2$ is phenyl optionally substituted with one or more substituents independently selected from halogen;

R⁴ is selected from (1-6C alkyl)SO₂—, (1-6C alkyl)C(=O)— and from the structures:

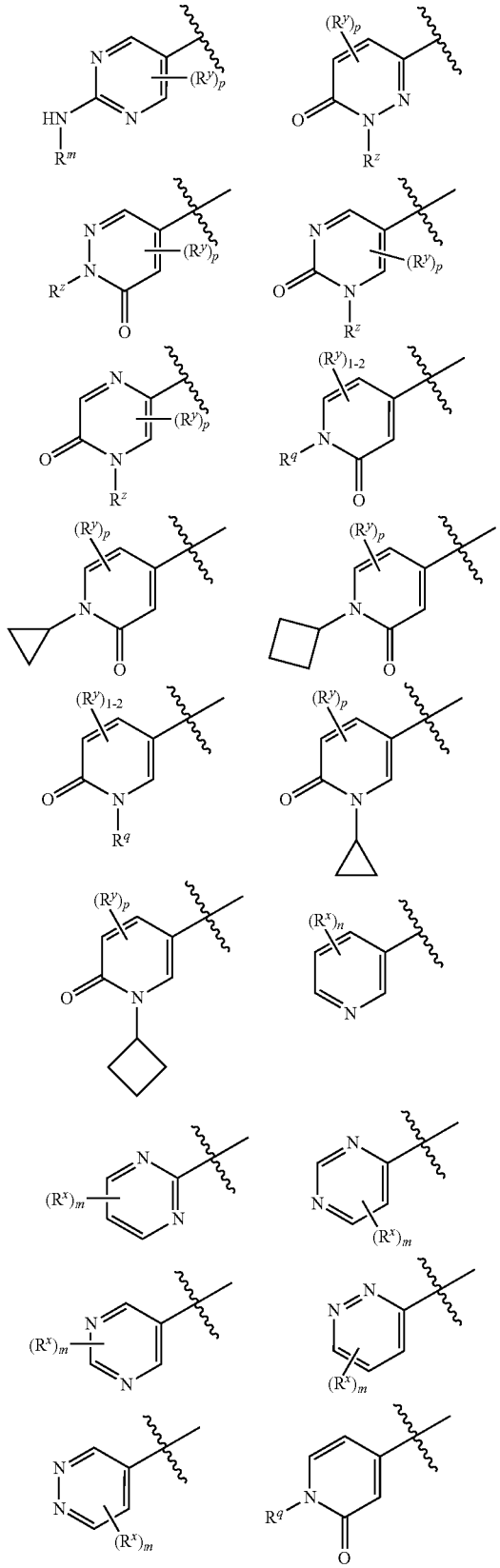

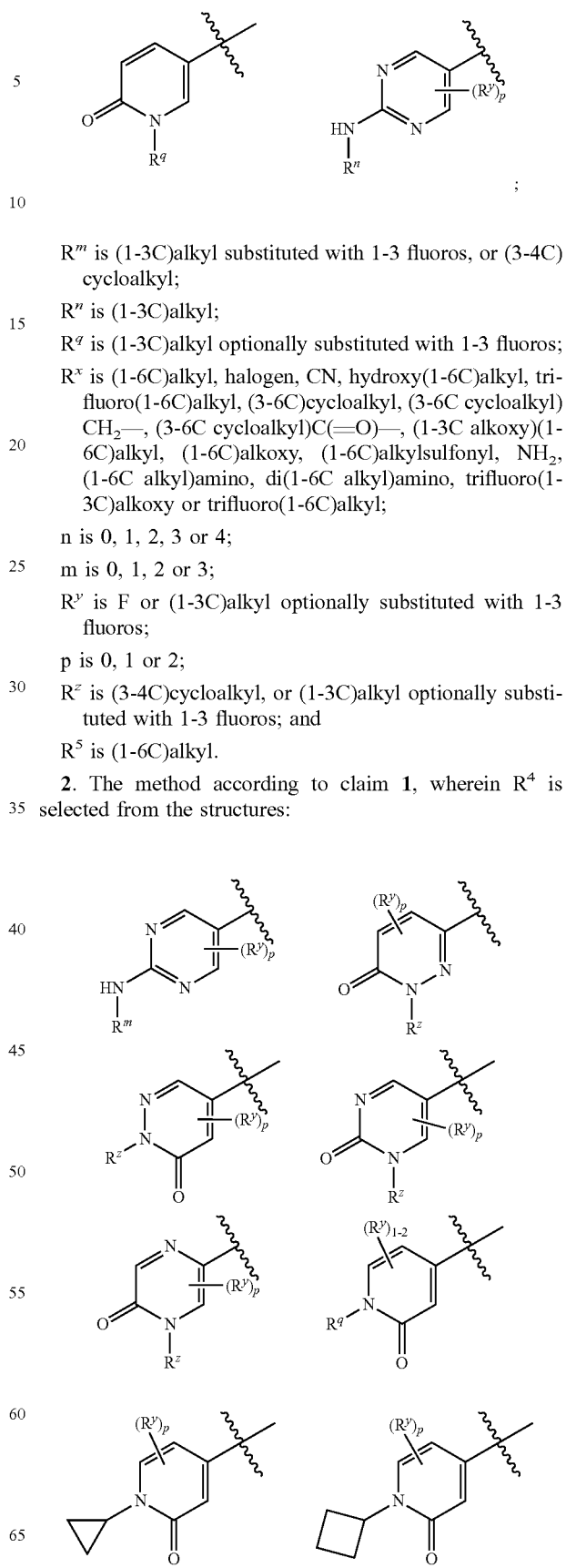

$R^m$ is (1-3C)alkyl substituted with 1-3 fluoros, or (3-4C)cycloalkyl;

$R^n$ is (1-3C)alkyl;

$R^q$ is (1-3C)alkyl optionally substituted with 1-3 fluoros;

$R^x$ is (1-6C)alkyl, halogen, CN, hydroxy(1-6C)alkyl, trifluoro(1-6C)alkyl, (3-6C)cycloalkyl, (3-6C cycloalkyl)CH₂—, (3-6C cycloalkyl)C(=O)—, (1-3C alkoxy)(1-6C)alkyl, (1-6C)alkoxy, (1-6C)alkylsulfonyl, NH₂, (1-6C alkyl)amino, di(1-6C alkyl)amino, trifluoro(1-3C)alkoxy or trifluoro(1-6C)alkyl;

n is 0, 1, 2, 3 or 4;

m is 0, 1, 2 or 3;

$R^y$ is F or (1-3C)alkyl optionally substituted with 1-3 fluoros;

p is 0, 1 or 2;

$R^z$ is (3-4C)cycloalkyl, or (1-3C)alkyl optionally substituted with 1-3 fluoros; and $R^5$ is (1-6C)alkyl.

2. The method according to claim 1, wherein $R^4$ is selected from the structures:

-continued
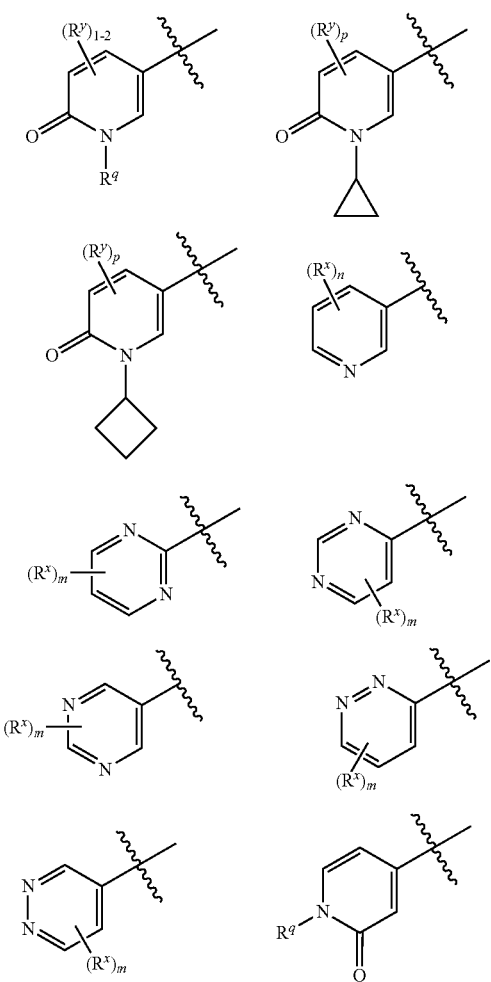
3. The method according to claim 1, wherein $R^4$ is selected from the structures:
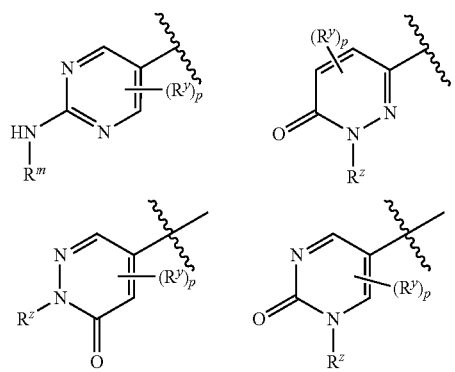
-continued
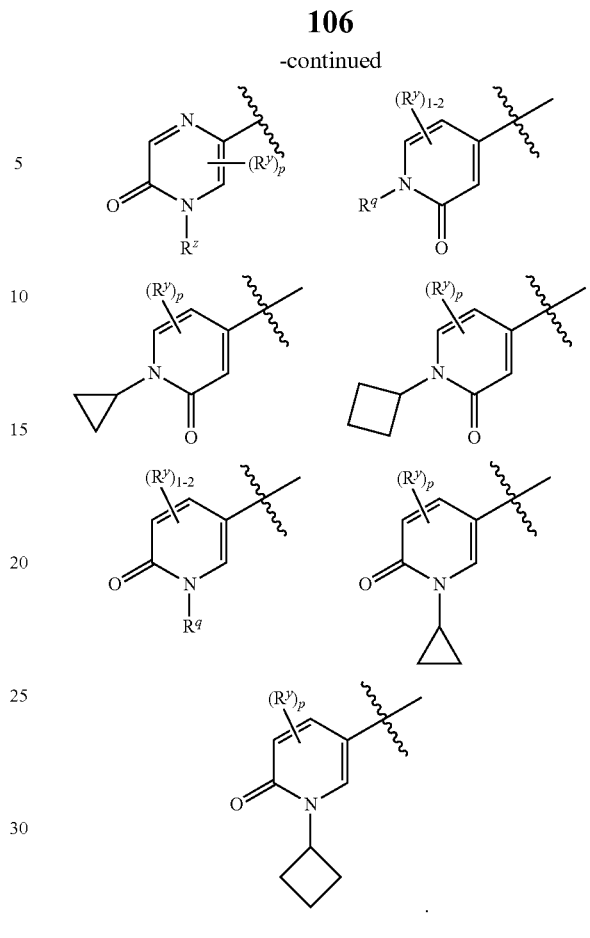
4. The method according to claim 3, wherein $R^4$ is selected from the structures:
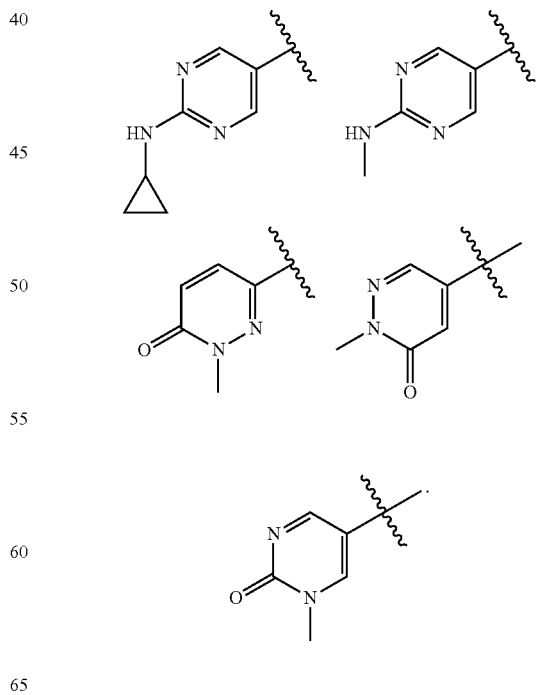
5. The method according to claim 1, wherein $R^4$ is selected from the structures:

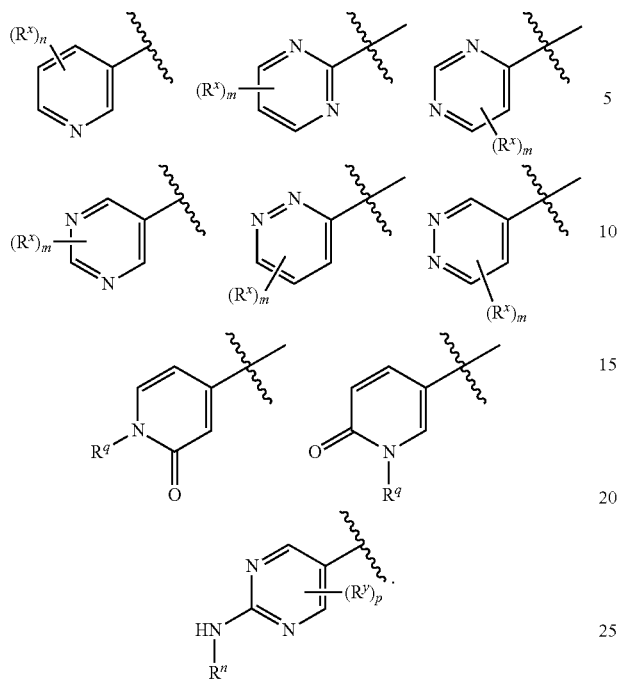

6. The method according to claim 5, wherein n is 0 or 1 and m is 0 or 1.

7. The method according to claim 6, wherein $R^4$ is selected from the structures:

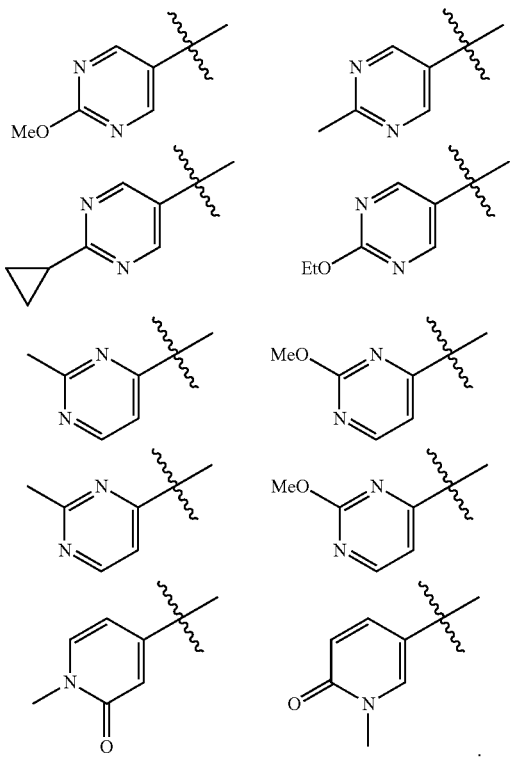

8. The method according to claim 1, wherein Ring B and the —NH—C(=X)—NH— moiety of Formula I are trans in the absolute configuration shown in structure C:

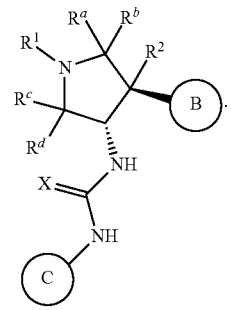

Structure C

9. The method according to claim 1, wherein Ring B and the —NH—C(=X)—NH— moiety of Formula I are trans in the absolute configuration shown in structure D:

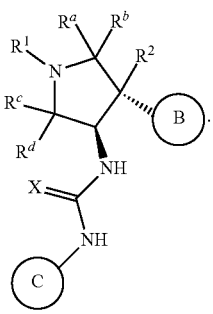

Structure D

10. The method of claim 1, wherein said compound is selected from:
- 1-((3S,4R)-4-(3,4-difluorophenyl)-1-(2-methoxyethyl) pyrrolidin-3-yl)-3-(4-methyl-3-(6-methylpyridin-3-yl)-1-phenyl-1H-pyrazol-5-yl)urea;
- 1-((3S,4R)-4-(3,4-difluorophenyl)-1-(2-methoxyethyl) pyrrolidin-3-yl)-3-(3-(2-fluoropyridin-3-yl)-4-methyl-1-phenyl-1H-pyrazol-5-yl)urea;
- 1-((3S,4R)-4-(3,4-difluorophenyl)-1-(2-methoxyethyl) pyrrolidin-3-y)-3-(4-methyl-3-(2-methylpyridin-3-yl)-1-phenyl-1H-pyrazol-5-yl)urea;
- 1-((3S,4R)-4-(3,4-difluorophenyl)-1-(2-methoxyethyl) pyrrolidin-3-yl)-3-(4-methyl-3-(5-methylpyridin-3-yl)-1-phenyl-1H-pyrazol-5-yl)urea;
- 1-((3S,4R)-4-(3,4-difluorophenyl)-1-(2-methoxyethyl) pyrrolidin-3-yl)-3-(3-(5-methoxypyridin-3-yl)-4-methyl-1-phenyl-1H-pyrazol-5-yl)urea;
- 1-(3-(5-cyanopyridin-3-yl)-4-methyl-1-phenyl-1H-pyrazol-5-yl)-3-((3S,4R)-4-(3,4-difluorophenyl)-1-(2-methoxyethyl)pyrrolidin-3-yl)urea;
- 1-((3S,4R)-4-(3,4-difluorophenyl)-1-(2-methoxyethyl) pyrrolidin-3-yl)-3-(3-(6-methoxypyridin-3-yl)-4-methyl-1-phenyl-1H-pyrazol-5-yl)urea;
- 1-((3S,4R)-4-(3,4-difluorophenyl)-1-(2-methoxyethyl) pyrrolidin-3-yl)-3-(3-(2-ethoxypyrimidin-5-yl)-4-methyl-1-phenyl-1H-pyrazol-5-yl)urea;
- 1-(3-(2-cyclopropylpyrimidin-5-yl)-4-methyl-1-phenyl-1H-pyrazol-5-yl)-3-((3S,4R)-4-(3,4-difluorophenyl)-1-(2-methoxyethyl)pyrrolidin-3-yl)urea;
- 1-(3-(2-cyclopropylpyrimidin-5-yl)-4-methyl-1-phenyl-1H-pyrazol-5-yl)-3-((3S,4R)-4-(4-fluorophenyl)-1-(2-methoxyethyl)pyrrolidin-3-yl)urea;

1-((3S,4R)-4-(3,5-difluorophenyl)-1-(2-methoxyethyl) pyrrolidin-3-yl)-3-(3-(2-methoxypyrimidin-5-yl)-4-methyl-1-phenyl-1H-pyrazol-5-yl)urea;

1-((3S,4R)-4-(4-fluorophenyl)-1-(2-methoxyethyl)pyrrolidin-3-yl)-3-(4-methyl-3-(2-methylpyrimidin-5-yl)-1-phenyl-1H-pyrazol-5-yl)urea;

1-((3S,4R)-4-(3,5-difluorophenyl)-1-(2-methoxyethyl) pyrrolidin-3-yl)-3-(4-methyl-3-(2-methylpyrimidin-5-yl)-1-phenyl-1H-pyrazol-5-yl)urea;

1-(3-(2-ethoxypyrimidin-5-yl)-4-methyl-1-phenyl-1H-pyrazol-5-yl)-3-((3S,4R)-4-(4-fluorophenyl)-1-(2-methoxyethyl)pyrrolidin-3-yl)urea;

1-((3S,4R)-4-(3,5-difluorophenyl)-1-(2-methoxyethyl) pyrrolidin-3-yl)-3-(3-(2-ethoxypyrimidin-5-yl)-4-methyl-1-phenyl-1H-pyrazol-5-yl)urea;

1-((3S,4R)-4-(3,4-difluorophenyl)-1-(2-methoxyethyl) pyrrolidin-3-yl)-3-(4-methyl-3-(1-methyl-6-oxo-1,6-dihydropyridazin-3-yl)-1-phenyl-1H-pyrazol-5-yl) urea;

1-((3S,4R)-4-(4-fluorophenyl)-1-(2-methoxyethyl)pyrrolidin-3-yl)-3-(4-methyl-3-(1-methyl-6-oxo-1,6-dihydropyridazin-3-yl)-1-phenyl-1H-pyrazol-5-yl)urea;

1-((3S,4R)-4-(3,5-difluorophenyl)-1-(2-methoxyethyl) pyrrolidin-3-yl)-3-(4-methyl-3-(1-methyl-6-oxo-1,6-dihydropyridazin-3-yl)-1-phenyl-1H-pyrazol-5-yl) urea;

1-(3-(2-(cyclopropylamino)pyrimidin-5-yl)-4-methyl-1-phenyl-1H-pyrazol-5-yl)-3-((3S,4R)-4-(3,4-difluorophenyl)-1-(2-methoxyethyl)pyrrolidin-3-yl)urea;

1-(3-(2-(cyclopropylamino)pyrimidin-5-yl)-4-methyl-1-phenyl-1H-pyrazol-5-yl)-3-((3S,4R)-4-(4-fluorophenyl)-1-(2-methoxyethyl)pyrrolidin-3-yl)urea;

1-(trans-4-(3-chloro-4-fluorophenyl)-1-(2-methoxyethyl) pyrrolidin-3-yl)-3-(4-methyl-3-(1-methyl-6-oxo-1,6-dihydropyridin-3-yl)-1-phenyl-1H-pyrazol-5-yl)urea;

1-(trans-4-(4-chloro-3-fluorophenyl)-1-(2-methoxyethyl) pyrrolidin-3-yl)-3-(4-methyl-3-(1-methyl-6-oxo-1,6-dihydropyridin-3-yl)-1-phenyl-1H-pyrazol-5-yl)urea;

1-(trans-4-(3-chloro-5-fluorophenyl)-1-(2-methoxyethyl) pyrrolidin-3-yl)-3-(4-methyl-3-(1-methyl-6-oxo-1,6-dihydropyridin-3-yl)-1-phenyl-1H-pyrazol-5-yl)urea;

1-(trans-4-(3-chlorophenyl)-1-(2-methoxyethyl)pyrrolidin-3-yl)-3-(4-methyl-3-(1-methyl-6-oxo-1,6-dihydropyridin-3-yl)-1-phenyl-1H-pyrazol-5-yl)urea;

1-((3S,4R)-4-(3,4-difluorophenyl)-1-(2-methoxyethyl) pyrrolidin-3-yl)-3-(4-methyl-3-(1-methyl-2-oxo-1,2-dihydropyrimidin-5-yl)-1-phenyl-1H-pyrazol-5-yl) urea;

1-((3S,4R)-4-(3,4-difluorophenyl)-1-(2-methoxyethyl) pyrrolidin-3-yl)-3-(3-(1,5-dimethyl-6-oxo-1,6-dihydropyridin-3-yl)-4-methyl-1-phenyl-1H-pyrazol-5-yl) urea;

1-((3S,4R)-4-(3,4-difluorophenyl)-1-(2-methoxyethyl) pyrrolidin-3-yl)-3-(4-methyl-3-(methylsulfonyl)-1-phenyl-1H-pyrazol-5-yl)urea;

1-(3-acetyl-4-methyl-1-phenyl-1H-pyrazol-5-yl)-3-((3S,4R)-4-(3,4-difluorophenyl)-1-(2-methoxyethyl)pyrrolidin-3-yl)urea;

and pharmaceutically acceptable salts thereof.

11. The method of claim 1, wherein said pain is chronic pain.

12. The method of claim 1, wherein said pain is acute pain.

13. The method of claim 1, wherein said pain is selected from inflammatory pain, neuropathic pain, pain associated with cancer, pain associated with surgery, and pain associated with bone fracture.

14. The method of claim 10, wherein said pain is chronic pain.

15. The method of claim 10, wherein said pain is acute pain.

16. The method of claim 10, wherein said pain is selected from inflammatory pain, neuropathic pain, pain associated with cancer, pain associated with surgery, and pain associated with bone fracture.

* * * * *

UNITED STATES PATENT AND TRADEMARK OFFICE
CERTIFICATE OF CORRECTION

PATENT NO. : 10,851,080 B2
APPLICATION NO. : 15/851418
DATED : December 1, 2020
INVENTOR(S) : Shelley Allen et al.

Page 1 of 1

It is certified that error appears in the above-identified patent and that said Letters Patent is hereby corrected as shown below:

In the Claims

Column 102, Lines 25-26, Claim 1, please delete "treating a disease or disorder selected from pain and cancer in a mammal" and insert -- treating pain in a mammal --;

Column 108, Line 44, Claim 10, please delete "pyrrolidin-3-y)-3-…" and insert -- pyrrolidin-3-yl)-3-… -- therefor.

Signed and Sealed this
Twentieth Day of July, 2021

Drew Hirshfeld
*Performing the Functions and Duties of the
Under Secretary of Commerce for Intellectual Property and
Director of the United States Patent and Trademark Office*